(12) United States Patent
Rothbaum

(10) Patent No.: US 12,268,681 B2
(45) Date of Patent: Apr. 8, 2025

(54) METHODS OF TREATING MYELOPROLIFERATIVE NEOPLASMS

(71) Applicant: Kartos Therapeutics, Inc., Redwood City, CA (US)

(72) Inventor: Wayne Rothbaum, Delray Beach, FL (US)

(73) Assignee: Kartos Therapeutics, Inc., Redwood City, CA (US)

( * ) Notice: Subject to any disclaimer, the term of this patent is extended or adjusted under 35 U.S.C. 154(b) by 1039 days.

(21) Appl. No.: 17/057,913

(22) PCT Filed: May 25, 2019

(86) PCT No.: PCT/IB2019/095002
§ 371 (c)(1),
(2) Date: Nov. 23, 2020

(87) PCT Pub. No.: WO2019/224803
PCT Pub. Date: Nov. 28, 2019

(65) Prior Publication Data
US 2022/0054472 A1 Feb. 24, 2022

Related U.S. Application Data

(60) Provisional application No. 62/835,311, filed on Apr. 17, 2019, provisional application No. 62/814,781, filed on Mar. 6, 2019, provisional application No. 62/781,923, filed on Dec. 19, 2018, provisional application No. 62/676,495, filed on May 25, 2018.

(51) Int. Cl.
| | |
|---|---|
| A61K 31/451 | (2006.01) |
| A61K 9/00 | (2006.01) |
| A61K 31/706 | (2006.01) |
| A61K 38/21 | (2006.01) |
| A61K 45/06 | (2006.01) |
| A61P 35/02 | (2006.01) |

(52) U.S. Cl.
CPC .......... *A61K 31/451* (2013.01); *A61K 9/0019* (2013.01); *A61K 31/706* (2013.01); *A61K 38/212* (2013.01); *A61K 45/06* (2013.01); *A61P 35/02* (2018.01)

(58) Field of Classification Search
None
See application file for complete search history.

(56) References Cited

U.S. PATENT DOCUMENTS

| | | |
|---|---|---|
| 2012/0077798 A1 | 3/2012 | Rodgers et al. |
| 2014/0011803 A1 | 1/2014 | Burns et al. |
| 2016/0264526 A1* | 9/2016 | Bio .............. A61K 31/451 |
| 2016/0287569 A1 | 10/2016 | Caenepeel et al. |
| 2016/0331754 A1 | 11/2016 | Dansey et al. |
| 2017/0008904 A1 | 1/2017 | Crew et al. |

FOREIGN PATENT DOCUMENTS

| | | |
|---|---|---|
| CN | 105358530 A | 2/2016 |
| CN | 105121407 A | 7/2017 |
| JP | 2010-520892 A | 6/2010 |
| JP | 2011-514909 A | 8/2013 |
| JP | 2016-504307 | 2/2016 |
| JP | 2016-526179 A | 9/2016 |
| JP | 2017-503001 A | 1/2017 |
| JP | 2016-535795 A | 12/2017 |
| JP | 2016-510028 A | 1/2018 |
| JP | 2017-519019 A | 7/2020 |
| KR | 10-2015-0091130 | 8/2015 |
| WO | 2015/070224 A2 | 5/2015 |

OTHER PUBLICATIONS

Bose et al., Clinical Lymphoma, Myeloma & Leukemia, 2017, vol. 17, No. S1, pp. S43-S52.
Samanta A et al: "Janus kinase 2 regulates Bcr-Abl signaling in chronic myeloid leukemia", Leukemia, vol. 25, No. 3, Dec. 24, 2010 (Dec. 24, 2010), pp. 463-472.pages.
Min Lu et al: "Combination treatment in vitro with Nutlin, a small-molecule antagonist of MDM2, and pegylated interferon-? 2a specifically targets JAK2V617F-positive polycythemia vera cells", Blood, Jan. 1, 2012 (Jan. 1, 2012), pp. 3098-3105.
Anonymous: "Idasanutlin Well Tolerated in Patients With Polycythemia Vera and Essential Thrombocythemia", ASH Clinical News, Feb. 2, 2018.
Partial Supplementary European Search Report dated Mar. 4, 2022 or European Patent Application No. 19807406.4, 17 pages.
International Search Report and Written Opinion dated Aug. 5, 2019 for International Patent Application No. PCT/IB2019/095002.
Gerds, Myeloproliferative Neoplasms, 2016, pp. 1-18; retrieved from the Internet: http://www.clevelandclinicmeded.com/medicalpubs/diseasemanagement/hematology-oncology/chronic-myeloproliferative-disorders/.
Pubchem-CID: 58573469 Create Date: Aug. 19, 2012; https://pubchem.ncbi.nlm.nih.gov/compound/amg-232.

(Continued)

*Primary Examiner* — Traviss C McIntosh, III

(74) *Attorney, Agent, or Firm* — Morgan, Lewis & Bockius LLP

(57) ABSTRACT

Therapeutic methods and pharmaceutical compositions for treating a myeloproliferative neoplasm (MPN), including polycythemia vera (PV), essential thrombocythemia (ET), and myelofibrosis, are described. In certain embodiments, the invention includes therapeutic methods of treating a MPN using a combination of a compound of Formula (I) or Formula (II) with a therapeutic agent selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

12 Claims, 1 Drawing Sheet
Specification includes a Sequence Listing.

(56) References Cited

OTHER PUBLICATIONS

Nakatake, JAK2V617F negatively regulates p53 stabilization by enhancing MDM2 via La expression in myeloproliferative neoplasms, Oncogene, 2012, vol. 31, pp. 1323-1333.

International Preliminary Report on Patentability dated Dec. 1, 2020 for International Patent Application No. PCT/IB2019/095002, 11 pages.

* cited by examiner

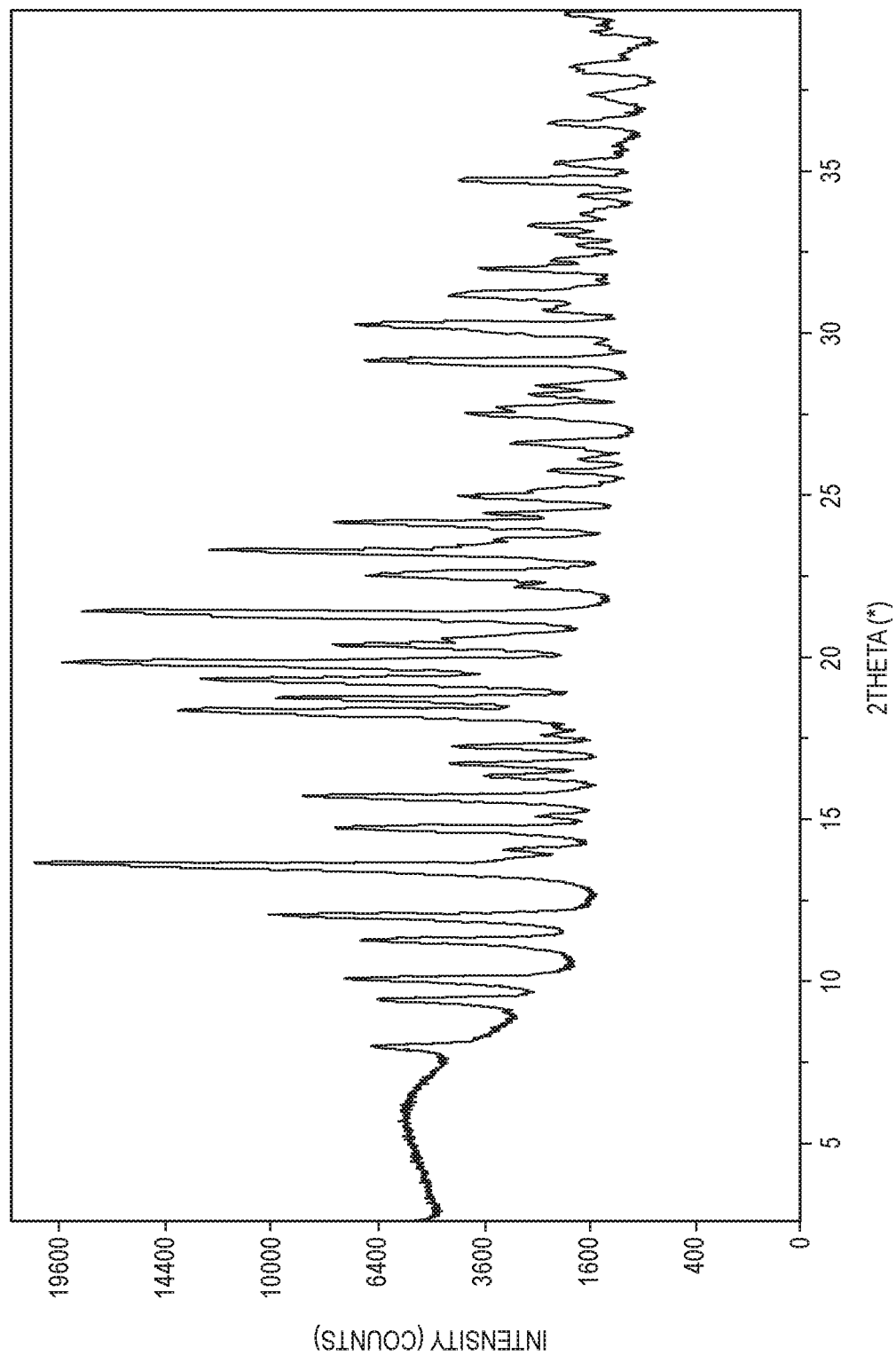

METHODS OF TREATING MYELOPROLIFERATIVE NEOPLASMS

FIELD OF THE INVENTION

Methods of treating a myeloproliferative neoplasm (MPN) using a Mouse double minute 2 homolog (MDM2) inhibitor and a therapeutic agent selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

BACKGROUND OF THE INVENTION p53 is a tumor suppressor and transcription factor that responds to cellular stress by activating the transcription of numerous genes involved in cell cycle arrest, apoptosis, senescence, and DNA repair. Unlike normal cells, which have infrequent cause for p53 activation, tumor cells are under constant cellular stress from various insults including hypoxia and pro-apoptotic oncogene activation. Thus, there is a strong selective advantage for inactivation of the p53 pathway in tumors, and it has been proposed that eliminating p53 function may be a prerequisite for tumor survival. In support of this notion, three groups of investigators have used mouse models to demonstrate that absence of p53 function is a continuous requirement for the maintenance of established tumors. When the investigators restored p53 function to tumors with inactivated p53, the tumors regressed.

p53 is inactivated by mutation and/or loss in 50% of solid tumors and 10% of liquid tumors. Other key members of the p53 pathway are also genetically or epigenetically altered in cancer. MDM2, an oncoprotein, inhibits p53 function, and it is activated by gene amplification at incidence rates that are reported to be as high as 10%. MDM2, in turn, is inhibited by another tumor suppressor, p14ARF. It has been suggested that alterations downstream of p53 may be responsible for at least partially inactivating the p53 pathway in p53 WT tumors (p53 wild type). In support of this concept, some p53WT tumors appear to exhibit reduced apoptotic capacity, although their capacity to undergo cell cycle arrest remains intact. One cancer treatment strategy involves the use of small molecules that bind MDM2 and neutralize its interaction with p53. MDM2 inhibits p53 activity by three mechanisms: 1) acting as an E3 ubiquitin ligase to promote p53 degradation; 2) binding to and blocking the p53 transcriptional activation domain; and 3) exporting p53 from the nucleus to the cytoplasm. All three of these mechanisms would be blocked by neutralizing the MDM2-p53 interaction. In particular, this therapeutic strategy could be applied to tumors that are p53 WT, and studies with small molecule MDM2 inhibitors have yielded promising reductions in tumor growth both in vitro and in vivo. Further, in patients with p53-inactivated tumors, stabilization of wild type p53 in normal tissues by MDM2 inhibition might allow selective protection of normal tissues from mitotic poisons. As used herein, MDM2 means a human MDM2 protein and p53 means a human p53 protein. It is noted that human MDM2 can also be referred to as HDM2 or hMDM2. Several MDM2 inhibitors are in human clinical trials for the treatment of various cancers.

The myeloproliferative neoplasms (MPN), including but not limited to: polycythemia vera (PV), essential thrombocythemia (ET), and primary myelofibrosis (PMF), are clonal hematopoietic stem cell (HSC) disorders characterized by the clonal proliferation of terminally differentiated myeloid cells. Approximately 1%, 4%, and 20% of ET, PV and PMF patients, respectively, progress to a blast phase (BP) termed MPN-BP over a 10-year period from the time of diagnosis. Cervantes F, et al., *Acta Haematol.* 1991; 85(3):124-127. MPN-BP and de novo acute myeloid leukemia (AML) each have distinct mutational patterns and clinical courses. Rampal R, et al., *Proc Natl Acad Sci USA.* 2014; 111(50):E5401-10. Patients with MPN-BP have a particularly dismal prognosis with a median survival of less than 6 months with currently available therapies.

The present invention relates to methods of treating a myeloproliferative neoplasm in a human subject with a MDM2 inhibitor and a therapeutic agent, wherein the therapeutic agent is selected from the group consisting of a Janus kinase (JAK) inhibitor, an isocitrate dehydrogenase (IDH) inhibitor, a programmed death-1 (PD-1) inhibitor, a programmed death-ligand 1 (PD-L1) inhibitor, a programmed death-ligand 2 (PD-L2) inhibitor, an interferon, a hosphoinositide 3-kinase (PI3K) inhibitor, a protein kinase B (AKT) inhibitor, an mTOR inhibitor, a nucleoside analog, and combinations thereof.

SUMMARY OF THE INVENTION

The present invention relates to a method of treating a myeloproliferative neoplasm (MPN) comprising the step of administering to a human in need thereof, therapeutically effective amounts of a MDM2 inhibitor in combination with a therapeutic agent, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In an embodiment, the MDM2 inhibitor is a compound of Formula (I) or a compound of Formula (II):

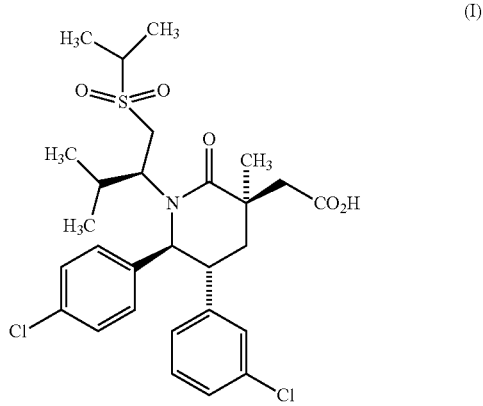

(I)

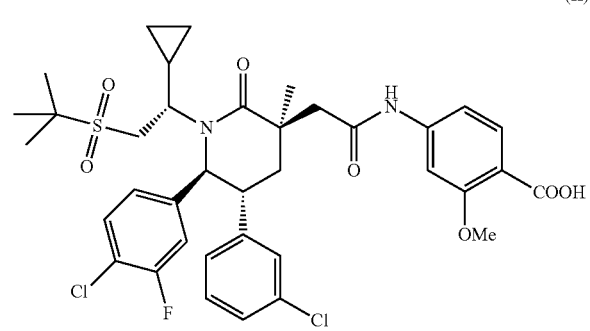

(II)

or a pharmaceutically acceptable salt thereof.

In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, R08994, Nutlin-3, Nutlin-3a, Nutlin-3b, Serdemetan, NSC59984, CHEMBL2386350, MK-8242, DS-3032, DS-3032B, RO6839921, APG-115, MI-1601, and pharmaceutically acceptable salts thereof.

In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, R06839921, APG-115, MI-1601, and pharmaceutically acceptable salts thereof.

In an embodiment, the JAK inhibitor is selected from the group consisting of AC-410, AT9283, AZ960, AZD-1480, Baricitinib, BMS-911543, CEP-33779, Cerdulatinib, CHZ868, CYT387, Decernotinib, ENMD-2076, Filgotinib, Ganetespib, INCB039110, INCB-047986, Itacitinib, JAK3-IN-1, JANEX-1, LFM-A13, LY2784544, NS-018, NSC42834, NVP-BSK805, Oclacitinib, Pacritinib, Peficitinib, Pyridone 6, R348, RGB-286638, Ruxolitinib, Ruxolitinib-S, SAR-20347, SB1317, Solcitinib, TG101209, TG101348, Tofacitinib(3R,4S), Tofacitinib(3S,4R), Tofacitinib(3S,4S), Tofacitinib, TYK2-IN-2, Upadacitinib, WHI-P154, WHI-P97, WP1066, XL019, ZM39923, and pharmaceutically acceptable salts thereof.

In an embodiment, the JAK inhibitor is selected from the group consisting of Baricitinib phosphate, CYT387 Mesylate, CYT387 sulfate salt, NS-018 hydrochloride, NS-018 maleate, NVP-BSK805 dihydrochloride, Oclacitinib maleate, Ruxolitinib phosphate, Ruxolitinib sulfate, Tofacitinib citrate, and ZM39923 hydrochloride.

In an embodiment, the PD-1 inhibitor is selected from group consisting of nivolumab, pembrolizumab, pidilizumab, AMP-224, AMP-514, PDR001, and fragments, conjugates, or variants thereof.

In an embodiment, the PD-L1 inhibitor is an anti-PD-L1 antibody. In an embodiment, the PD-L1 inhibitor is selected from the group consisting of Atezolizumab, Avelumab, Durvalumab, BMS-936559, and fragments, conjugates, or variants thereof.

In one embodiment, the anti-PD-L2 antibody is rHIgM12B7A.

In an embodiment, the AKT inhibitor is selected from the group consisting of SB0203580, MK-2206, AZD5363, Miltefosine, Perifosine, PF-04691502, CCT128930, A-674563, RX-0201, PBI-05204, AKT inhibitor VIII, AT7867, AT13148, GDC-0068, TIC10, SC79, GSK690693, GSK2110183, GSK2141795, and pharmaceutically acceptable salts thereof.

In an embodiment, the mTOR inhibitor is selected from the group consisting of Sirolimus, Everolimus, Temsirolimus, Zotarolimus, Deforolimus, Wortmannin, Ascomycin, Tacrolimus, KU-0063794, Sapanisertib, AZD8055, Vistusertib, CC-223, OSI-027, Voxtalisib, Palomid 529, PP 242, Dactolisib, BGT226, Apitolisib, Omipalisib, PF-04691502, Gedatolisib, and pharmaceutically acceptable salts thereof.

In an embodiment, the PI3K inhibitor is selected from the group consisting of Buparlisib, Alpelisib, Pictilisib, Pilaralisib, Sonolisib, Copanlisib, CH5132799, Serabelisib, AZD8186, SAR260301, GSK2636771, Idelalisib, Acalisib, Duvelisib, Taselisib, AMG319, GDC-0084, and pharmaceutically acceptable salts thereof.

In an embodiment, the IDH inhibitor is selected from the group consisting of Enasidenib, Ivosidenib, AGI-5198, AGI-6780, CHEMBL3682093, Vorasidenib, IDH-305, BAY-1436032, GSK864, (R,S)-Ivosidenib, IDH1-IN-2, IDH1-IN-1, Enasidenib mesylate, and pharmaceutically acceptable salts thereof.

In an embodiment, the interferon is selected from the group consisting of interferon alpha (IFN-α), interferon beta (IFN-β), interferon lambda (IFN-λ), interferon gamma (IFN-γ), and combinations thereof.

In an embodiment, the interferon is selected from the group consisting of interferon-alpha-2a, interferon-alpha-2b, interferon-alpha-2c, interferon-alpha-n1, interferon-alpha-n3, PEGylated interferon-alpha-2a, PEGylated interferon-alpha-2b, PEGylated interferon-alpha-2c, PEGylated interferon-alpha-n1, PEGylated interferon-alpha-n3, and combinations thereof.

In an embodiment, the interferon is selected from the group consisting of PEGylated rIFN-alpha 2b (PEG-Intron), PEGylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), albinterferon alpha-2b (Albuferon), IFN alpha-2b XL, BLX-883 (Locteron), DA-3021, AVI-005, belerofon, Cepeginterferon alfa-2b, and combinations thereof.

In an embodiment, the MPN is thrombocythemia.

In an embodiment, thrombocythemia is essential thrombocythemia (ET).

In an embodiment, the MPN is myelofibrosis.

In an embodiment, myelofibrosis is selected from primary myelofibrosis (PMF), post-polycythemia vera myelofibrosis (post-PV MF), and post-essential thrombocythemia myelofibrosis (post-ET MF).

In an embodiment, the MPN is chronic myelogenous leukemia.

In an embodiment, the MPN is systemic mastocystosis (SM).

In an embodiment, the MPN is chronic neutrophilic leukemia (CNL).

In an embodiment, the MPN is myelodysplastic syndrome (MDS).

In an embodiment, the MPN is mast cell disease (SMCD).

In an embodiment, the MPN is chronic eosinophilic leukemia.

In an embodiment, the MPN is chronic myelomonocytic leukemia (CMML).

In an embodiment, the MPN is atypical chronic myeloid leukemia (aCML).

In an embodiment, the MPN is juvenile myelomonocytic leukemia (JMVIL).

In an embodiment, the MPN is hypereosinophilic syndromes (HES).

In an embodiment, the compound of Formula (I) or Formula (II) is in a crystalline form.

In an embodiment, the crystalline form is characterized by a powder X-ray diffraction pattern comprising at least three peaks at diffraction angle 2 theta degrees selected from a group consisting of peaks at approximately 11.6, 12.4, 18.6, 19.0, 21.6 and 23.6±0.1.

In an embodiment, the compound of Formula (I) or Formula (II) is in a free form.

In an embodiment, the MDM2 inhibitor is a pharmaceutically acceptable salt of a compound of Formula (I) or Formula (II).

In an embodiment, the compound of Formula (I) or Formula (II) is in an amorphous form.

In an embodiment, the compound of Formula (I) or Formula (II) is administered once daily at a dose selected from the group consisting of 15 mg, 25 mg, 30 mg, 50 mg, 60 mg, 75 mg, 100 mg, 120 mg, 150 mg, 175 mg, 200 mg, 225 mg, 240 mg, 250 mg, 275 mg, 300 mg, 325 mg, 350 mg, 360 mg, 375 mg, and 480 mg.

In an embodiment, the compound of Formula (I) or Formula (II) is administered twice daily at a dose selected from the group consisting of 15 mg, 25 mg, 30 mg, 50 mg, 60 mg, 75 mg, 100 mg, 120 mg, 150 mg, 175 mg, 200 mg, 225 mg, 240 mg, 250 mg, 275 mg, 300 mg, 325 mg, 350 mg, 360 mg, 375 mg, and 480 mg.

In an embodiment, the human is treated with the MDM2 inhibitor for a period selected from the group consisting of about 14 days, about 21 days, about 28 days, about 35 days, about 42 days, about 49 days, and about 56 days.

In an embodiment, the compound of Formula (I) or Formula (II) is orally administered.

In an embodiment, the MDM2 inhibitor is administered before administration of the therapeutic agent, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In an embodiment, the MDM2 inhibitor is administered after administration of the therapeutic agent, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In an embodiment, the MDM2 inhibitor is administered concurrently with administration of the therapeutic agent, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In an embodiment, the therapeutically effective amount of the MDM2 inhibitor is 100 mg.

BRIEF DESCRIPTION OF THE DRAWINGS

The foregoing summary, as well as the following detailed description of the invention, will be better understood when read in conjunction with the appended drawings.

FIG. 1 illustrates XRPD Pattern of the compound of Formula (I) in a crystalline anhydrous form.

DETAILED DESCRIPTION OF THE INVENTION

While preferred embodiments of the invention are shown and described herein, such embodiments are provided by way of example only and are not intended to otherwise limit the scope of the invention. Various alternatives to the described embodiments of the invention may be employed in practicing the invention.

Unless defined otherwise, all technical and scientific terms used herein have the same meaning as is commonly understood by one of skill in the art to which this invention belongs.

The terms "administered in combination with" and "co-administration" as used herein, encompass administration of two or more active pharmaceutical ingredients to a subject so that both agents and/or their metabolites are present in the subject at the same time. Co-administration includes simultaneous administration in separate compositions, administration at different times in separate compositions, or administration in a composition in which two or more agents are present.

The term "combination" or "pharmaceutical combination" is defined herein to refer to either a fixed combination in one dosage unit form, a non-fixed combination or a kit of parts for the combined administration where the therapeutic agents may be administered together, independently at the same time or separately within time intervals, which preferably allows that the combination partners show a cooperative, e.g. synergistic effect. Thus, the single compounds of the pharmaceutical combination of the present disclosure could be administered simultaneously or sequentially.

Furthermore, the pharmaceutical combination of the present disclosure may be in the form of a fixed combination or in the form of a non-fixed combination.

The term "effective amount" or "therapeutically effective amount" refers to that amount of an active pharmaceutical ingredient or combination of active pharmaceutical ingredients as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, and other factors which can readily be determined by one of ordinary skill in the art. The term also applies to a dose that will induce a particular response in target cells, (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

The terms "enantiomerically enriched," "enantiomerically pure," and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, such as at least 80% by weight. In some embodiments, the enrichment can be significantly greater than 80% by weight, providing a "substantially enantiomerically enriched," "substantially enantiomerically pure," or a "substantially non-racemic" preparation, which refers to preparations of compositions which have at least 85% by weight of one enantiomer relative to the other enantiomer, such as at least 90% by weight, and such as at least 95% by weight. The terms "diastereomerically enriched" and "diastereomerically pure," as used herein, refer to compositions in which the percent by weight of one diastereomer is greater than the amount of that one diastereomer in a control mixture of diastereomers. In some embodiments, the enrichment can be significantly greater than 80% by weight, providing a "substantially diastereomerically enriched" or "substantially diastereomerically pure" preparation, which refers to preparations of compositions which have at least 85% by weight of one diastereomer relative to other diastereomers, such as at least 90% by weight, and such as at least 95% by weight.

In some embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or some enantiomers can be prepared by asymmetric syntheses. See, for example, Jacques, *Enantiomers, Racemates and Resolutions*, Wiley Interscience, New York (1981); E. L. Eliel and S. H. Wilen, *Stereochemistry of Organic Compounds*, Wiley-Interscience, New York (1994).

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)- and 20% (R)-, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or the Pirkle alcohol, or derivatization of a compounds using a chiral compound such as Mosher's acid followed by chromatography or nuclear magnetic resonance spectroscopy.

The term "fixed combination" means that the therapeutic agents, e.g., the single compounds of the combination, are in the form of a single entity or dosage form.

The term "$IC_{50}$" refers to the half maximal inhibitory concentration, i.e. inhibition of 50% of the desired activity. The term "$EC_{50}$" refers to the drug concentration at which one-half the maximum response is achieved.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

In an embodiment, compounds described herein include of the isomers, stereoisomers, and enantiomers thereof.

"MPN-BP" refers to blast phase (BP) of the myeloproliferative neoplasms (MPN) described in this disclosure.

The term "non-fixed combination" means that the therapeutic agents, e.g., the single compounds of the combination, are administered to a patient as separate entities or dosage forms either simultaneously or sequentially with no specific time limits, wherein preferably such administration provides therapeutically effective levels of the two therapeutic agents in the body of the subject, e.g., a mammal or human in need thereof.

"Pharmaceutically acceptable carrier" or "pharmaceutically acceptable excipient" is intended to include any and all solvents, dispersion media, coatings, antibacterial and antifungal agents, isotonic, and absorption delaying agents. The use of such media and agents for active pharmaceutical ingredients is well known in the art. Except insofar as any conventional media or agent is incompatible with the active pharmaceutical ingredient, its use in the therapeutic compositions of the invention is contemplated. Supplementary active ingredients can also be incorporated into the described compositions. Unless otherwise specified, or clearly indicated by the text, reference to therapeutic agents useful in the pharmaceutical combination of the present disclosure includes both the free base of the compounds, and all pharmaceutically acceptable salts of the compounds.

The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In selected embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve proton transfer between the cocrystal and the drug, and instead involves intermolecular interactions, such as hydrogen bonding, aromatic ring stacking, or dispersive forces, between the cocrystal former and the drug in the crystal structure.

The terms "QD," "qd," or "q.d." means quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quarter in die, four times a day, or four times daily.

"Solvate" refers to a compound in physical association with one or more molecules of a pharmaceutically acceptable solvent.

A "therapeutic effect" as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

Compounds of the invention also include crystalline and amorphous forms, including, for example, polymorphs, pseudopolymorphs, solvates, hydrates, unsolvated polymorphs (including anhydrates), conformational polymorphs, and amorphous forms of the compounds, as well as combinations thereof "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as combinations thereof, unless a particular crystalline or amorphous form is referred to.

Co-Administration of Compounds

The present invention relates to pharmaceutical combinations or pharmaceutical compositions that are particularly useful as a medicine. Specifically, the combinations or compositions of the present disclosure can be applied in the treatment of a cancer. In an embodiment, the cancer is a MPN. The present invention also relates to use of pharmaceutical combinations or pharmaceutical compositions of the present disclosure for the preparation of a medicament for the treatment of a cancer, in particular a MPN, and to a method for treating cancer in a subject in need thereof comprising administering to the subject a therapeutically effective amount of a pharmaceutical combination according to the present disclosure, or the pharmaceutical composition according to the present disclosure.

In an embodiment, the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD).

In an embodiment, the myelofibrosis is selected from the group consisting of primary myelofibrosis (PMF), post-polycythemia vera myelofibrosis (post-PV MF), and post-essential thrombocythemia myelofibrosis (post-ET MF).

In an embodiment, the primary myelofibrosis (PMF) is selected from the group consisting of prefibrotic/early stage PMF and overt fibrotic stage PMF.

In an embodiment, the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T).

An embodiment of the invention is a composition, such as a pharmaceutical composition comprising a combination comprising a MDM2 inhibitor in combination with a therapeutic agent, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. Another embodiment is a kit containing both components formulated into separate pharmaceutical compositions, which are formulated for co-administration.

Another embodiment of the invention is a method of for treating a myeloproliferative neoplasm (MPN), wherein the MPN is selected from the group consisting of polycythemia vera (PV), myelofibrosis, thrombocythemia, idiopathic myelofibrosis, chronic myelogenous leukemia, systemic mastocystosis (SM), chronic neutrophilic leukemia (CNL), myelodysplastic syndrome (MDS), and systemic mast cell disease (SMCD) in a subject, comprising co-administering to the subject in need thereof a therapeutically effective amount of a combination comprising a MDM2 inhibitor in combination with a therapeutic agent, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. The pharmaceutical composition comprising the combination, and the kit, are both for use in treating such disease or condition.

In an embodiment, the MDM2 inhibitor is a compound of Formula (I) or Formula (II).

In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, R08994, Nutlin-3, Nutlin-3a, Nutlin-3b, Serdemetan, NSC59984, CHEMBL2386350, MK-8242, DS-3032, DS-3032B, RO6839921, APG-115, MI-1601, and pharmaceutically acceptable salts thereof.

In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, R06839921, APG-115, MI-1601, and pharmaceutically acceptable salts thereof.

In an embodiment, the JAK inhibitor is a JAK1 inhibitor.
In an embodiment, the JAK inhibitor is a JAK2 inhibitor.
In an embodiment, the JAK inhibitor is a JAK3 inhibitor.
In an embodiment, the JAK inhibitor is a selective JAK inhibitor.
In an embodiment, the JAK inhibitor is a pan JAK inhibitor.
In an embodiment, the JAK inhibitor is selected from the group consisting of AC-410, AT9283, AZ960, AZD-1480, Baricitinib, BMS-911543, CEP-33779, Cerdulatinib, CHZ868, CYT387, Decernotinib, ENMD-2076, Filgotinib, Ganetespib, INCB039110, INCB-047986, Itacitinib, JAK3-

IN-1, JANEX-1, LFM-A13, LY2784544, NS-018, NSC42834, NVP-BSK805, Oclacitinib, Pacritinib, Peficitinib, Pyridone 6, R348, RGB-286638, Ruxolitinib, Ruxolitinib-S, SAR-20347, SB1317, Solcitinib, TG101209, TG101348, Tofacitinib(3R,4S), Tofacitinib(3S,4R), Tofacitinib(3S,4S), Tofacitinib, TYK2-IN-2, Upadacitinib, WHI-P154, WHI-P97, WP1066, XL019, ZM39923, and pharmaceutically acceptable salts thereof.

In an embodiment, the JAK inhibitor is selected from the group consisting of Baricitinib phosphate, CYT387 Mesylate, CYT387 sulfate salt, NS-018 hydrochloride, NS-018 maleate, NVP-BSK805 dihydrochloride, Oclacitinib maleate, Ruxolitinib phosphate, Ruxolitinib sulfate, Tofacitinib citrate, and ZM39923 hydrochloride.

In an embodiment, the PD-1 inhibitor is selected from group consisting of nivolumab, pembrolizumab, pidilizumab, AMP-224, AMP-514, PDR001, and fragments, conjugates, or variants thereof.

In an embodiment, the PD-L1 inhibitor is an anti-PD-L1 antibody. In an embodiment, the PD-L1 inhibitor is selected from the group consisting of Atezolizumab, Avelumab, Durvalumab, BMS-936559, and fragments, conjugates, or variants thereof.

In an embodiment, the anti-PD-L2 antibody is rHIgM12B7A.

In an embodiment, the AKT inhibitor is selected from the group consisting of SB0203580, MK-2206, AZD5363, Miltefosine, Perifosine, PF-04691502, CCT128930, A-674563, RX-0201, PBI-05204, AKT inhibitor VIII, AT7867, AT13148, GDC-0068, TIC10, SC79, GSK690693, GSK2110183, GSK2141795, and pharmaceutically acceptable salts thereof.

In an embodiment, the mTOR inhibitor is selected from the group consisting of Sirolimus, Everolimus, Temsirolimus, Zotarolimus, Deforolimus, Wortmannin, Ascomycin, Tacrolimus, KU-0063794, Sapanisertib, AZD8055, Vistusertib, CC-223, OSI-027, Voxtalisib, Palomid 529, PP 242, Dactolisib, BGT226, Apitolisib, Omipalisib, PF-04691502, Gedatolisib, and pharmaceutically acceptable salts thereof.

In an embodiment, the PI3K inhibitor is selected from the group consisting of Buparlisib, Alpelisib, Pictilisib, Pilaralisib, Sonolisib, Copanlisib, CH5132799, Serabelisib, AZD8186, SAR260301, GSK2636771, Idelalisib, Acalisib, Duvelisib, Taselisib, AMG319, GDC-0084, and pharmaceutically acceptable salts thereof.

In an embodiment, the IDH inhibitor is selected from the group consisting of Enasidenib, Ivosidenib, AGI-5198, AGI-6780, CHEMBL3682093, Vorasidenib, IDH-305, BAY-1436032, GSK864, (R,S)-Ivosidenib, IDH1-IN-2, IDH1-IN-1, Enasidenib mesylate, and pharmaceutically acceptable salts thereof.

In an embodiment, the interferon is selected from the group consisting of interferon alpha (IFN-α), interferon beta (IFN-β), interferon lambda (IFN-λ), interferon gamma (IFN-γ), and combinations thereof.

In an embodiment, the interferon is selected from the group consisting of interferon-alpha-2a, interferon-alpha-2b, interferon-alpha-2c, interferon-alpha-n1, interferon-alpha-n3, PEGylated interferon-alpha-2a, PEGylated interferon-alpha-2b, PEGylated interferon-alpha-2c, PEGylated interferon-alpha-n1, PEGylated interferon-alpha-n3, and combinations thereof.

In an embodiment, the interferon is selected from the group consisting of PEGylated rIFN-alpha 2b (PEG-Intron), PEGylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), albinterferon alpha-2b (Albuferon), IFN alpha-2b XL, BLX-883 (Locteron), DA-3021, AVI-005, belerofon, Cepeginterferon alfa-2b, and combinations thereof.

In an embodiment, the nucleoside analog is selected from the group consisting of decitabine, cytarabine, azacitidine, zebularine, and pharmaceutically acceptable salts thereof.

The combination may be administered by any route known in the art. In an exemplary embodiment, the MDM2 inhibitor and the therapeutic agent are independently administered by oral, intravenous, intramuscular, intraperitoneal, subcutaneous or transdermal means, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. In one embodiment, the MDM2 inhibitor is administered orally.

In an exemplary embodiment, the MDM2 inhibitor is in the form of a pharmaceutically acceptable salt.

In an exemplary embodiment, the MDM2 inhibitor is administered to the subject before administration of the therapeutic agent, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In an exemplary embodiment, the MDM2 inhibitor is administered to the subject after administration of the therapeutic agent, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In an exemplary embodiment, the MDM2 inhibitor is administered to the subject concurrently with administration of the therapeutic agent, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In an embodiment, the disclosure provides a method of for treating a blast phase myeloproliferative neoplasm (MPN-BP) in a subject, comprising co-administering to the subject in need thereof a therapeutically effective amount of a combination comprising a MDM2 inhibitor in combination with a therapeutic agent, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. The pharmaceutical composition comprising the combination, and the kit, are both for use in treating such disease or condition. In an embodiment, the MPN-BP is selected from the group consisting of blast phase polycythemia vera (BP-PV), blast phase myelofibrosis, blast phase primary myelofibrosis, blast phase thrombocythemia, blast phase essential thrombocythemia (BP-ET), blast phase idiopathic myelofibrosis, blast phase systemic mastocystosis (BP-SM), blast phase chronic neutrophilic leukemia (BP-CNL), blast phase myelodysplastic syndrome (BP-MDS), and blast phase systemic mast cell disease (BP-SMCD). In an embodiment, the blast phase myelofibrosis is selected from the group consisting of blast phase primary myelofibrosis (BP-PMF), blast phase post-polycythemia vera myelofibrosis (BP-post-PV MF), and blast phase post-essential thrombocythemia myelofibrosis (BP-post-ET MF). In an embodiment, the blast phase primary myelofibrosis (BP-PMF) is selected from the group consisting of blast phase prefibrotic/early stage PMF and blast phase overt fibrotic stage PMF. In an embodiment, the MPN-BP is selected from the group consisting of blast phase chronic neutrophilic leukemia (BP-CNL), blast phase chronic eosinophilic leukemia, blast phase chronic myelomonocytic leukemia (BP-CMML), blast phase atypical chronic myeloid leukemia (BP-aCML), blast phase juvenile myelomonocytic leukemia (BP-JMML), blast phase hypereosinophilic syndromes (BP-HES), and blast phase myelodysplastic/myeloproliferative neoplasms with ring sideroblasts and thrombocytosis (BP-MDS/MPN-RS-T). In an embodiment, the MDM2 inhibitor is a compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, R08994, Nutlin-3, Nutlin-3a, Nutlin-3b, Serdemetan, NSC59984, CHEMBL2386350, MK-8242, DS-3032, DS-3032B, RO6839921, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, R06839921, APG-115, MI-1601, and pharmaceutically acceptable salts thereof.

In an embodiment, the disclosure provides a method of for treating a blast phase myeloproliferative neoplasm (MPN-BP) in a subject, comprising co-administering to the subject in need thereof a therapeutically effective amount of a combination comprising the compound of Formula (I) in combination with a nucleoside analog, wherein the nucleoside analog is selected from the group consisting of decitabine, cytarabine, azacitidine, zebularine, and pharmaceutically acceptable salts thereof.

In an embodiment, the disclosure provides a method of for treating a blast phase myeloproliferative neoplasm (MPN-BP) in a subject, comprising co-administering to the subject in need thereof a therapeutically effective amount of a combination comprising the compound of Formula (I) in combination with decitabine or a pharmaceutically acceptable salt thereof.

In an embodiment, the disclosure provides a method of for treating a blast phase myeloproliferative neoplasm (MPN-BP) in a subject, comprising co-administering to the subject in need thereof a therapeutically effective amount of a combination comprising the compound of Formula (I) in combination with cytarabine or a pharmaceutically acceptable salt thereof.

In an embodiment, the MPN in the human subject is characterized by a CALR mutation (calreticulin, located on chromosome 19p13.2), as described in Massie, N. Engl. J. Med. 2013, 25: 2379-2390 and incorporated by reference herein in its entirety.

In an embodiment, the MPN in the human subject is characterized by an MPL mutation (myeloproliferative leukemia virus oncogene; located on chromosome 1p34), as described in Pikman, Plos Med. 2006; 3(7): e270 and incorporated by reference herein in its entirety.

In an embodiment, the MPN in the human subject is characterized by a JAK2V617F mutation. The JAK2V617F mutation is a functional mutation promoting cytokine-independent growth of myeloid cells and accounts for a majority of myeloproliferative neoplasms (MPN), as described in Nakatake, Oncogene, 2012, 31, 1323-1333 and incorporated by reference herein in its entirety.

In an embodiment, the MIPN in the human subject is characterized by having one or more mutations selected from the group consisting of JAK2V617F, MIPL, CALR, and combinations thereof.

In an exemplary embodiment, the subject is a mammal, such as a human.

MIDM2 Inhibitor

The compound of Formula (I) has the structure and name shown below.

2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl) acetic acid

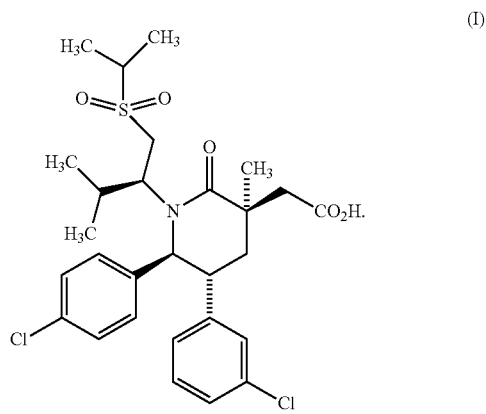

The synthesis of the compound of Formula (I) is set forth in International Applications: WO2011/153509 and WO2014/200937; U.S. Pat. Nos. 8,569,341; 9,593,129; 9,296,736; 9,623,018; 9,757,367; 9,801,867; 9,376,386; and 9,855,259, the disclosure of which are incorporated by reference herein in its entirety.

In an embodiment, the compound of Formula (I) or Formula (II) is in an amorphous form. In an embodiment, the MDM2 inhibitor is the compound of Formula (I) or Formula (II) in a crystalline form. In an embodiment, the MDM2 inhibitor is the compound of Formula (I) in a crystalline anhydrous form. In an embodiment, the MDM2 inhibitor is the compound of Formula (I) in a crystalline anhydrous form characterized by a powder X-ray diffraction pattern comprising peaks at diffraction angle 2 theta degrees at approximately 11.6, 12.4, 18.6, 19.0, 21.6 and 23.6. In an embodiment, the MDM2 inhibitor is the compound of Formula (I) in a crystalline anhydrous form having the X-ray diffraction pattern substantially shown in FIG. 1. The method of making such crystalline form was disclosed in the International Application WO2014200937, the disclosure of which is incorporated herein by reference in its entirety.

In an embodiment, the MDM2 inhibitor is a compound of Formula (II) having the structure and name shown below.

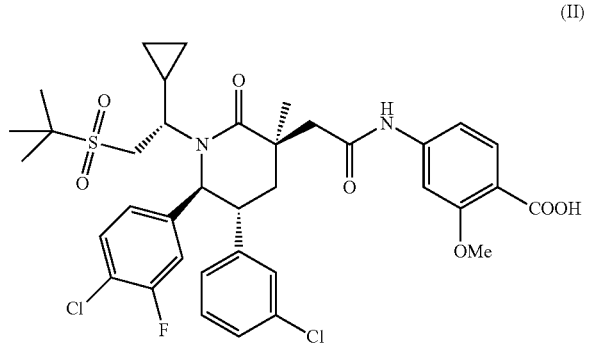 [SMILES: COc1cc(NC(=O)C[C@@]2(C)C[C@H](c3cccc(Cl)c3)[C@@H](c3ccc(Cl)c(F)c3)N([C@H](CS(=O)(=O)C(C)(C)C)C3CC3)C2=O)ccc1C(=O)O]

(II)

4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid The synthesis of the compound of Formula (II) is set forth in U.S. Pat. No. 8,952,036, the disclosure of which is incorporated by reference herein in its entirety.

RG7388 (Idasanutlin)

In an embodiment, the MDM2 inhibitor is RG7388. RG7388 has the chemical structure and name shown as:

4-[[(2R,3S,4R,5S)-3-(3-chloro-2-fluorophenyl)-4-(4-chloro-2-fluorophenyl)-4-cyano-5-(2,2-dimethylpropyl)pyrrolidine-2-carbonyl]amino]-3-methoxybenzoic acid

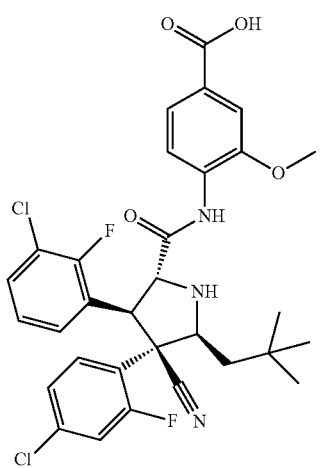 [SMILES: COc1cc(C(=O)O)ccc1NC(=O)[C@@H]1N[C@@H](CC(C)(C)C)[C@](C#N)(c2ccc(Cl)cc2F)[C@H]1c1cccc(Cl)c1F]

Triptolide (PG490)

In an embodiment, the MDM2 inhibitor is triptolide. Triptolide has the chemical structure and name shown as:

(5bS,6aS,7aS,8R,8aR,9aS,9bS,10aS,10bS)-8-hydroxy-8a-isopropyl-10b-methyl-2,5,5b,6,6a,8,8a,9a,9b,10b-decahydrotris(oxireno) [2',3':4b,5;2",3":6,7;2''',3''':8a,9]phenanthro[1,2-c]furan-3(1H)-one

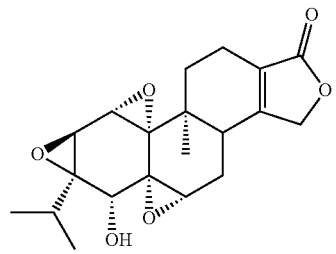

Nutlin-3a

In an embodiment, the MDM2 inhibitor is Nutlin-3a. Nutlin-3a has the chemical structure and name shown as:

4-[(4S,5R)-4,5-bis(4-chlorophenyl)-2-(4-methoxy-2-propan-2-yloxyphenyl)-4,5-dihydroimidazole-1-carbonyl]piperazin-2-one

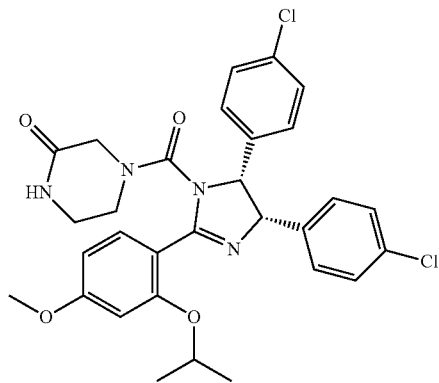 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

HDM201

In an embodiment, the MDM2 inhibitor is HDM201. HDM201 has the chemical structure and name shown as:

(4S)-5-(5-chloro-1-methyl-2-oxopyridin-3-yl)-4-(4-chlorophenyl)-2-(2,4-dimethoxypyrimidin-5-yl)-3-propan-2-yl-4H-pyrrolo[3,4-d]imidazol-6-one

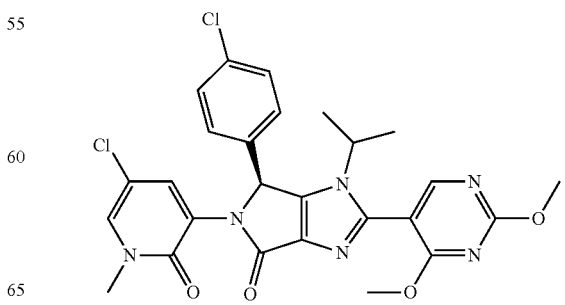

RG7112

In an embodiment, the MDM2 inhibitor is RG7112. RG7112 has the chemical structure and name shown as:

[(4S,5R)-2-(4-tert-butyl-2-ethoxyphenyl)-4,5-bis(4-chlorophenyl)-4,5-dimethylimidazol-1-yl]-[4-(3-methylsulfonylpropyl)piperazin-1-yl]methanone

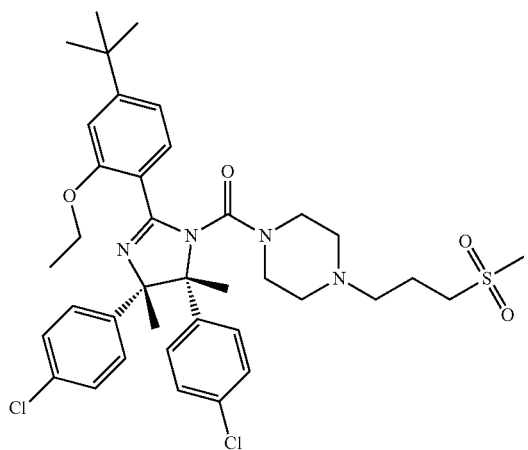 [SMILES: CCOc1cc(C(C)(C)C)ccc1C1=N[C@@](C)(c2ccc(Cl)cc2)[C@@](C)(c2ccc(Cl)cc2)N1C(=O)N1CCN(CCCS(C)(=O)=O)CC1]

CGM097A

In an embodiment, the MDM2 inhibitor is CGM097A. CGM097A has the chemical structure and name shown as:

(1S)-1-(4-chlorophenyl)-6-methoxy-2-[4-[methyl-[[4-(4-methyl-3-oxopiperazin-1-yl)cyclohexyl]methyl]amino]phenyl]-7-propan-2-yloxy-1,4-dihydroisoquinolin-3-one

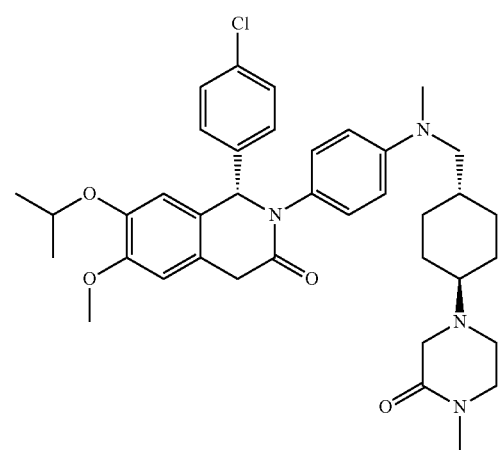 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2]

Nutlin-3

In an embodiment, the MDM2 inhibitor is nutlin-3. Nutlin-3 has the chemical structure and name shown as:

4-[4,5-bis(4-chlorophenyl)-2-(4-methoxy-2-propan-2-yloxyphenyl)-4,5-dihydroimidazole-1-carbonyl]piperazin-2-one

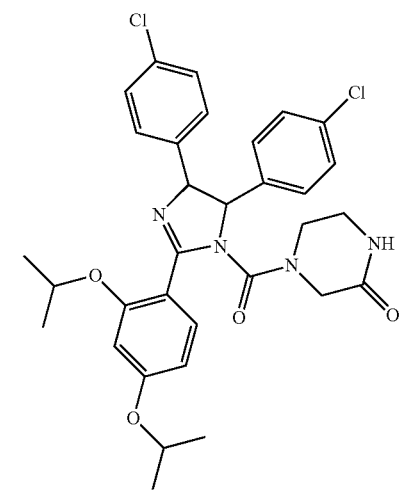 [SMILES: CC(C)Oc1ccc(C2=NC(c3ccc(Cl)cc3)C(c3ccc(Cl)cc3)N2C(=O)N2CCNC(=O)C2)c(OC(C)C)c1]

SJ-172550

In an embodiment, the MDM2 inhibitor is SJ-172550. SJ-172550 has the chemical structure and name shown as:

methyl 2-[2-chloro-6-ethoxy-4-[(3-methyl-5-oxo-1-phenylpyrazol-4-ylidene)methyl]phenoxy]acetate

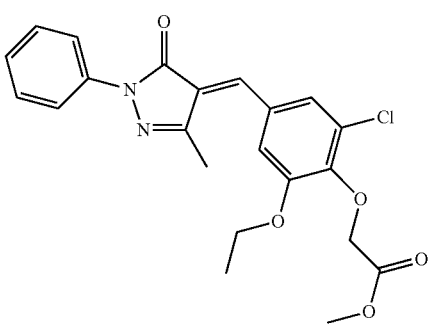 [SMILES: CCOc1cc(/C=C2/C(=O)N(c3ccccc3)N=C2C)cc(Cl)c1OCC(=O)OC]

SAR405838 (MI-77301)

In an embodiment, the MDM2 inhibitor is SAR405838. SAR405838 has the chemical structure and name shown as:

(2'R,3R,3'S,5'S)-6-chloro-3'-(3-chloro-2-fluorophenyl)-5'-(2,2-dimethylpropyl)-N-(4-hydroxycyclohexyl)-2-oxospiro[1H-indole-3,4'-pyrrolidine]-2'-carboxamide

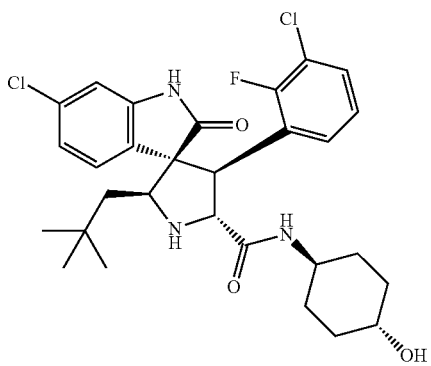 [SMILES: CC(C)(C)C[C@@H]1N[C@@H](C(=O)N[C@H]2CC[C@H](O)CC2)[C@H](c2cccc(Cl)c2F)[C@]12C(=O)Nc1cc(Cl)ccc12]

MI-773

In an embodiment, the MDM2 inhibitor is MI-773. MI-773 has the chemical structure and name shown as:

(2'R,3S,3'S,5'R)-6-chloro-3'-(3-chloro-2-fluorophenyl)-5'-(2,2-dimethylpropyl)-N-(4-hydroxycyclohexyl)-2-oxospiro[1H-indole-3,4'-pyrrolidine]-2'-carboxamide

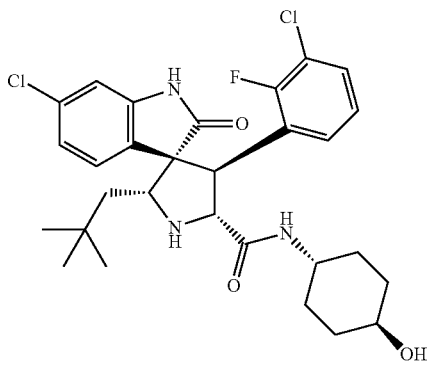 [SMILES: CC(C)(C)C[C@H]1N[C@@H](C(=O)N[C@H]2CC[C@H](O)CC2)[C@H](c2cccc(Cl)c2F)[C@@]12C(=O)Nc1cc(Cl)ccc12]

MX69

In an embodiment, the MDM2 inhibitor is MX69. MX69 has the chemical structure and name shown as:

4-[8-[(3,4-dimethylphenyl)sulfamoyl]-3a,4,5,9b-tetrahydro-3H-cyclopenta[c]quinolin-4-yl]benzoic acid

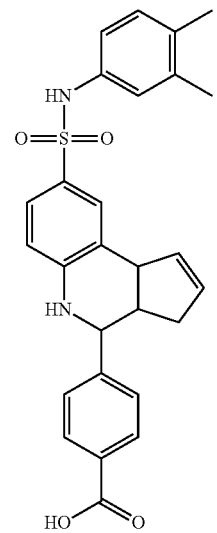 [SMILES: Cc1ccc(NS(=O)(=O)c2ccc3c(c2)C2C=CCC2C(c2ccc(C(=O)O)cc2)N3)cc1C]

YH239-EE

In an embodiment, the MDM2 inhibitor is YH239-EE. YH239-EE has the chemical structure and name shown as:

ethyl 3-[2-(tert-butylamino)-1-[(4-chlorophenyl)methyl-formylamino]-2-oxoethyl]-6-chloro-1H-indole-2-carboxylate

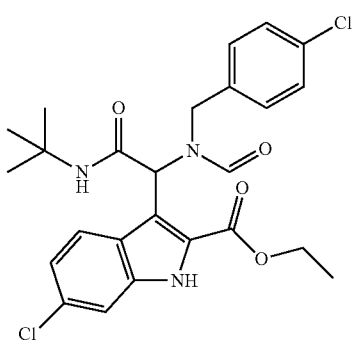 [SMILES: CCOC(=O)c1[nH]c2cc(Cl)ccc2c1C(C(=O)NC(C)(C)C)N(C=O)Cc1ccc(Cl)cc1]

RO8994

In an embodiment, the MDM2 inhibitor is RO8994. RO8994 has the chemical structure and name shown as:

(2'R,3R,3'S,5'S)—N-(4-carbamoyl-2-methoxyphenyl)-6-chloro-3'-(3-chloro-2-fluorophenyl)-5'-(2,2-dimethylpropyl)-2-oxospiro[1H-indole-3,4'-pyrrolidine]-2'-carboxamide

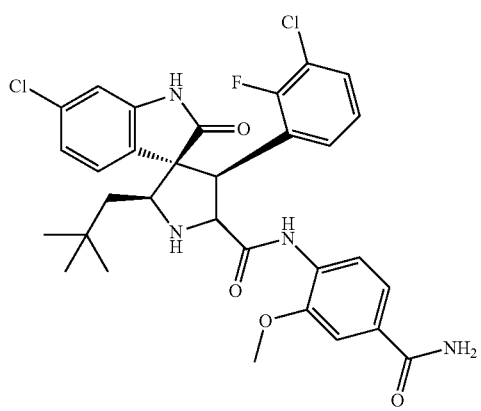 [SMILES: COc1cc(C(N)=O)ccc1NC(=O)C1N[C@@H](CC(C)(C)C)[C@@]2(C(=O)Nc3cc(Cl)ccc32)[C@H]1c1cccc(Cl)c1F]

Nutlin-3b

In an embodiment, the MDM2 inhibitor is nutlin-3b. Nutlin-3b has the chemical structure and name shown as:

4-[(4R,5S)-4,5-bis(4-chlorophenyl)-2-(4-methoxy-2-propan-2-yloxyphenyl)-4,5-dihydroimidazole-1-carbonyl]piperazin-2-one

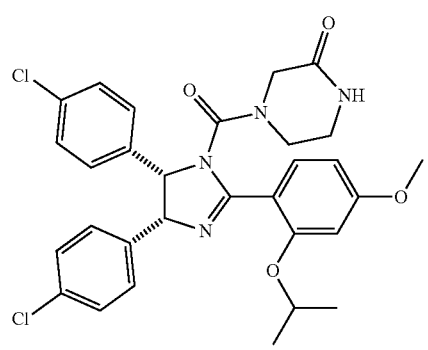 [SMILES: COc1ccc(C2=N[C@H](c3ccc(Cl)cc3)[C@H](c3ccc(Cl)cc3)N2C(=O)N2CCNC(=O)C2)c(OC(C)C)c1]

Serdemetan (JNJ-26854165)

In an embodiment, the MDM2 inhibitor is Serdemetan. Serdemetan has the chemical structure and name shown as:

1-N-[2-(1H-indol-3-yl)ethyl]-4-N-pyridin-4-ylbenzene-1,4-diamine

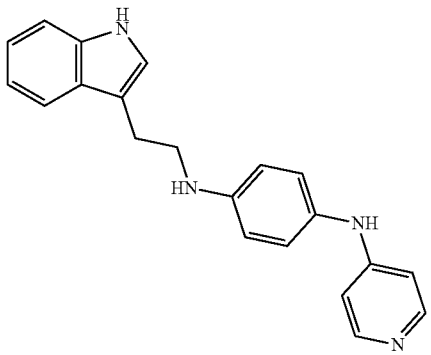 [SMILES: c1ccc2c(CCNc3ccc(Nc4ccncc4)cc3)c[nH]c2c1]

NSC59984

In an embodiment, the MDM2 inhibitor is NSC59984. NSC59984 has the chemical structure and name shown as:

(E)-1-(4-methylpiperazin-1-yl)-3-(5-nitrofuran-2-yl)prop-2-en-1-one

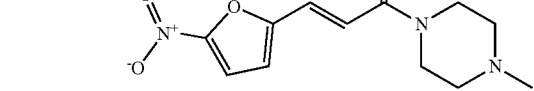

CHEMBL2386350

In an embodiment, the MDM2 inhibitor is CHEMBL2386350. CHEMBL2386350 has the chemical structure and name shown as:

2-[4-[(4S,5R)-2-(4-tert-butyl-2-ethoxyphenyl)-4,5-bis(4-chlorophenyl)-4,5-dimethylimidazole-1-carbonyl]piperazin-1-yl]-1-morpholin-4-ylethanone

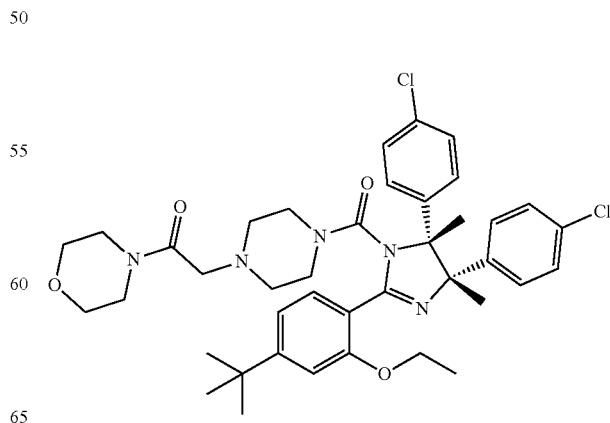

CGM0970B

In an embodiment, the MDM2 inhibitor is CGM0970B. CGM0970B has the chemical structure and name shown as:

(1R)-1-(4-chlorophenyl)-6-methoxy-2-[4-[methyl-[[4-(4-methyl-3-oxopiperazin-1-yl)cyclohexyl]methyl]amino]phenyl]-7-propan-2-yloxy-1,4-dihydroisoquinolin-3-one

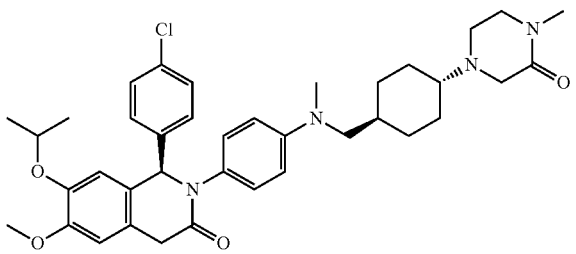 [SMILES: COc1cc2c(cc1OC(C)C)[C@@H](c1ccc(Cl)cc1)N(c1ccc(N(C)C[C@H]3CC[C@H](N4CCN(C)C(=O)C4)CC3)cc1)C(=O)C2]

MK-8242

In an embodiment, the MDM2 inhibitor is MK-8242. MK-8242 has the chemical structure and name shown as:

4-amino-1-[(2R,3S,4S,5R)-3,4-dihydroxy-5-(hydroxymethyl)oxolan-2-yl]pyrimidin-2-one

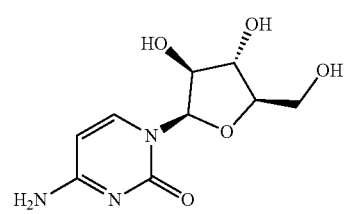 [SMILES: Nc1ccn([C@@H]2O[C@H](CO)[C@@H](O)[C@@H]2O)c(=O)n1]

DS-3032

In an embodiment, the MDM2 inhibitor is DS-3032. DS-3032 has the chemical structure and name shown as:

(3'R,4'S,5'R)—N-((3R,6S)-6-carbamoyltetrahydro-2H-pyran-3-yl)-6"-chloro-4'-(2-chloro-3-fluoropyridin-4-yl)-4,4-dimethyl-2"-oxodispiro[cyclohexane-1,2'-pyrrolidine-3',3'"-indoline]-5'-carboxamide

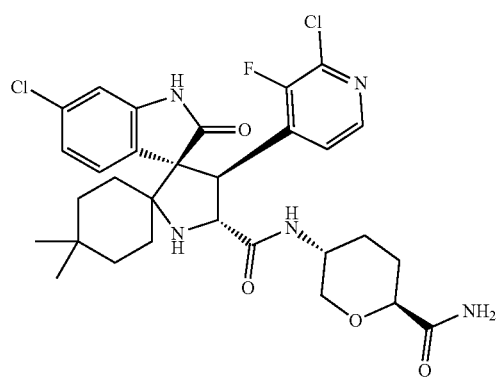

DS-3032B

In an embodiment, the MDM2 inhibitor is DS-3032B. DS-3032B has the chemical structure and name shown as:

(3'R,4'S,5'R)—N-((3R,6S)-6-carbamoyltetrahydro-2H-pyran-3-yl)-6"-chloro-4'-(2-chloro-3-fluoropyridin-4-yl)-4,4-dimethyl-2"-oxodispiro[cyclohexane-1,2'-pyrrolidine-3',3'"-indoline]-5'-carboxamide 4-methylbenzenesulfonate

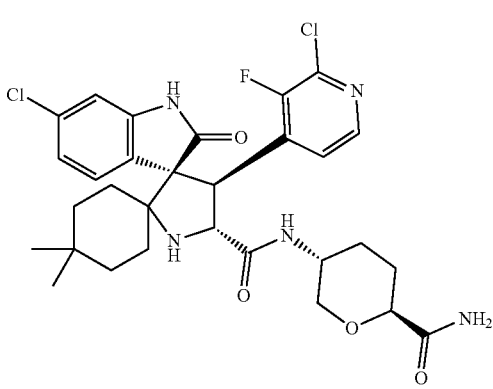 [SMILES: CC1(C)CCC2(CC1)N[C@@H](C(=O)N[C@@H]1CC[C@@H](C(N)=O)OC1)[C@H](c1ccnc(Cl)c1F)[C@]21C(=O)Nc2cc(Cl)ccc21]

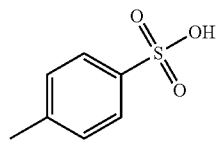

HDM201

In an embodiment, the MDM2 inhibitor is HDM201. HDM201 has the chemical structure and name shown as:

(4S)-5-(5-chloro-1-methyl-2-oxopyridin-3-yl)-4-(4-chlorophenyl)-2-(2,4-dimethoxypyrimidin-5-yl)-3-propan-2-yl-4H-pyrrolo[3,4-d]imidazol-6-one

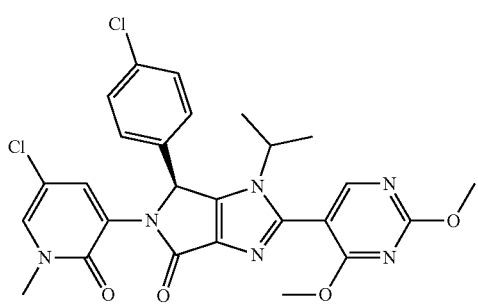 [SMILES: COc1ncc(-c2nc3c(n2C(C)C)[C@H](c2ccc(Cl)cc2)N(c2cc(Cl)cn(C)c2=O)C3=O)c(OC)n1]

APG-115

In an embodiment, the MDM2 inhibitor is APG-115. APG-115 has the chemical structure and name shown as:

4-((3'R,4'S,5'R)-6"-Chloro-4'-(3-chloro-2-fluorophenyl)-1'-ethyl-2"-oxodispiro[cyclohexane-1,2'-pyrrolidine-3',3"-indoline]-5'-carboxamido)bicyclo[2.2.2]octane-1-carboxylic Acid

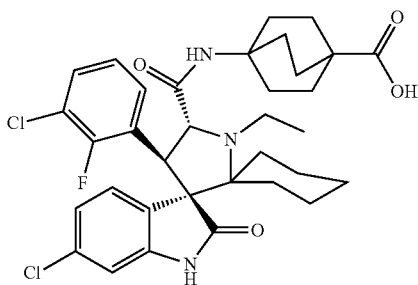 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

MI-1061

In an embodiment, the MDM2 inhibitor is APG-115. APG-115 has the chemical structure and name shown as:

4-((3'R,4'S,5'R)-6"-chloro-4'-(3-chloro-2-fluorophenyl)-2"-oxodispiro[cyclohexane-1,2'-pyrrolidine-3',3"-indoline]-5'-carboxamido)benzoic acid

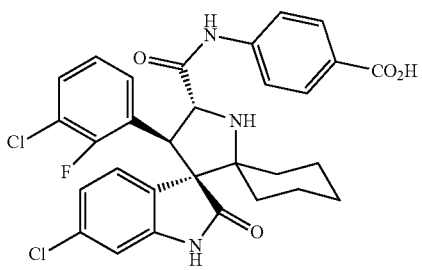 [SMILES: O=C(O)c1ccc(NC(=O)[C@@H]2NC3(CCCCC3)[C@@]3(C(=O)Nc4cc(Cl)ccc43)[C@H]2c2cccc(Cl)c2F)cc1]

JAK Inhibitor
Ruxolitinib

In an embodiment, the JAK inhibitor is Ruxolitinib (available from Incyte Corp. and Novartis AG). Ruxolitinib has the chemical structure and name shown as: (R)-3-(4-(7H-pyrrolo[2,3-d]pyrimidin-4-yl)-1H-pyrazol-1-yl)-3-cyclopentylpropanenitrile,

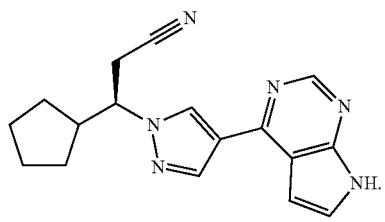 [SMILES: N#CC[C@H](C1CCCC1)n1cc(-c2ncnc3[nH]ccc23)cn1]

The preparation of this compound is described in U.S. Pat. Nos. 8,604,043, 7,834,022, 8,486,902, 8,530,485, 7,598,257, 8,541,425, and 8,410,265 the disclosures of which are incorporated by reference herein. In an embodiment, the JAK inhibitor is a compound selected from the structures disclosed in U.S. Pat. Nos. 8,604,043, 7,834,022, 8,486,902, 8,530,485, 7,598,257, 8,541,425, and 8,410,265, the disclosures of which are incorporated by reference herein.

In an embodiment, the JAK inhibitor is Ruxolitinib phosphate (available from Incyte Corp. and Novartis AG). In an embodiment, the JAK inhibitor is the phosphate salt of (R)-3-(4-(7H-pyrrolo[2,3-d]pyrimidin-4-yl)-1H-pyrazol-1-yl)-3-cyclopentylpropanenitrile.

Baricitinib

In an embodiment, the JAK inhibitor is Baricitinib (available from Incyte Corp. and Eli Lilly & Co.). Baricitinib has the chemical structure and name shown as: 2-(3-(4-(7H-pyrrolo[2,3-d]pyrimidin-4-yl)-1H-pyrazol-1-yl)-1-(ethylsulfonyl)azetidin-3-yl)acetonitrile

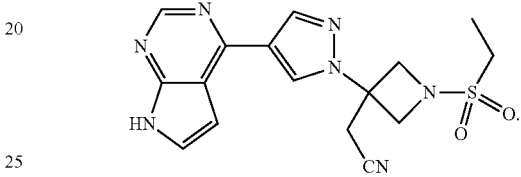

The preparation of this compound is described in U.S. Pat. Nos. 8,158,616 and 8,420,629, the disclosures of which are incorporated by reference herein. In an embodiment, the JAK inhibitor is a compound described in U.S. Pat. Nos. 8,158,616 and 8,420,629, the disclosures of which are incorporated by reference herein.

Momelotinib

In an embodiment, the JAK inhibitor is Momelotinib (Gilead Sciences). Momelotinib is also known as CYT-387. Momelotinib has the chemical structure and name shown as: N-(cyanomethyl)-4-(2-((4-morpholinophenyl)amino)pyrimidin-4-yl)benzamide

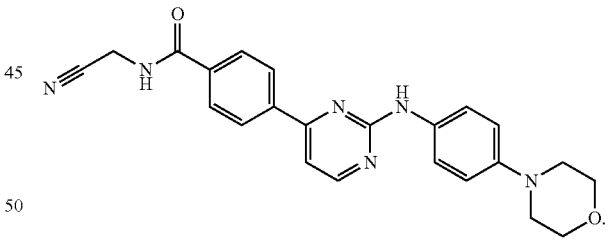

The preparation of this compound is described in U.S. Pat. No. 8,486,941, the disclosure of which is incorporated by reference herein. In an embodiment, the JAK inhibitor is a compound described in U.S. Pat. No. 8,486,941, the disclosure of which is incorporated by reference herein.

Ganetespib

In an embodiment, the JAK inhibitor is Ganetespib. Ganetespib has the chemical structure and name shown as: 5-(2,4-dihydroxy-5-isopropylphenyl)-4-(1-methyl-1H-indol-5-yl)-2,4-dihydro-3H-1,2,4-triazol-3-one

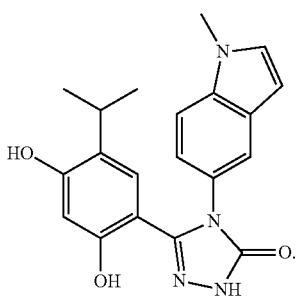 [SMILES: CC(C)c1cc(-c2n[nH]c(=O)n2-c2ccc3c(ccn3C)c2)c(O)cc1O]

The preparation of this compound is described in U.S. Pat. Nos. 7,825,148 and 8,628,752, the disclosures of which are incorporated by reference herein. In an embodiment, the JAK inhibitor is a compound described in U.S. Pat. Nos. 7,825,148 and 8,628,752, the disclosures of which are incorporated by reference herein.

NS-018

In an embodiment, the JAK inhibitor is NS-018. NS-018 has the chemical structure and name shown as: (S)—$N^2$-(1-(4-fluorophenyl)ethyl)-6-(1-methyl-1H-pyrazol-4-yl)-$N^4$-(pyrazin-2-yl)pyrimidine-2,4-diamine

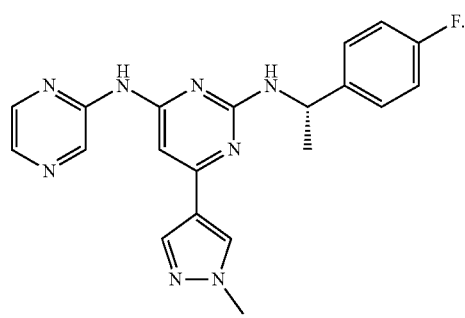 [SMILES: C[C@H](Nc1nc(Nc2cnccn2)cc(-c2cnn(C)c2)n1)c1ccc(F)cc1]

The preparation of this compound is described in U.S. Pat. Nos. 8,673,891 and 8,586,591, the disclosures of which are incorporated by reference herein. In an embodiment, the JAK inhibitor is a compound described in U.S. Pat. Nos. 8,673,891 and 8,586,591, the disclosures of which are incorporated by reference herein.

BMS-911543

In an embodiment, the JAK inhibitor is BMS-911543. BMS-911543 has the chemical structure and name shown as: N,N-dicyclopropyl-4-((1,5-dimethyl-1H-pyrazol-3-yl)amino)-6-ethyl-1-methyl-1,6-dihydroimidazo[4,5-d]pyrrolo[2,3-b]pyridine-7-carboxamide

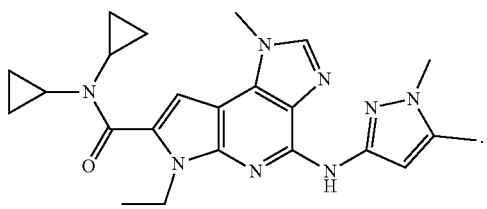 [SMILES: CCn1c(C(=O)N(C2CC2)C2CC2)cc2c3c(ncn3C)c(Nc3cc(C)n(C)n3)nc21]

The preparation of this compound is described in U.S. Pat. Nos. 8,673,933 and 8,202,881, the disclosures of which are incorporated by reference herein. In an embodiment, the JAK inhibitor is a compound described in U.S. Pat. Nos. 8,673,933 and 8,202,881, the disclosures of which are incorporated by reference herein.

Gandotinib (LY2784544)

In an embodiment, the JAK inhibitor is Gandotinib. Gandotinib has the chemical structure and name shown as: 3-(4-chloro-2-fluorobenzyl)-2-methyl-N-(5-methyl-1H-pyrazol-3-yl)-8-(morpholinomethyl)imidazo[1,2-b]pyridazin-6-amine

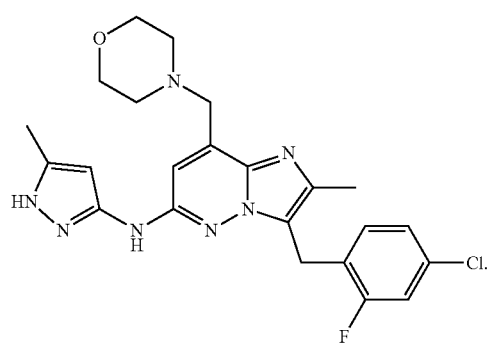 [SMILES: Cc1cc(Nc2cc(CN3CCOCC3)c3nc(C)c(Cc4ccc(Cl)cc4F)n3n2)n[nH]1]

The preparation of this compound is described in U.S. Pat. No. 7,897,600, the disclosure of which is incorporated by reference herein. In an embodiment, the JAK inhibitor is a compound described in U.S. Pat. No. 7,897,600, the disclosure of which is incorporated by reference herein.

ENMD-2076

In an embodiment, the JAK inhibitor is ENMD-2076. ENMD-2076 has the chemical structure and name shown as: (E)-N-(5-methyl-1H-pyrazol-3-yl)-6-(4-methylpiperazin-1-yl)-2-styrylpyrimidin-4-amine

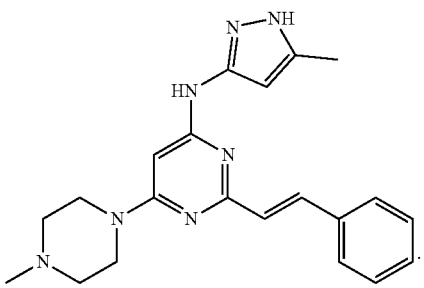 [SMILES: Cc1cc(Nc2cc(N3CCN(C)CC3)nc(/C=C/c3ccccc3)n2)n[nH]1]

The preparation of this compound is described in U.S. Pat. Nos. 8,153,630; 7,563,787 and 8,114,870, the disclosures of which are incorporated by reference herein. In an embodiment, the JAK inhibitor is a compound described in U.S. Pat. Nos. 8,153,630; 7,563,787 and 8,114,870, the disclosures of which are incorporated by reference herein.

AT-9283

In an embodiment, the JAK inhibitor is AT-9283. AT-9283 has the chemical structure and name shown as: 1-cyclopropyl-3-(3-(5-(morpholinomethyl)-1H-benzo[d]imidazol-2-yl)-1H-pyrazol-4-yl)urea

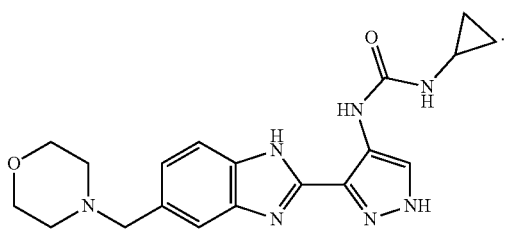 [SMILES: O=C(Nc1c[nH]nc1-c1nc2cc(CN3CCOCC3)ccc2[nH]1)NC1CC1]

The preparation of this compound is described in U.S. Pat. Nos. 8,399,442 and 7,977,477, the disclosures of which are incorporated by reference herein. In an embodiment, the JAK inhibitor is a compound described in U.S. Pat. Nos. 8,399,442 and 7,977,477, the disclosures of which are incorporated by reference herein.

Pacritinib

In an embodiment, the JAK inhibitor is Pacritinib. Pacritinib has the chemical structure and name shown as: 11-(2-pyrrolidin-1-yl-ethoxy)-14,19-dioxa-5,7,26-triaza-tetracyclo[19.3.1.1(2,6).1(8,12)]heptacosa-1(25),2(26),3,5,8,10,12(27),16,21,23-decaene

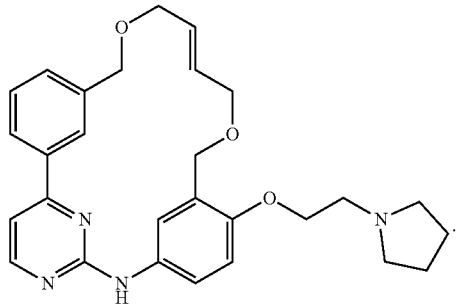 [SMILES: C1=C/COCc2cc(ccc2OCCN2CCCC2)Nc2nccc(n2)-c2cccc(c2)COC/1]

In an embodiment, the structure of Pacritinib may be a tautomeric form. The preparation of Pacritinib is described in U.S. Pat. Nos. 8,143,255; 8,153,632 and 8,415,338, the disclosures of which are incorporated by reference herein.

AC-410

In an embodiment, the JAK inhibitor is AC-410 (available from Ambit Biosciences). AC-410 has the chemical structure and name shown as: (S)-(4-fluorophenyl)(4-((5-methyl-1H-pyrazol-3-yl)amino)quinazolin-2-yl)methanol

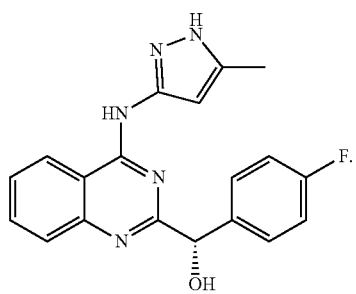 [SMILES: Cc1cc(Nc2nc([C@@H](O)c3ccc(F)cc3)nc3ccccc23)n[nH]1]

The preparation of racemic (4-fluorophenyl)(4-((5-methyl-1H-pyrazol-3-yl)amino)quinazolin-2-yl)methanol hydrochloride is described in Examples 3 and 12 of U.S. Pat. No. 8,349,851, the disclosure of which is incorporated by reference herein.

AZD-1480

In an embodiment, the JAK inhibitor is AZD-1480. AZD-1480 has the chemical structure and name shown as: (S)-5-chloro-$N^2$-(1-(5-fluoropyrimidin-2-yl)ethyl)-$N^4$-(5-methyl-1H-pyrazol-3-yl)pyrimidine-2,4-diamine

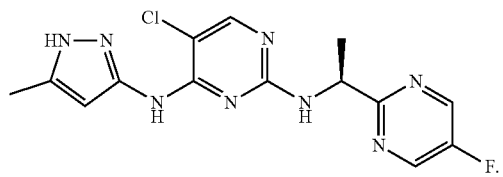 [SMILES: Cc1cc(Nc2nc(N[C@@H](C)c3ncc(F)cn3)ncc2Cl)n[nH]1]

The preparation of this compound is described in U.S. Pat. No. 8,088,784, the disclosure of which is incorporated by reference herein. In an embodiment, the JAK inhibitor is selected from the compounds described in U.S. Pat. No. 8,088,784, the disclosure of which is incorporated by reference herein.

CYT387

In an embodiment, the JAK inhibitor is CYT387. CYT387 has the chemical structure and name shown as: N-(cyanomethyl)-4-(2-(4-morpholinophenylamino)pyrimidin-4-yl)benzamide

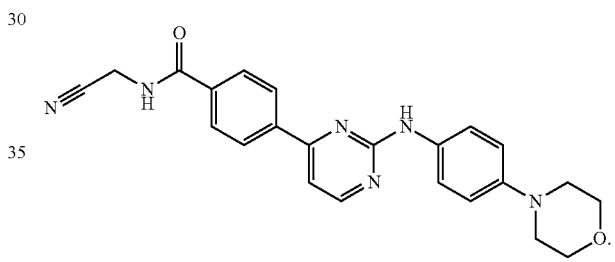

The preparation of this compound is described in U.S. Pat. Nos. 9,809,559 and 8,486,941, the disclosures of which are incorporated by reference herein.

TYK2-IN-2

In an embodiment, the JAK inhibitor is TYK2-IN-2. TYK2-IN-2 has the chemical structure and name shown as: 6-((3,5-dimethylphenyl)amino)-8-(methylamino)imidazo[1,2-b]pyridazine-3-carboxamide

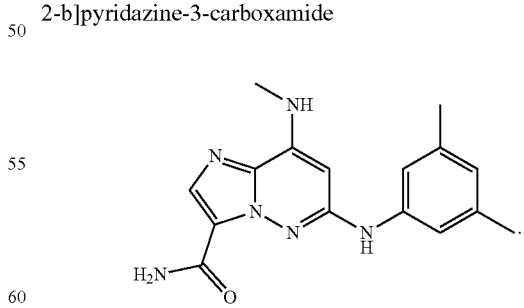

SAR-20347

In an embodiment, the JAK inhibitor is SAR-20347. SAR-20347 has the chemical structure and name shown as: 2-(2-chloro-6-fluorophenyl)-5-[4-(morpholine-4-carbonyl)anilino]-1,3-oxazole-4-carboxamide

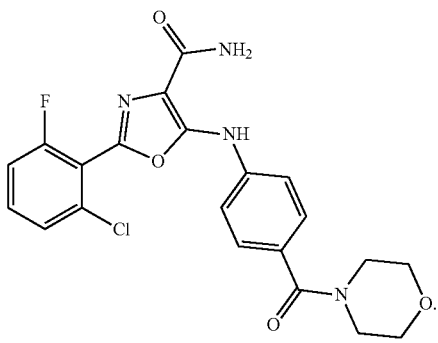 [SMILES: NC(=O)c1nc(-c2c(F)cccc2Cl)oc1Nc1ccc(C(=O)N2CCOCC2)cc1]

Upadacitinib (ABT-494)

In an embodiment, the JAK inhibitor is Upadacitinib (ABT-494). Upadacitinib has the chemical structure and name shown as: (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide

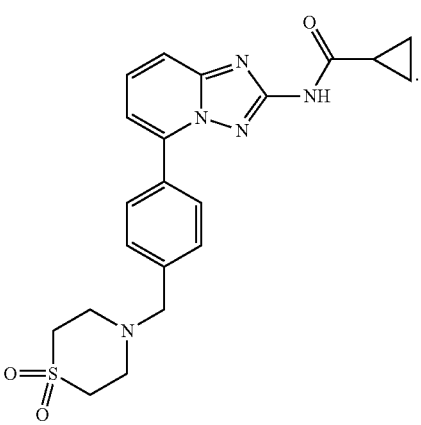

TG101348 (Fedratinib; SAR 302503)

In an embodiment, the JAK inhibitor is TG101348 (Fedratinib; SAR 302503). TG101348 has the chemical structure and name shown as: N-tert-butyl-3-[[5-methyl-2-[4-(2-pyrrolidin-1-ylethoxy)anilino]pyrimidin-4-yl]amino]benzenesulfonamide

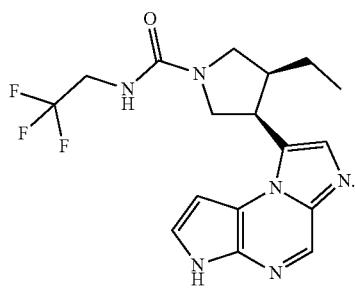 [SMILES: CC[C@@H]1CN(C(=O)NCC(F)(F)F)C[C@@H]1c1cnc2cnc3[nH]ccc3n12]

WP1066

In an embodiment, the JAK inhibitor is WP1066. WP1066 has the chemical structure and name shown as: (E)-3-(6-bromopyridin-2-yl)-2-cyano-N-[(1S)-1-phenylethyl]prop-2-enamide

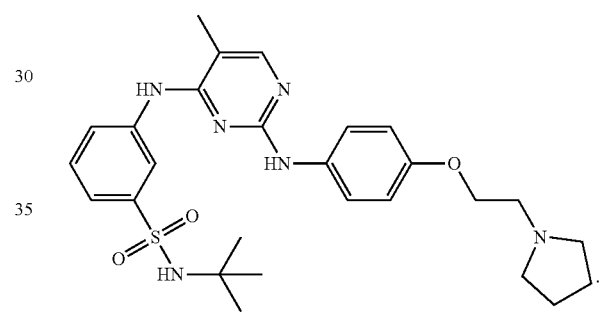

Cerdulatinib (PRT062070; PRT2070)

In an embodiment, the JAK inhibitor is Cerdulatinib (PRT062070; PRT2070). Cerdulatinib has the chemical structure and name shown as: 4-(cyclopropylamino)-2-[4-(4-ethylsulfonylpiperazin-1-yl)anilino]pyrimidine-5-carboxamide

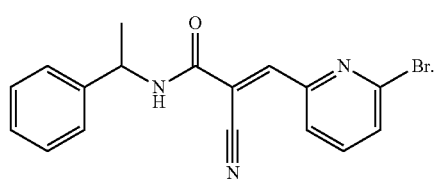 [SMILES: CC(NC(=O)/C(C#N)=C/c1cccc(Br)n1)c1ccccc1]

GLPG0634 (Filgotinib)

In an embodiment, the JAK inhibitor is GLPG0634 (Filgotinib). GLPG0634 has the chemical structure and name shown as: N-[5-[4-[(1,1-dioxo-1,4-thiazinan-4-yl)methyl]phenyl]-[1,2,4]triazolo[1,5-a]pyridin-2-yl]cyclopropanecarboxamide

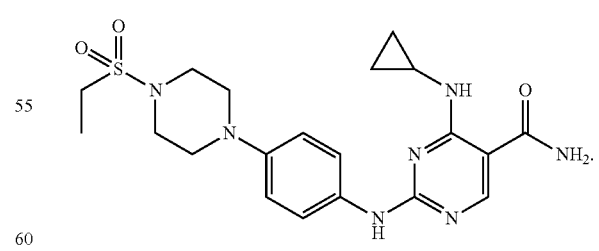

Tofacitinib

In an embodiment, the JAK inhibitor is Tofacitinib. Tofacitinib has the chemical structure and name shown as: 3-[(3R,4R)-4-methyl-3-[methyl(7H-pyrrolo[2,3-d]pyrimidin-4-yl)amino]piperidin-1-yl]-3-oxopropanenitrile

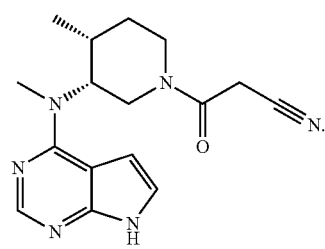 [SMILES: C[C@@H]1CCN(C(=O)CC#N)C[C@@H]1N(C)c1ncnc2[nH]ccc12]

Itacitinib

In an embodiment, the JAK inhibitor is Itacitinib. Itacitinib has the chemical structure and name shown as: 2-[1-[1-[3-fluoro-2-(trifluoromethyl)pyridine-4-carbonyl]piperidin-4-yl]-3-[4-(7H-pyrrolo[2,3-d]pyrimidin-4-yl)pyrazol-1-yl]azetidin-3-yl]acetonitrile

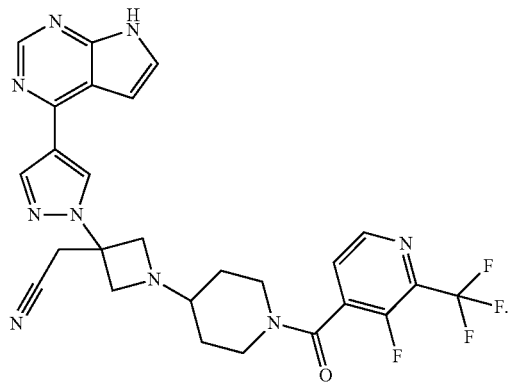 [SMILES: N#CCC1(n2cc(-c3ncnc4[nH]ccc34)cn2)CN(C2CCN(C(=O)c3ccnc(C(F)(F)F)c3F)CC2)C1]

Decernotinib

In an embodiment, the JAK inhibitor is Decernotinib. Decernotinib has the chemical structure and name shown as: (2R)-2-methyl-2-[[2-(1H-pyrrolo[2,3-b]pyridin-3-yl)pyrimidin-4-yl]amino]-N-(2,2,2-trifluoroethyl)butanamide

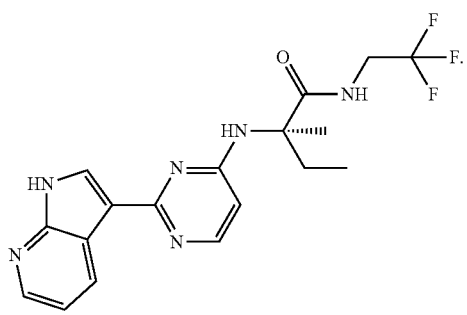 [SMILES: CC[C@@](C)(Nc1ccnc(-c2c[nH]c3ncccc23)n1)C(=O)NCC(F)(F)F]

CHZ868

In an embodiment, the JAK inhibitor is CHZ868. CHZ868 has the chemical structure and name shown as: N-[4-[2-(2,4-difluoroanilino)-1,4-dimethylbenzimidazol-5-yl]oxypyridin-2-yl]acetamide

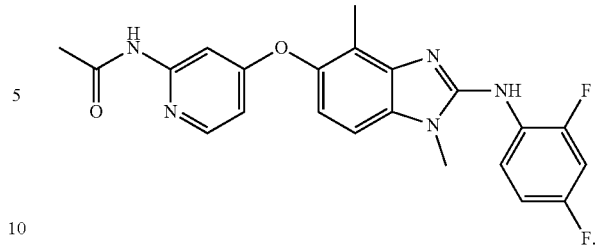

SB1317

In an embodiment, the JAK inhibitor is SB1317. SB1317 has the chemical structure and name shown as: (E)-6-methyl-12-oxa-3,6-diaza-2(4,2)-pyrimidina-1,4(1,3)-dibenzenacyclododecaphan-8-ene

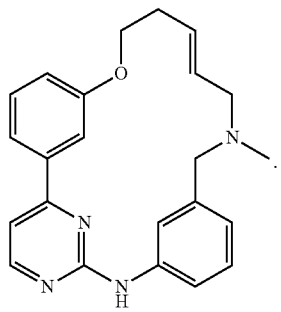 [SMILES: CN1C/C=C/CCOc2cccc(c2)-c2ccnc(n2)Nc2cccc(c2)C1]

Solcitinib

In an embodiment, the JAK inhibitor is Solcitinib. Solcitinib has the chemical structure and name shown as: N-[5-[4-(3,3-dimethylazetidine-1-carbonyl)phenyl]-[1,2,4]triazolo[1,5-a]pyridin-2-yl]cyclopropanecarboxamide

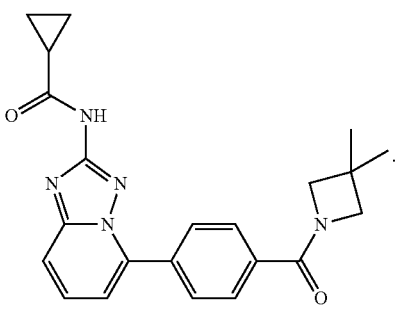 [SMILES: CC1(C)CN(C(=O)c2ccc(-c3cccc4nc(NC(=O)C5CC5)nn34)cc2)C1]

Peficitinib

In an embodiment, the JAK inhibitor is Peficitinib. Peficitinib has the chemical structure and name shown as: 4-[[(1R,3S)-5-hydroxy-2-adamantyl]amino]-1H-pyrrolo[2,3-b]pyridine-5-carboxamide

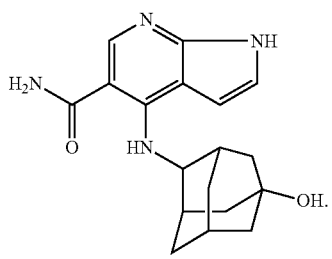 [SMILES: NC(=O)c1cnc2[nH]ccc2c1NC1C2CC3CC1CC(O)(C3)C2]

CEP-33779

In an embodiment, the JAK inhibitor is CEP-33779. CEP-33779 has the chemical structure and name shown as: N-[3-(4-methylpiperazin-1-yl)phenyl]-8-(4-methylsulfonylphenyl)-[1,2,4]triazolo[1,5-a]pyridin-2-amine

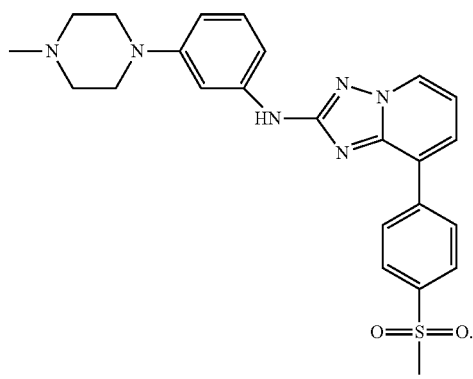 [SMILES: CN1CCN(c2cccc(Nc3nc4c(-c5ccc(S(C)(=O)=O)cc5)cccn4n3)c2)CC1]

Pyridone 6

In an embodiment, the JAK inhibitor is Pyridone 6. Pyridone 6 has the chemical structure and name shown as: 2-(tert-butyl)-9-fluoro-3H-benzo[h]imidazo[4,5-f]isoquinolin-7-ol

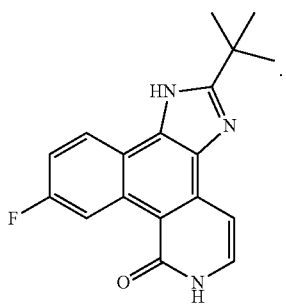 [SMILES: CC(C)(C)c1nc2c3cc[nH]c(=O)c3c3cc(F)ccc3c2[nH]1]

LFM-A13

In an embodiment, the JAK inhibitor is LFM-A13. LFM-A13 has the chemical structure and name shown as: (Z)-2-cyano-N-(2,5-dibromophenyl)-3-hydroxybut-2-enamide

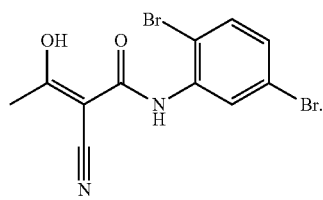 [SMILES: C/C(O)=C(\C#N)C(=O)Nc1cc(Br)ccc1Br]

BMS-911543

In an embodiment, the JAK inhibitor is BMS-911543. BMS-911543 has the chemical structure and name shown as: (Z)—N,N-dicyclopropyl-4-((1,5-dimethyl-1,2-dihydro-3H-pyrazol-3-ylidene)amino)-6-ethyl-1-methyl-1,6-dihydro-imidazo[4,5-d]pyrrolo[2,3-b]pyridine-7-carboxamide

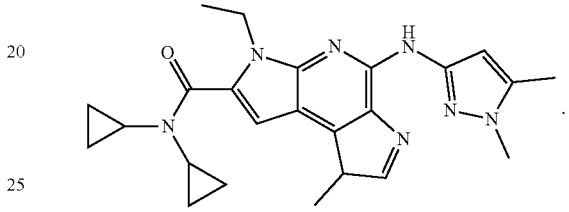

NS-018

In an embodiment, the JAK inhibitor is NS-018. NS-018 has the chemical structure and name shown as: 6-N-[(1S)-1-(4-fluorophenyl)ethyl]-4-(1-methylpyrazol-4-yl)-2-N-pyrazin-2-ylpyridine-2,6-diamine

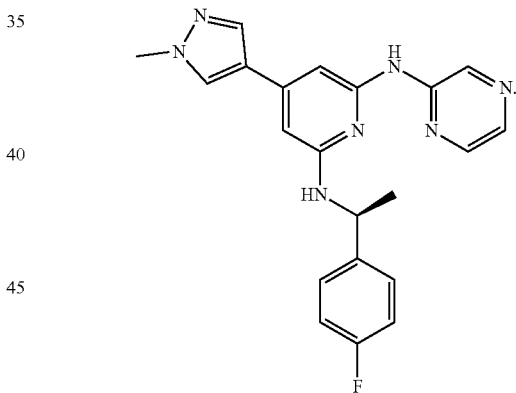

JANEX-1

In an embodiment, the JAK inhibitor is JANEX-1. JANEX-1 has the chemical structure and name shown as: 4-[(6,7-dimethoxyquinazolin-4-yl)amino]phenol

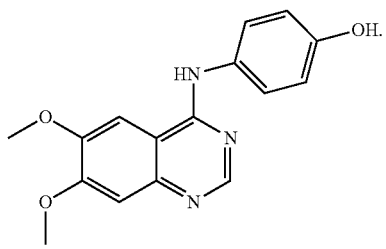 [SMILES: COc1cc2ncnc(Nc3ccc(O)cc3)c2cc1OC]

TG101209

In an embodiment, the JAK inhibitor is TG101209. TG101209 has the chemical structure and name shown as: N-tert-butyl-3-[[5-methyl-2-[4-(4-methylpiperazin-1-yl)anilino]pyrimidin-4-yl]amino]benzenesulfonamide

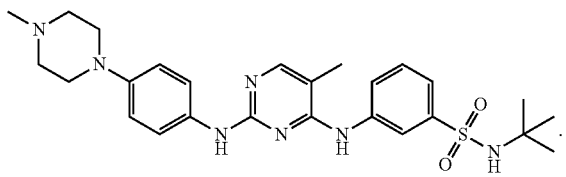 [SMILES: Cc1cnc(Nc2ccc(N3CCN(C)CC3)cc2)nc1Nc1cccc(S(=O)(=O)NC(C)(C)C)c1]

WHI-P154

In an embodiment, the JAK inhibitor is WHI-P154. WHI-P154 has the chemical structure and name shown as: 2-bromo-4-[(6,7-dimethoxyquinazolin-4-yl)amino]phenol

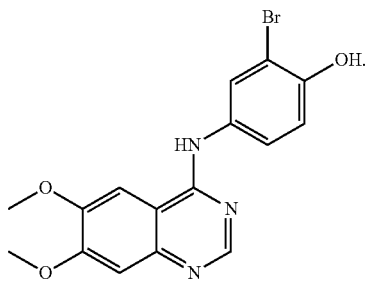 [SMILES: COc1cc2ncnc(Nc3ccc(O)c(Br)c3)c2cc1OC]

NVP-BSK805

In an embodiment, the JAK inhibitor is NVP-BSK805. NVP-BSK805 has the chemical structure and name shown as: 4-[[2,6-difluoro-4-[3-(1-piperidin-4-ylpyrazol-4-yl)quinoxalin-5-yl]phenyl]methyl]morpholine

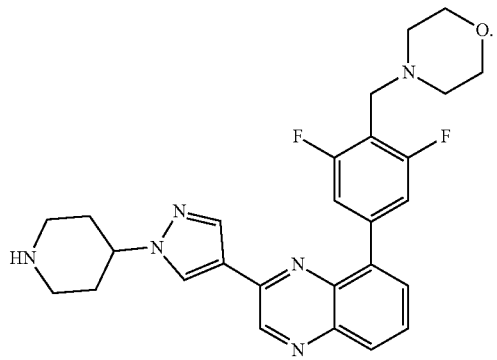 [SMILES: Fc1cc(-c2cccc3ncc(-c4cnn(C5CCNCC5)c4)nc23)cc(F)c1CN1CCOCC1]

ZM39923

In an embodiment, the JAK inhibitor is ZM39923. ZM39923 has the chemical structure and name shown as: 3-[benzyl(propan-2-yl)amino]-1-naphthalen-2-ylpropan-1-one

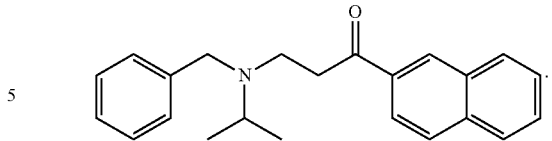

Ruxolitinib-S

In an embodiment, the JAK inhibitor is Ruxolitinib-S. Ruxolitinib-S has the chemical structure and name shown as: (3S)-3-cyclopentyl-3-[4-(7H-pyrrolo[2,3-d]pyrimidin-4-yl)pyrazol-1-yl]propanenitrile

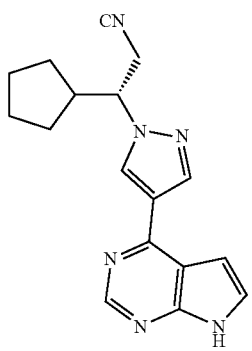

XL019

In an embodiment, the JAK inhibitor is XL019. XL019 has the chemical structure and name shown as: (2S)—N-[4-[2-(4-morpholin-4-ylanilino)pyrimidin-4-yl]phenyl]pyrrolidine-2-carboxamide

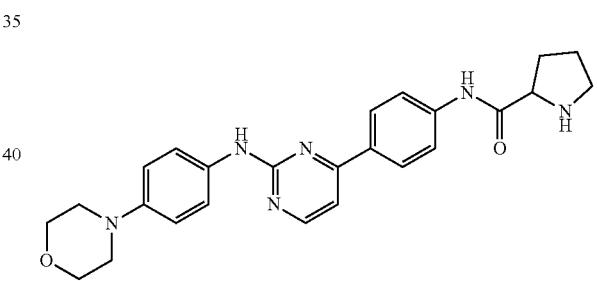

AZ960

In an embodiment, the JAK inhibitor is AZ960. AZ960 has the chemical structure and name shown as: 5-fluoro-2-[[(1S)-1-(4-fluorophenyl)ethyl]amino]-6-[(5-methyl-1H-pyrazol-3-yl)amino]pyridine-3-carbonitrile

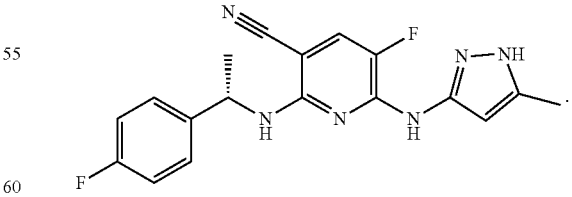

JAK3-IN-1

In an embodiment, the JAK inhibitor is JAK3-IN-1. JAK3-IN-1 has the chemical structure and name shown as: N-[3-[[[5-chloro-2-[2-methoxy-4-(4-methylpiperazin-1-yl)anilino]pyrimidin-4-yl]amino]methyl]phenyl]prop-2-enamide

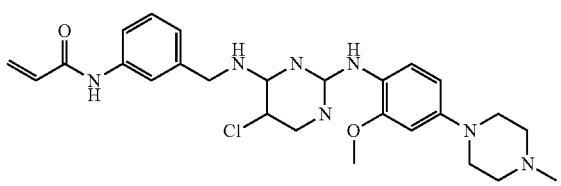

WHI-P97

In an embodiment, the JAK inhibitor is WHI-P97. WHI-P97 has the chemical structure and name shown as: 2,6-dibromo-4-[(6,7-dimethoxyquinazolin-4-yl)amino]phenol

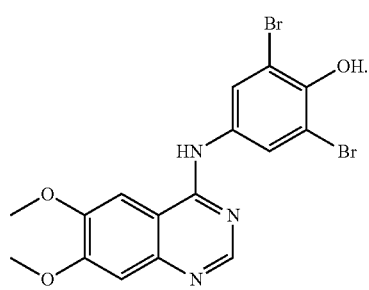 [SMILES: COc1cc2ncnc(Nc3cc(Br)c(O)c(Br)c3)c2cc1OC]

RGB-286638

In an embodiment, the JAK inhibitor is RGB-286638. RGB-286638 has the chemical structure and name shown as: 1-[3-[4-[[4-(2-methoxyethyl)piperazin-1-yl]methyl]phenyl]-4-oxo-1H-indeno[1,2-c]pyrazol-5-yl]-3-morpholin-4-ylurea;dihydrochloride

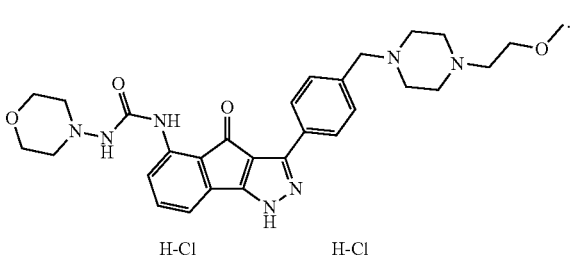

Tofacitinib(3R,4S)

In an embodiment, the JAK inhibitor is Tofacitinib(3R,4S). Tofacitinib(3R,4S) has the chemical structure and name shown as: 3-[(3R,4S)-4-methyl-3-[methyl(7H-pyrrolo[2,3-d]pyrimidin-4-yl)amino]piperidin-1-yl]-3-oxopropanenitrile

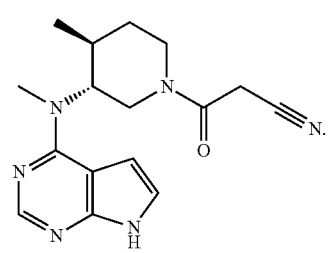 [SMILES: C[C@H]1CCN(C(=O)CC#N)C[C@@H]1N(C)c1ncnc2[nH]ccc12]

NSC42834

In an embodiment, the JAK inhibitor is NSC42834. NSC42834 has the chemical structure and name shown as: 2-methyl-1-phenyl-4-pyridin-2-yl-2-(2-pyridin-2-ylethyl)butan-1-one

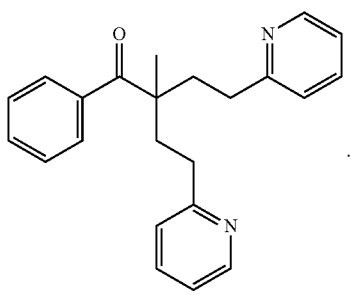 [SMILES: CC(CCc1ccccn1)(CCc1ccccn1)C(=O)c1ccccc1]

PF-06651600

In an embodiment, the JAK inhibitor is PF-06651600. PF-06651600 has the chemical structure and name shown as: benzyl 2-(hydroxymethyl)-5-[(2-methylpropan-2-yl)oxycarbonylamino]piperidine-1-carboxylate

Tofacitinib(3S,4S)

In an embodiment, the JAK inhibitor is Tofacitinib(3S,4S). Tofacitinib(3S,4S) has the chemical structure and name shown as: 3-[(3S,4S)-4-methyl-3-[methyl(7H-pyrrolo[2,3-d]pyrimidin-4-yl)amino]piperidin-1-yl]-3-oxopropanenitrile

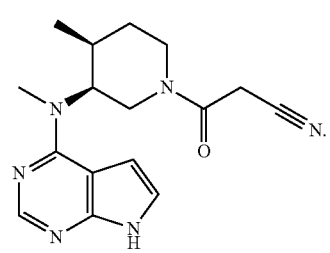 [SMILES: C[C@H]1CCN(C(=O)CC#N)C[C@H]1N(C)c1ncnc2[nH]ccc12]

Tofacitinib(3S,4R)

In an embodiment, the JAK inhibitor is Tofacitinib(3S,4R). Tofacitinib(3S,4R) has the chemical structure and name shown as: 3-[(3S,4R)-4-methyl-3-[methyl(7H-pyrrolo[2,3-d]pyrimidin-4-yl)amino]piperidin-1-yl]-3-oxopropanenitrile

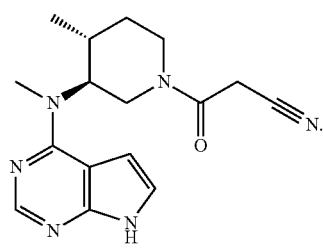 [SMILES: C[C@@H]1CCN(C(=O)CC#N)C[C@H]1N(C)c1ncnc2[nH]ccc12]

AEG3482

In an embodiment, the JAK inhibitor is AEG3482. AEG3482 has the chemical structure and name shown as: 6-phenylimidazo[2,1-b][1,3,4]thiadiazole-2-sulfonamide

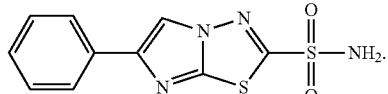

Lestaurtinib (CEP-701)

In an embodiment, the JAK inhibitor is Lestaurtinib (CEP-701). Lestaurtinib has the chemical structure and name shown as: (5R,7S,8S)-7-hydroxy-7-(hydroxymethyl)-8-methyl-5,6,7,8,13,14-hexahydro-15H-16-oxa-4b,8a,14-triaza-5,8-methanodibenzo[b,h]cycloocta[jkl]cyclopenta[e]-as-indacen-15-one

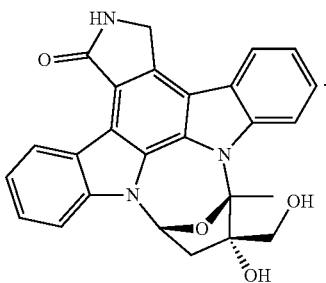 [SMILES: C[C@]12O[C@H](C[C@]1(O)CO)n1c3ccccc3c3c4c(c5c6ccccc6n2c5c31)CNC4=O]

Oclacitinib

In an embodiment, the JAK inhibitor is Oclacitinib. Oclacitinib has the chemical structure and name shown as: N-methyl-1-[4-[methyl(7H-pyrrolo[2,3-d]pyrimidin-4-yl)amino]cyclohexyl]methanesulfonamide

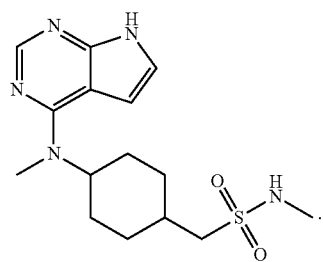 [SMILES: CNS(=O)(=O)CC1CCC(N(C)c2ncnc3[nH]ccc23)CC1]

In an embodiment, the JAK inhibitor is (E)-4-(2-(pyrrolidin-1-yl)ethoxy)-6,11-dioxa-3-aza-2(4,2)-pyrimidina-1(2,5)-furana-4(1,3)-benzenacyclododecaphan-8-ene. In an embodiment, the JAK inhibitor is (9E)-15-(2-(pyrrolidin-1-yl)ethoxy)-7,12,25-trioxa-19,21,24-triaza-tetracyclo[18.3.1.1(2,5).1(14,18)]hexacosa-1(24),2,4,9,14(26),15,17,20,22-nonaene. In an embodiment, the JAK inhibitor is a compound of Formula (LIV-A):

Formula (LIV-A)

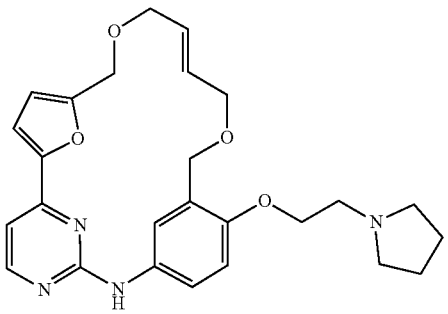

or a pharmaceutically acceptable salt thereof. The preparation and properties of this JAK inhibitor are known to those of ordinary skill in the art, and for example are described in: Madan (2012) J. Immunol. 189, 4123-4134 and William (2012) J. Med. Chem. 55, 2623-2640.

In an embodiment, the JAK inhibitor is (R)-(4-fluorophenyl)(4-((5-methyl-1H-pyrazol-3-yl)amino)quinazolin-2-yl)methanol, which is also known in the art to be active as a JAK inhibitor. In an embodiment, the JAK inhibitor is racemic (4-fluorophenyl)(4-((5-methyl-1H-pyrazol-3-yl)amino)quinazolin-2-yl)methanol, which is also known in the art to be active as a JAK inhibitor.

In an embodiment, the JAK inhibitor is (S)-5-fluoro-2-((1-(4-fluorophenyl)ethyl)amino)-6-((5-methyl-1H-pyrazol-3-yl)amino)nicotinonitrile. In an embodiment, the JAK inhibitor is a compound of Formula (LX):

Formula (LX)

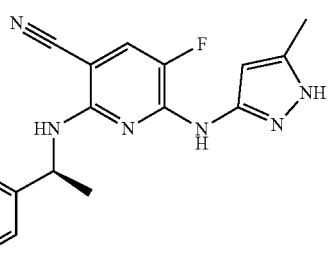

or a pharmaceutically acceptable salt thereof. The preparation of this compound is described in U.S. Pat. No. 8,324,252, the disclosure of which is incorporated by reference herein. In an embodiment, the JAK inhibitor is selected from the compounds described in U.S. Pat. No. 8,324,252, the disclosure of which is incorporated by reference herein.

In an embodiment, the JAK inhibitor is ((R)-7-(2-aminopyrimidin-5-yl)-1-((1-cyclopropyl-2,2,2-trifluoroethyl)amino)-5H-pyrido[4,3-b]indole-4-carboxamide, which is also named 7-(2-aminopyrimidin-5-yl)-1-{[(1R)-1-cyclopropyl-2,2,2-trifluoroethyl]amino}-5H-pyrido[4,3-b]indole-4-carboxamide. In an embodiment, the JAK inhibitor is a compound of Formula (LXII):

Formula (LXII)

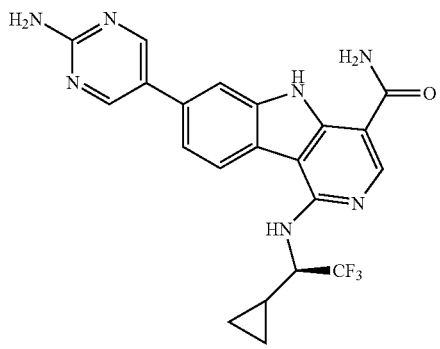

or a pharmaceutically acceptable salt thereof. The preparation of this compound is known to those of ordinary skill in the art, and is described in Lim (2011) J. Med. Chem. 54, 7334-7349, the disclosure of which is incorporated by reference herein.

IDH Inhibitors

Enasidenib

In an embodiment, the IDH inhibitor is Enasidenib. Enasidenib has the chemical structure and name shown as: 2-methyl-1-[[4-[6-(trifluoromethyl)pyridin-2-yl]-6-[[2-(trifluoromethyl)pyridin-4-yl]amino]-1,3,5-triazin-2-yl]amino]propan-2-ol

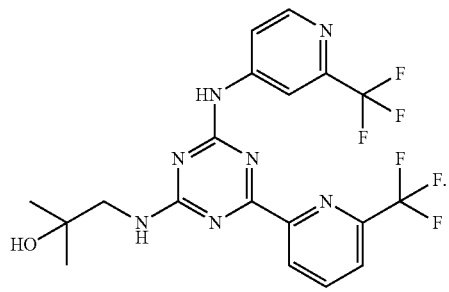 [SMILES: CC(C)(O)CNc1nc(Nc2ccnc(C(F)(F)F)c2)nc(-c2cccc(C(F)(F)F)n2)n1]

Ivosidenib (AG-120)

In an embodiment, the IDH inhibitor is Ivosidenib. Ivosidenib has the chemical structure and name shown as: (2S)—N-[(1S)-1-(2-chlorophenyl)-2-[(3,3-difluorocyclobutyl)amino]-2-oxoethyl]-1-(4-cyanopyridin-2-yl)-N-(5-fluoropyridin-3-yl)-5-oxopyrrolidine-2-carboxamide

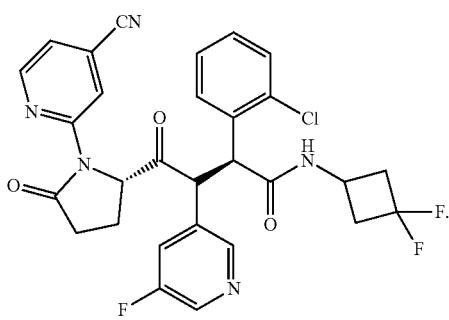 [SMILES: N#Cc1ccnc(N2C(=O)CC[C@H]2C(=O)C(c2cncc(F)c2)[C@H](C(=O)NC2CC(F)(F)C2)c2ccccc2Cl)c1]

AGI-5198 (IDH-C35)

In an embodiment, the IDH inhibitor is AGI-5198. AGI-5198 has the chemical structure and name shown as: N-cyclohexyl-2-(3-fluoro-N-[2-(2-methylimidazol-1-yl)acetyl]anilino)-2-(2-methylphenyl)acetamide

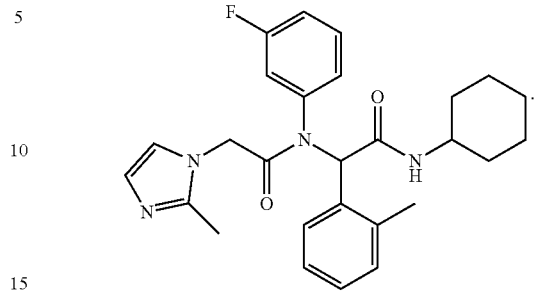

AGI-6780

In an embodiment, the IDH inhibitor is AGE-6780. AG0-6780 has the chemical structure and name shown as: 1-[5-(cyclopropylsulfamoyl)-2-thiophen-3-ylphenyl]-3-[3-(trifluoromethyl)phenyl]urea

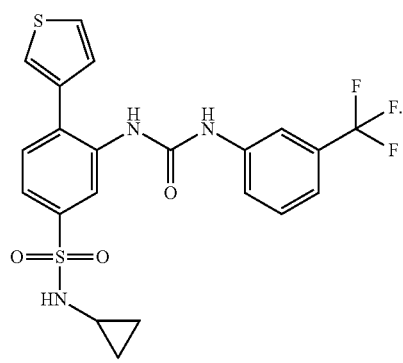 [SMILES: O=C(Nc1cccc(C(F)(F)F)c1)Nc1cc(S(=O)(=O)NC2CC2)ccc1-c1ccsc1]

CHEMBL3682093

In an embodiment, the IDH inhibitor is CHIEMBL3682093. CHENML3682093 has the chemical structure and name shown as: (4S)-3-[2-[[(1S)-1-[4-[(4-acetylpiperazin-1-yl)methyl]phenyl]ethyl]amino]pyrimidin-4-yl]-4-propan-2-yl-1,3-oxazolidin-2-one

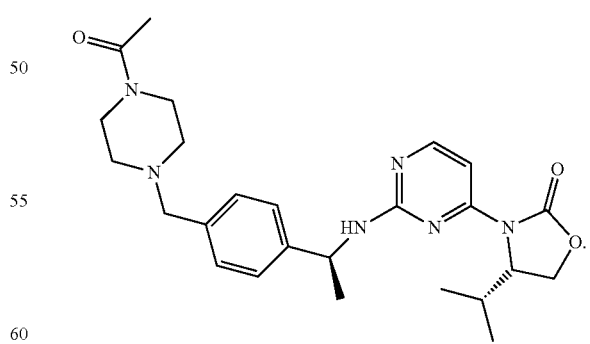

Vorasidenib (AG-881)

In an embodiment, the IDH inhibitor is Vorasidenib. Vorasidenib has the chemical structure and name shown as: 6-(6-chloropyridin-2-yl)-2-N,4-N-bis[(2R)-1,1,1-trifluoropropan-2-yl]-1,3,5-triazine-2,4-diamine

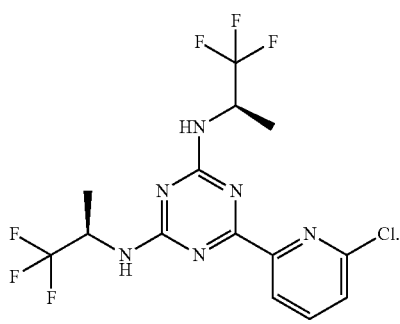 [SMILES: C[C@@H](Nc1nc(N[C@H](C)C(F)(F)F)nc(-c2cccc(Cl)n2)n1)C(F)(F)F]

IDH-305

In an embodiment, the IDH inhibitor is IDH-305. IDH-305 has the chemical structure and name shown as: (4R)-4-[(1S)-1-fluoroethyl]-3-[2-[[(1S)-1-[4-methyl-5-[2-(trifluoromethyl)pyridin-4-yl]pyridin-2-yl]ethyl]amino]pyrimidin-4-yl]-1,3-oxazolidin-2-one

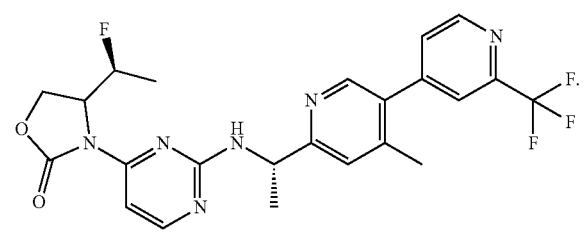 [SMILES: Cc1cc([C@H](C)Nc2nccc(N3C(=O)OCC3[C@H](C)F)n2)ncc1-c1ccnc(C(F)(F)F)c1]

BAY-1436032

In an embodiment, the IDH inhibitor is BAY-1436032. BAY-1436032 has the chemical structure and name shown as: 3-[2-[4-(trifluoromethoxy)anilino]-1-[(1R,5R)-3,3,5-trimethylcyclohexyl]benzimidazol-5-yl]propanoic acid

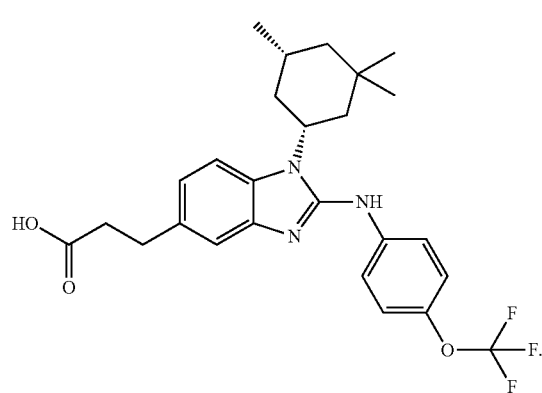 [SMILES: C[C@H]1C[C@@H](n2c(Nc3ccc(OC(F)(F)F)cc3)nc3cc(CCC(=O)O)ccc32)CC(C)(C)C1]

GSK864

In an embodiment, the IDH inhibitor is GSK864. GSK864 has the chemical structure and name shown as: (7S)-1-[(4-fluorophenyl)methyl]-3-N-(4-methoxy-3,5-dimethylphenyl)-7-methyl-5-(1H-pyrrole-2-carbonyl)-4,6-dihydropyrazolo[4,3-c]pyridine-3,7-dicarboxamide

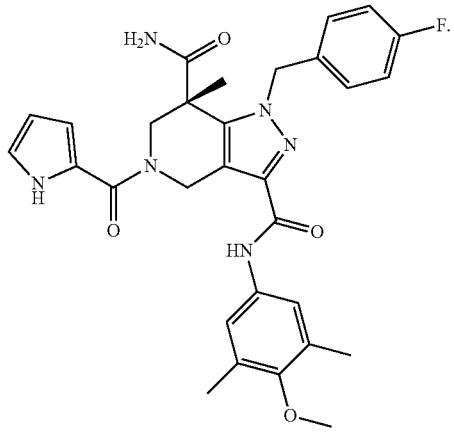 [SMILES: COc1c(C)cc(NC(=O)c2nn(Cc3ccc(F)cc3)c3c2CN(C(=O)c2ccc[nH]2)C[C@]3(C)C(N)=O)cc1C]

(R,S)-Ivosidenib

In an embodiment, the IDH inhibitor is (R,S)-Ivosidenib. (R,S)-Ivosidenib has the chemical structure and name shown as: (2R)—N-[(1S)-1-(2-chlorophenyl)-2-[(3,3-difluorocyclobutyl)amino]-2-oxoethyl]-1-(4-cyanopyridin-2-yl)-N-(5-fluoropyridin-3-yl)-5-oxopyrrolidine-2-carboxamide

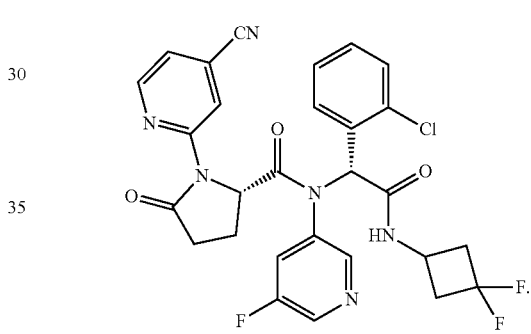

IDH1-IN-2

In an embodiment, the IDH inhibitor is IDH1-IN-2. IDH1-IN-2 has the chemical structure and name shown as: (4S)-3-[2-[[(1S)-1-[4-[(4,4-difluoropiperidin-1-yl)methyl]phenyl]ethyl]amino]pyrimidin-4-yl]-4-propan-2-yl-1,3-oxazolidin-2-one

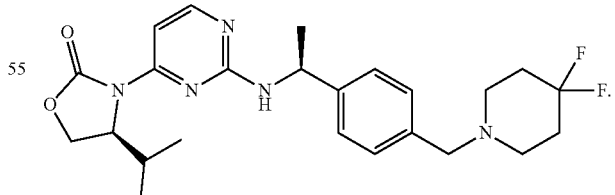

IDH1-IN-1

In an embodiment, the IDH inhibitor is IDH1-IN-1. IDH1-IN-1 has the chemical structure and name shown as: 2-(N-[2-(benzimidazol-1-yl)acetyl]-3-fluoroanilino)-N-cyclohexyl-2-(2-methylphenyl)acetamide

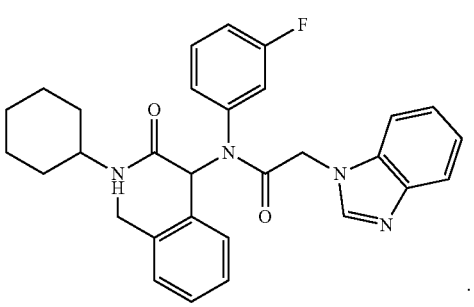 [SMILES: O=C1C(N(C(=O)Cn2cnc3ccccc32)c2cccc(F)c2)c2ccccc2CN1C1CCCCC1]

Enasidenib Mesylate

In an embodiment, the IDH inhibitor is Enasidenib mesylate. Enasidenib mesylate has the chemical structure and name shown as: 2-methyl-1-[[4-[6-(trifluoromethyl)pyridin-2-yl]-6-[[2-(trifluoromethyl)pyridin-4-yl]amino]-1,3,5-triazin-2-yl]amino]propan-2-ol methanesulfonic acid

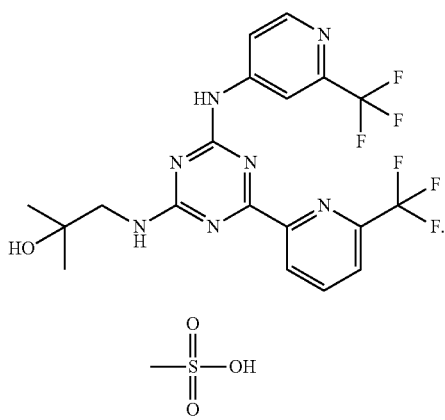

PD-1 Inhibitors

The PD-1 inhibitor may be any PD-1 inhibitor or PD-1 blocker known in the art. In particular, it is one of the PD-1 inhibitors or blockers described in more detail in the following paragraphs. The terms "inhibitor" and "blocker" are used interchangeably herein in reference to PD-1 inhibitors. For avoidance of doubt, references herein to a PD-1 inhibitor that is an antibody may refer to a compound or antigen-binding fragments, variants, conjugates, or biosimilars thereof. For avoidance of doubt, references herein to a PD-1 inhibitor may also refer to a compound or a pharmaceutically acceptable salt, ester, solvate, hydrate, cocrystal, or prodrug thereof.

In some embodiments, the compositions and methods described include a PD-1 inhibitor. In some embodiments, the PD-1 inhibitor is a small molecule. In a preferred embodiment, the PD-1 inhibitor is an antibody, a fragment thereof, including Fab fragments, or a single-chain variable fragment (scFv). In some embodiments the PD-1 inhibitor is a polyclonal antibody. In a preferred embodiment, the PD-1 inhibitor is a monoclonal antibody. In some embodiments, the PD-1 inhibitor competes for binding with PD-1, and/or binds to an epitope on PD-1. In an embodiment, the antibody competes for binding with PD-1, and/or binds to an epitope on PD-1. In some embodiments, the PD-1 inhibitor is included in a composition or a method and is further combined with a BTK inhibitor, a PI3K inhibitor, and/or a JAK-2 inhibitor. In some embodiments, an anti-PD-1 monoclonal antibody is included in a composition or a method and is further combined with a BTK inhibitor, a PI3K inhibitor, and/or a JAK-2 inhibitor. In some embodiments, an anti-PD-1 monoclonal antibody is included in a composition or a method and is further combined with a BTK inhibitor and/or a JAK-2 inhibitor. In some embodiments, a PD-1 inhibitor is included in a composition or a method and is further combined with a BTK inhibitor. In some embodiments, an anti-PD-1 monoclonal antibody is included in a composition or a method and is further combined with a BTK inhibitor. In some embodiments, a PD-1 inhibitor is included in a composition or a method and is further combined with a PI3K inhibitor. In some embodiments, an anti-PD-1 monoclonal antibody is included in a composition or a method and is further combined with a PI3K inhibitor. In some embodiments, a PD-1 inhibitor is included in a composition or a method and is further combined with a JAK-2 inhibitor. In some embodiments, an anti-PD-1 monoclonal antibody is included in a composition or a method and is further combined with a JAK-2 inhibitor. In some embodiments, the compositions described herein provide a combination of a PD-1 inhibitor with a BTK inhibitor, or methods of using a combination of a PD-1 inhibitor with a BTK inhibitor. In some embodiments, the PD-1 inhibitors provided herein are selective for PD-1, in that the compounds bind or interact with PD-1 at substantially lower concentrations than they bind or interact with other receptors.

In some embodiments, the compositions and methods described include a PD-1 inhibitor that binds human PD-1 with a $K_D$ of about 100 pM or lower, binds human PD-1 with a $K_D$ of about 90 pM or lower, binds human PD-1 with a $K_D$ of about 80 pM or lower, binds human PD-1 with a $K_D$ of about 70 pM or lower, binds human PD-1 with a $K_D$ of about 60 pM or lower, binds human PD-1 with a $K_D$ of about 50 pM or lower, binds human PD-1 with a $K_D$ of about 40 pM or lower, or binds human PD-1 with a $K_D$ of about 30 pM or lower.

In some embodiments, the compositions and methods described include a PD-1 inhibitor that binds to human PD-1 with a $k_{assoc}$ of about $7.5 \times 10^5$ 1/M·s or faster, binds to human PD-1 with a $k_{assoc}$ of about $7.5 \times 10^5$ 1/M·s or faster, binds to human PD-1 with a $k_{assoc}$ of about $8 \times 10^5$ 1/M·s or faster, binds to human PD-1 with a $k_{assoc}$ of about $8.5 \times 10^5$ 1/M·s or faster, binds to human PD-1 with a $k_{assoc}$ of about $9 \times 10^5$ 1/M·s or faster, binds to human PD-1 with a $k_{assoc}$ of about $9.5 \times 10^5$ 1/M·s or faster, or binds to human PD-1 with a $k_{assoc}$ of about $1 \times 10^6$ 1/M·s or faster.

In some embodiments, the compositions and methods described include a PD-1 inhibitor that binds to human PD-1 with a $k_{dissoc}$ of about $2 \times 10^{-5}$ 1/s or slower, binds to human PD-1 with a $k_{dissoc}$ of about $2.1 \times 10^{-5}$ 1/s or slower, binds to human PD-1 with a $k_{dissoc}$ of about $2.2 \times 10^{-5}$ 1/s or slower, binds to human PD-1 with a $k_{dissoc}$ of about $2.3 \times 10^{-5}$ 1/s or slower, binds to human PD-1 with a $k_{dissoc}$ of about $2.4 \times 10^{-5}$ 1/s or slower, binds to human PD-1 with a $k_{dissoc}$ of about $2.5 \times 10^{-5}$ 1/s or slower, binds to human PD-1 with a $k_{dissoc}$ of about $2.6 \times 10^{-5}$ 1/s or slower or binds to human PD-1 with a $k_{dissoc}$ of about $2.7 \times 10^{-5}$ 1/s or slower, binds to human PD-1 with a $k_{dissoc}$ of about $2.8 \times 10^{-5}$ 1/s or slower, binds to human PD-1 with a $k_{dissoc}$ of about $2.9 \times 10^{-5}$ 1/s or slower, or binds to human PD-1 with a $k_{dissoc}$ of about $3 \times 10^{-5}$ 1/s or slower.

In some embodiments, the compositions and methods described include a PD-1 inhibitor that blocks or inhibits binding of human PD-L1 or human PD-L2 to human PD-1 with an $IC_{50}$ of about 10 nM or lower, blocks or inhibits binding of human PD-L1 or human PD-L2 to human PD-1 with an $IC_{50}$ of about 9 nM or lower, blocks or inhibits binding of human PD-L1 or human PD-L2 to human PD-1 with an $IC_{50}$ of about 8 nM or lower, blocks or inhibits binding of human PD-L1 or human PD-L2 to human PD-1 with an $IC_{50}$ of about 7 nM or lower, blocks or inhibits binding of human PD-L1 or human PD-L2 to human PD-1 with an $IC_{50}$ of about 6 nM or lower, blocks or inhibits binding of human PD-L1 or human PD-L2 to human PD-1 with an $IC_{50}$ of about 5 nM or lower, blocks or inhibits binding of human PD-L1 or human PD-L2 to human PD-1 with an $IC_{50}$ of about 4 nM or lower, blocks or inhibits binding of human PD-L1 or human PD-L2 to human PD-1 with an $IC_{50}$ of about 3 nM or lower, blocks or inhibits binding of human PD-L1 or human PD-L2 to human PD-1 with an $IC_{50}$ of about 2 nM or lower, or blocks or inhibits binding of human PD-L1 or human PD-L2 to human PD-1 with an $IC_{50}$ of about 1 nM or lower.

In an embodiment, an anti-PD-1 antibody comprises nivolumab, produced by Bristol-Myers Squibb Co., or antigen-binding fragments, conjugates, or variants thereof. Nivolumab is referred to as 5C4 in International Patent Publication No. WO 2006/121168. Nivolumab is assigned CAS registry number 946414-94-4 and is also known to those of ordinary skill in the art as BMS-936558, MDX-1106 or ONO-4538. Nivolumab is a fully human IgG4 antibody blocking the PD-1 receptor. The clinical safety and efficacy of nivolumab in various forms of cancer has been described in Wang, *Cancer Immunol* Res. 2014, 2, 846-56; Page, *Ann. Rev. Med.,* 2014, 65, 185-202; and Weber, *J. Clin. Oncology,* 2013, 31, 4311-4318. The nivolumab monoclonal antibody includes a heavy chain given by SEQ ID NO:1 and a light chain given by SEQ ID NO:2. In an embodiment, the anti-PD-1 antibody is an immunoglobulin G4 kappa, anti-(human CD274) antibody. In an embodiment, an anti-PD-1 antibody comprises heavy and light chains having the sequences shown in SEQ ID NO:1 and SEQ ID NO:2, respectively, or antigen binding fragments, Fab fragments, single-chain variable fragments (scFv), variants, or conjugates thereof. In an embodiment, an anti-PD-1 antibody comprises heavy and light chains that are each at least 99% identical to the sequences shown in SEQ ID NO:1 and SEQ ID NO:2, respectively. In an embodiment, an anti-PD-1 antibody comprises heavy and light chains that are each at least 98% identical to the sequences shown in SEQ ID NO:1 and SEQ ID NO:2, respectively. In an embodiment, an anti-PD-1 antibody comprises heavy and light chains that are each at least 97% identical to the sequences shown in SEQ ID NO:1 and SEQ ID NO:2, respectively. In an embodiment, an anti-PD-1 antibody comprises heavy and light chains that are each at least 96% identical to the sequences shown in SEQ ID NO:1 and SEQ ID NO:2, respectively. In an embodiment, an anti-PD-1 antibody comprises heavy and light chains that are each at least 95% identical to the sequences shown in SEQ ID NO:1 and SEQ ID NO:2, respectively.

In other embodiments, the anti-PD-1 antibody comprises the heavy and light chain CDRs or VRs of nivolumab. In one embodiment, the antibody $V_H$ region comprises the sequence shown in SEQ ID NO: 3, and the antibody $V_L$ region comprises the sequence shown in SEQ ID NO:4. In an embodiment, an anti-PD-1 antibody comprises $V_H$ and $V_L$ regions that are each at least 99% identical to the sequences shown in SEQ ID NO:3 and SEQ ID NO:4, respectively. In an embodiment, an anti-PD-1 antibody comprises $V_H$ and $V_L$ regions that are each at least 98% identical to the sequences shown in SEQ ID NO:3 and SEQ ID NO:4, respectively. In an embodiment, an anti-PD-1 antibody comprises $V_H$ and $V_L$ regions that are each at least 97% identical to the sequences shown in SEQ ID NO:3 and SEQ ID NO:4, respectively. In an embodiment, an anti-PD-1 antibody comprises $V_H$ and $V_L$ regions that are each at least 96% identical to the sequences shown in SEQ ID NO:3 and SEQ ID NO:4, respectively. In an embodiment, an anti-PD-1 antibody comprises $V_H$ and $V_L$ regions that are each at least 95% identical to the sequences shown in SEQ ID NO:3 and SEQ ID NO:4, respectively. In an alternative embodiment, the antibody comprises $V_H$ and/or $V_L$ regions having the amino acid sequences set forth in SEQ ID NO:3 and/or SEQ ID NO:4, respectively.

In another embodiment, the anti-PD-1 antibody comprises the heavy chain CDR1, CDR2 and CDR3 domains having the sequences set forth in SEQ ID NO:5, SEQ ID NO:6, and SEQ ID NO:7, respectively, or conservative amino acid substitutions thereof, and the light chain CDR1, CDR2 and CDR3 domains having the sequences set forth in SEQ ID NO:8, SEQ ID NO:9, and SEQ ID NO: 10, respectively, or conservative amino acid substitutions thereof.

In an embodiment, an anti-PD-1 antibody comprises CDR1, CDR2 and CDR3 domains that are each at least 95% identical to the sequences shown in SEQ ID NO:5, SEQ ID NO:6, and SEQ ID NO:7, respectively. In an embodiment, an anti-PD-1 antibody comprises CDR1, CDR2 and CDR3 domains that are each at least 94% identical to the sequences shown in SEQ ID NO:5, SEQ ID NO:6, and SEQ ID NO:7, respectively. In an embodiment, an anti-PD-1 antibody comprises CDR1, CDR2 and CDR3 domains that are each at least 90% identical to the sequences shown in SEQ ID NO:5, SEQ ID NO:6, and SEQ ID NO:7, respectively. In an embodiment, an anti-PD-1 antibody comprises CDR1, CDR2 and CDR3 domains that are each at least 88% identical to the sequences shown in SEQ ID NO:5, SEQ ID NO:6, and SEQ ID NO:7, respectively. In another embodiment, the antibody competes for binding with, and/or binds to the same epitope on PD-1 as the aforementioned antibodies.

In an embodiment, an anti-PD-1 antibody comprises CDR1, CDR2 and CDR3 domains that are each at least 95% identical to the sequences shown in SEQ ID NO:8, SEQ ID NO:9, and SEQ ID NO: 10, respectively. In an embodiment, an anti-PD-1 antibody comprises CDR1, CDR2 and CDR3 domains that are each at least 91% identical to the sequences shown in SEQ ID NO:8, SEQ ID NO:9, and SEQ ID NO: 10, respectively. In an embodiment, an anti-PD-1 antibody comprises CDR1, CDR2 and CDR3 domains that are each at least 90% identical to the sequences shown in SEQ ID NO:8, SEQ ID NO:9, and SEQ ID NO: 10, respectively. In an embodiment, an anti-PD-1 antibody comprises CDR1, CDR2 and CDR3 domains that are each at least 85% identical to the sequences shown in SEQ ID NO:8, SEQ ID NO:9, and SEQ ID NO:10, respectively. In another embodiment, the antibody competes for binding with, and/or binds to the same epitope on PD-1 as the aforementioned antibodies.

In an embodiment, the anti-PD-1 antibody is an antibody disclosed and/or prepared according to U.S. Pat. No. 8,008,449 or U.S. Patent Application Publication Nos. 2009/0217401 A1 or 2013/0133091 A1, the disclosures of which are specifically incorporated by reference herein. For example, in an embodiment, the monoclonal antibody includes 5C4 (referred to herein as nivolumab), 17D8, 2D3, 4H1, 4A11, 7D3, and 5F4, described in U.S. Pat. No. 8,008,449, the disclosures of which are hereby incorporated by reference. The PD-1 antibodies 17D8, 2D3, 4H1, 5C4, and 4A11, are all directed against human PD-1, bind specifically to PD-1 and do not bind to other members of the CD28 family. The sequences and CDR regions for these antibodies are provided in U.S. Pat. No. 8,008,449, in particular FIG. 1 through FIG. 12; all of which are incorporated by reference herein in their entireties.

The anti-PD-1 antibody nivolumab may be prepared by the following procedure, as described in U.S. Pat. No. 8,008,449. The antibody nivolumab may be produced in this manner, or by other known means given the disclosure of the amino acid sequences herein.

In another embodiment, the anti-PD-1 antibody comprises pembrolizumab, which is commercially available from Merck, or antigen-binding fragments, conjugates, or variants thereof. Pembrolizumab is referred to as h409A11 in International Patent Publication No. WO 2008/156712 A1, U.S. Pat. No. 8,354,509 and U.S. Patent Application Publication Nos. US 2010/0266617 A1, US 2013/0108651 A1, and US 2013/0109843 A2. Pembrolizumab has an immunoglobulin G4, anti-(human protein PDCD1 (programmed cell death 1)) (human-*Mus musculus* monoclonal heavy chain), disulfide with human-*Mus musculus* monoclonal light chain, dimer structure. The structure of pembrolizumab may also be described as immunoglobulin G4, anti-(human programmed cell death 1); humanized mouse monoclonal [228-L-proline (H10-S>P)]γ4 heavy chain (134-218')-disulfide with humanized mouse monoclonal κ light chain dimer (226-226":229-229")-bisdisulfide. Pembrolizumab is assigned CAS registry number 1374853-91-4 and is also known as lambrolizumab, MK-3475, and SCH-900475. The clinical safety and efficacy of pembrolizumab in various forms of cancer is described in Fuerst, *Oncology Times,* 2014, 36, 35-36; Robert, *Lancet,* 2014, 384, 1109-17; and Thomas, *Exp. Opin. Biol. Ther.,* 2014, 14, 1061-1064. In an embodiment, the pembrolizumab monoclonal antibody includes a heavy chain given by SEQ ID NO:12 and a light chain given by SEQ ID NO: 14, and also shown below with disulfide and glycosylation information:

```
Heavy chain
QVQLVQSGVEVKKPGASVKVSCKASGYTFTNYYMYWVRQAPGQGLEWMGG    50

INPSNGGTNFNEKFKNRVTLTTDSSTTTAYMELKSLQFDDTAVYYCARRD   100

YRFDMGFDYWGQGTTVTVSSASTKGPSVFPLAPCSRSTSESTAALGCLVK   150

DYFPEPVTVSWNSGALTSGVHTFPAVLQSSGLYSLSSVVTVPSSSLGTKT   200

YTCNVDHKPSNTKVDKRVESKYGPPCPPCPAPEFLGGPSVFLFPPKPKDT   250

LMISRTPEVTCVVVDVSQEDPEVQFNWYVDGVEVHNAKTKPREEQFNSTY   300

RVVSVLTVLHQDWLNGKEYKCKVSNKGLPSSIEKTISKAKGQPREPQVYT   350

LPPSQEEMTKNQVSLTCLVKGFYPSDIAVEWESNGQPENNYKTTPPVLDS   400

DGSFFLYSRLTVDKSRWQEGNVFSCSVMHEALHNHYTQKSLSLSLGK      447

Light chain
EIVLTQSPATLSLSPGERATLSCRASKGVSTSGYSYLHWYQQKPGQAPRL   50'

LIYLASYLESGVPARFSGSGSGTDFTLTISSLEPEDFAVYYCQHSRDLPL  100'

TFGGGTKVEIKRTVAAPSVFIFPPSDEQLKSGTASVVCLLNNFYPREAKV  150'

QWKVDNALQSGNSQESVTEQDSKDSTYSLSSTLTLSKADYEKHKVYACEV  200'

THQGLSSPVTKSENRGEC                                  218'

Disulfide bridges
22-96        22''-96''      23'-92'      23'''-92'''

134-218'     134''-218'''   138'-198'    138'''-198'''

147-203      147''-203''    226-226''    229-229''

261-321      261''-321''    367-425      367''-425''

Glycosylation sites (N)
Asn-297
```

In an embodiment, an anti-PD-1 antibody comprises heavy and light chains having the sequences shown in SEQ ID NO: 12 and SEQ ID NO:14, respectively, or antigen binding fragments and variants thereof. In an embodiment, an anti-PD-1 antibody comprises heavy and light chains that are each at least 99% identical to the sequences shown in SEQ ID NO:12 and SEQ ID NO: 14, respectively, or antigen binding fragments and variants thereof. In an embodiment, an anti-PD-1 antibody comprises heavy and light chains that are each at least 98% identical to the sequences shown in SEQ ID NO:12 and SEQ ID NO:14, respectively, or antigen binding fragments and variants thereof. In an embodiment, an anti-PD-1 antibody comprises heavy and light chains that are each at least 97% identical to the sequences shown in SEQ ID NO:12 and SEQ ID NO:14, respectively, or antigen binding fragments and variants thereof. In an embodiment, an anti-PD-1 antibody comprises heavy and light chains that are each at least 96% identical to the sequences shown in SEQ ID NO:12 and SEQ ID NO:14, respectively, or antigen binding fragments and variants thereof. In an embodiment, an anti-PD-1 antibody comprises heavy and light chains that are each at least 95% identical to the sequences shown in SEQ ID NO: 12 and SEQ ID NO:14, respectively, or antigen binding fragments and variants thereof.

In other embodiments, the anti-PD-1 antibody comprises the heavy and light chain CDRs or VRs of pembrolizumab. In an embodiment, the antibody $V_H$ region comprises the sequence of residues 20 to 446 of SEQ ID NO:11, and the antibody $V_L$ region comprises the sequence shown in SEQ ID NO:14. In an embodiment, an anti-PD-1 antibody comprises $V_H$ and $V_L$ regions that are each at least 99% identical to the sequences of residues 20 to 446 of SEQ ID NO:11 and the sequence shown in SEQ ID NO: 14, respectively. In an embodiment, an anti-PD-1 antibody comprises $V_H$ and $V_L$ regions that are each at least 98% identical to the sequences of residues 20 to 446 of SEQ ID NO:11 and the sequence shown in SEQ ID NO:14, respectively. In an embodiment, an anti-PD-1 antibody comprises $V_H$ and $V_L$ regions that are each at least 97% identical to the sequences of residues 20 to 446 of SEQ ID NO:11 and the sequence shown in SEQ ID NO: 14, respectively. In an embodiment, an anti-PD-1 antibody comprises $V_H$ and $V_L$ regions that are each at least 96% identical to the sequences of residues 20 to 446 of SEQ ID NO:11 and the sequence shown in SEQ ID NO: 14, respectively. In an embodiment, an anti-PD-1 antibody comprises $V_H$ and $V_L$ regions that are each at least 95% identical to the sequences of residues 20 to 446 of SEQ ID NO:11 and the sequence shown in SEQ ID NO:14, respectively.

In an embodiment, the anti-PD-1 antibody comprises a heavy chain comprising amino acid residues 20 to 446 of SEQ ID NO:11 and a light chain comprising amino acid residues of 20-237 of SEQ ID NO:13.

In an embodiment, the anti-PD-1 antibody is an isolated antibody or antibody fragment which binds to human PD-1 comprising three light chain CDRs of SEQ ID NO:15, SEQ ID NO:16, and SEQ ID NO:17, or conservative amino acid substitutions thereof, and three heavy chain CDRs of SEQ ID NO: 18, SEQ ID NO: 19 and SEQ ID NO:20, or conservative amino acid substitutions thereof.

In an embodiment, an anti-PD-1 antibody comprises a heavy chain that comprises CDR1, CDR2 and CDR3 domains that are each at least 95% identical to the sequences shown in SEQ ID NO: 15, SEQ ID NO: 16, and SEQ ID NO:17, respectively. In an embodiment, an anti-PD-1 antibody comprises a heavy chain that comprises CDR1, CDR2 and CDR3 domains that are each at least 90% identical to the sequences shown in SEQ ID NO:15, SEQ ID NO:16, and SEQ ID NO: 17, respectively. In an embodiment, an anti-PD-1 antibody comprises a heavy chain that comprises CDR1, CDR2 and CDR3 domains that are each at least 85% identical to the sequences shown in SEQ ID NO:15, SEQ ID NO:16, and SEQ ID NO:17, respectively. In an embodiment, an anti-PD-1 antibody comprises a heavy chain that comprises CDR1, CDR2 and CDR3 domains that are each at least 80% identical to the sequences shown in SEQ ID NO: 15, SEQ ID NO: 16, and SEQ ID NO:17, respectively. In another embodiment, the antibody competes for binding with, and/or binds to the same epitope on PD-1 as the aforementioned antibodies.

In an embodiment, an anti-PD-1 antibody comprises a light chain that comprises CDR1, CDR2 and CDR3 domains that are each at least 95% identical to the sequences shown in SEQ ID NO: 18, SEQ ID NO: 19, and SEQ ID NO:20, respectively. In an embodiment, an anti-PD-1 antibody comprises a light chain that comprises CDR1, CDR2 and CDR3 domains that are each at least 90% identical to the sequences shown in SEQ ID NO: 18, SEQ ID NO: 19, and SEQ ID NO:20, respectively. In an embodiment, an anti-PD-1 antibody comprises a light chain that comprises CDR1, CDR2 and CDR3 domains that are each at least 85% identical to the sequences shown in SEQ ID NO: 18, SEQ ID NO: 19, and SEQ ID NO:20, respectively. In an embodiment, an anti-PD-1 antibody comprises a light chain that comprises CDR1, CDR2 and CDR3 domains that are each at least 80% identical to the sequences shown in SEQ ID NO:18, SEQ ID NO:19, and SEQ ID NO:20, respectively. In another embodiment, the antibody competes for binding with, and/or binds to the same epitope on PD-1 as the aforementioned antibodies.

In an embodiment, the anti-PD-1 antibody is an antibody disclosed in U.S. Pat. No. 8,354,509 or U.S. Patent Application Publication Nos. 2010/0266617 A1, 2013/0108651 A1, 2013/0109843 A2, the disclosures of which are specifically incorporated by reference herein.

In an embodiment, the anti-PD-1 antibody is pidilizumab, which is also known as CT-011 (CureTech Ltd.), and which is disclosed in U.S. Pat. No. 8,686,119 B2, the disclosures of which are specifically incorporated by reference herein. The efficacy of pidilizumab in the treatment of cancers, such as hematological malignancies, is described in Berger, *Clin. Cancer Res.* 2008, 14, 3044-51. The pidilizumab monoclonal antibody includes a heavy chain given by SEQ ID NO:21 and a light chain given by SEQ ID NO:22. Pidilizumab has intra-heavy chain disulfide linkages at 22-96, 144-200, 261-321, 367-425, 22"-96", 144"-200", 261"-321", and 367"-425"; intra-light chain disulfide linkages at 23'-87', 133'-193', 23'''-87''', and 133'''-193'''; inter-heavy-light chain disulfide linkages at 220-213' and 220"-213'", inter-heavy-heavy chain disulfide linkages at 226-226" 229-229"; and N-glycosylation sites (H $CH_2$ 84.4) at 297, 297".

In an embodiment, the anti-PD-1 antibody is an immunoglobulin G1 kappa, anti-(human CD274) humanized monoclonal antibody. In an embodiment, an anti-PD-1 antibody comprises heavy and light chains having the sequences shown in SEQ ID NO:21 and SEQ ID NO:22, respectively, or antigen binding fragments, variants, or conjugates thereof. In an embodiment, an anti-PD-1 antibody comprises heavy and light chains that are each at least 99% identical to the sequences shown in SEQ ID NO:21 and SEQ ID NO:22, respectively. In an embodiment, an anti-PD-1 antibody comprises heavy and light chains that are each at least 98% identical to the sequences shown in SEQ ID NO:21 and SEQ ID NO:22, respectively. In an embodiment, an anti-PD-1 antibody comprises heavy and light chains that are each at least 97% identical to the sequences shown in SEQ ID NO:21 and SEQ ID NO:22, respectively. In an embodiment, an anti-PD-1 antibody comprises heavy and light chains that are each at least 96% identical to the sequences shown in SEQ ID NO:21 and SEQ ID NO:22, respectively. In an embodiment, an anti-PD-1 antibody comprises heavy and light chains that are each at least 95% identical to the sequences shown in SEQ ID NO:21 and SEQ ID NO:22, respectively.

In an embodiment, an anti-PD-L1 antibody comprises $V_H$ and $V_L$ regions that are each at least 99% identical to the sequences shown in SEQ ID NO:23 and SEQ ID NO:24, respectively. In an embodiment, an anti-PD-L1 antibody comprises $V_H$ and $V_L$ regions that are each at least 98% identical to the sequences shown in SEQ ID NO:23 and SEQ ID NO:24, respectively. In an embodiment, an anti-PD-L1 antibody comprises $V_H$ and $V_L$ regions that are each at least 97% identical to the sequences shown in SEQ ID NO:23 and SEQ ID NO:24, respectively. In an embodiment, an anti-PD-L1 antibody comprises $V_H$ and $V_L$ regions that are each at least 96% identical to the sequences shown in SEQ ID NO:23 and SEQ ID NO:24, respectively. In an embodiment, an anti-PD-L1 antibody comprises $V_H$ and $V_L$ regions that are each at least 95% identical to the sequences shown in SEQ ID NO:23 and SEQ ID NO:24, respectively.

In another embodiment, anti-PD-1 antibodies and other PD-1 inhibitors include those described in U.S. Pat. Nos. 8,287,856, 8,580,247, and 8,168,757 and U.S. Patent Application Publication Nos. 2009/0028857 A1, 2010/0285013 A1, 2013/0022600 A1, and 2011/0008369 A1, the teachings of which are hereby incorporated by reference. In another embodiment, antibodies that compete with any of these antibodies for binding to PD-1 are also included. In another embodiment, the anti-PD-1 antibody is an antibody disclosed in U.S. Pat. No. 8,735,553 B1, the disclosures of which are incorporated herein by reference.

In an embodiment, the anti-PD-1 antibody is a commercially-available monoclonal antibody, such as anti-m-PD-1 clones J43 (Cat #BE0033-2) and RMP1-14 (Cat #BE0146) (Bio X Cell, Inc., West Lebanon, NH, USA). A number of commercially-available anti-PD-1 antibodies are known to one of ordinary skill in the art.

Monoclonal antibodies that inhibit or block PD-1 can be prepared by procedures known to those of ordinary knowledge and skill in the art, e.g., by injecting test subjects with PD-1 antigen and then isolating hybridomas expressing antibodies having the desired sequence or functional characteristics. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, myeloma cells, or other suitable cells that do not otherwise produce immunoglobulin protein, to obtain the synthesis of monoclonal antibodies in the recombinant host cells. The details of recombinant production of specific antibodies may be found in the references cited in the foregoing, the disclosures of which are incorporated by reference herein. Monoclonal antibodies that inhibit PD-1 can be prepared by standard molecular biology methods using the sequences provided herein by reverse translation and insertion into appropriate DNA or RNA vectors.

The anti-PD-1 antibody sequences discussed and referenced in the foregoing embodiments are summarized in Table 1.

TABLE 1

Anti-PD-1 antibody amino acid sequences.

| Identifier | Amino Acid Sequence |
|---|---|
| SEQ ID NO:1 | nivolumab heavy chain |
| SEQ ID NO:2 | nivolumab light chain |
| SEQ ID NO:3 | nivolumab variable heavy chain |
| SEQ ID NO:4 | nivolumab variable light chain |
| SEQ ID NO:5 | nivolumab heavy chain CDR1 |
| SEQ ID NO:6 | nivolumab heavy chain CDR2 |
| SEQ ID NO:7 | nivolumab heavy chain CDR3 |
| SEQ ID NO:8 | nivolumab light chain CDR1 |
| SEQ ID NO:9 | nivolumab light chain CDR2 |
| SEQ ID NO:10 | nivolumab light chain CDR3 |
| SEQ ID NO:11 | pembrolizumab heavy chain |
| SEQ ID NO:12 | pembrolizumab heavy chain |
| SEQ ID NO:13 | pembrolizumab variable light chain |
| SEQ ID NO:14 | pembrolizumab light chain |
| SEQ ID NO:15 | pembrolizumab light chain CDR1 |
| SEQ ID NO:16 | pembrolizumab light chain CDR2 |
| SEQ ID NO:17 | pembrolizumab light chain CDR3 |
| SEQ ID NO:18 | pembrolizumab heavy chain CDR1 |
| SEQ ID NO:19 | pembrolizumab heavy chain CDR2 |
| SEQ ID NO:20 | pembrolizumab heavy chain CDR3 |
| SEQ ID NO:21 | pidilizumab heavy chain |
| SEQ ID NO:22 | pidilizumab light chain |
| SEQ ID NO:23 | pidilizumab variable heavy chain |
| SEQ ID NO:24 | pidilizumab variable light chain |

The PD-1 inhibitor may also be a small molecule or peptide, or a peptide derivative, such as those described in U.S. Pat. Nos. 8,907,053; 9,096,642; and 9,044,442 and U.S. Patent Application Publication No. 2015/0087581; 1,2,4 oxadiazole compounds and derivatives such as those described in U.S. Patent Application Publication No. 2015/0073024; cyclic peptidomimetic compounds and derivatives such as those described in U.S. Patent Application Publication No. 2015/0073042; cyclic compounds and derivatives such as those described in U.S. Patent Application Publication No. 2015/0125491; 1,3,4 oxadiazole and 1,3,4 thiadiazole compounds and derivatives such as those described in International Patent Application Publication No. WO 2015/033301; peptide-based compounds and derivatives such as those described in International Patent Application Publication Nos. WO 2015/036927 and WO 2015/04490, or a macrocyclic peptide-based compounds and derivatives such as those described in U.S. Patent Application Publication No. 2014/0294898; the disclosures of each of which are hereby incorporated by reference in their entireties.

In an embodiment, the PD-1 inhibitor is AUNP-12.

In an embodiment, the PD-1 inhibitor is a compound selected from the group consisting of:

(SEQ ID NO: 26-28)

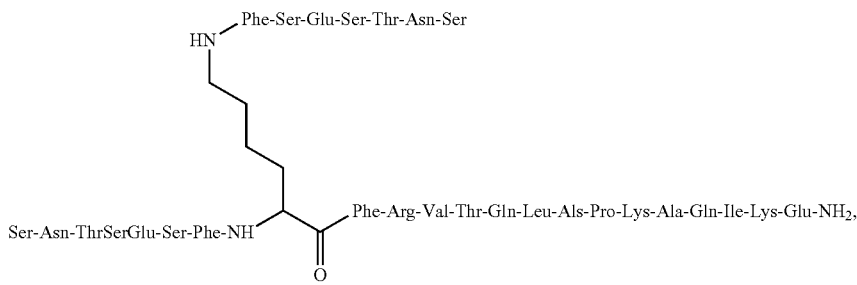

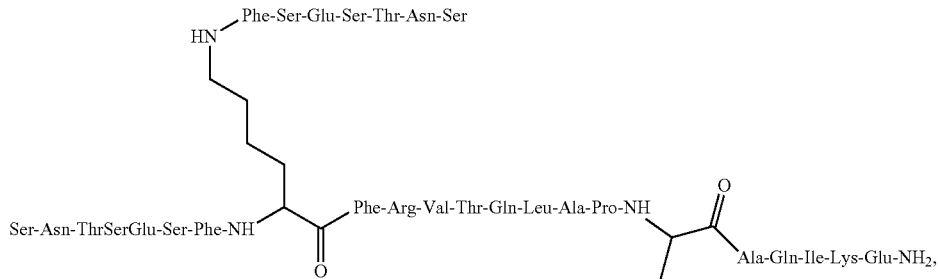

(SEQ ID NO: 29-32)

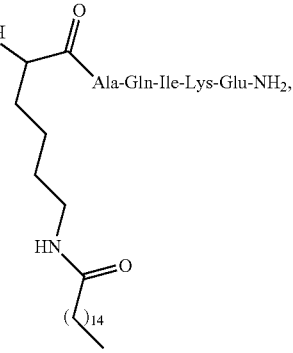

(SEQ ID NO: 33-36)

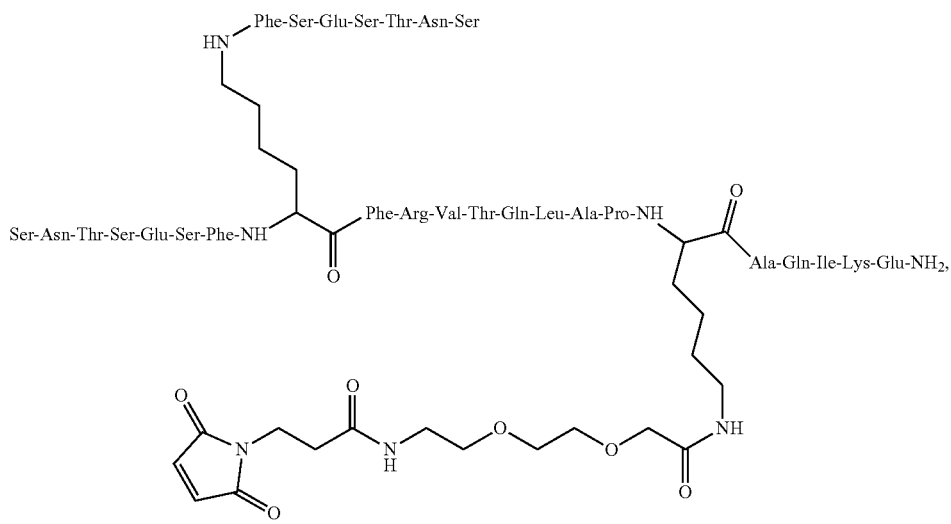

and SEQ ID NO:37-38, wherein the branched groups are given by SEQ ID NO:25, and pharmaceutically acceptable salts, solvates, hydrates, cocrystals, or prodrugs thereof.

In an embodiment, the PD-1 inhibitor is selected from group consisting of nivolumab, pembrolizumab, pidilizumab, AMP-224, AMP-514, PDR001, and combinations thereof. In an embodiment the PD-1 inhibitor is nivolumab. In an embodiment the PD-1 inhibitor is pembrolizumab. In an embodiment the PD-1 inhibitor is Pidilizumab. In an embodiment the PD-1 inhibitor is AMP-224.

PD-L1 and PD-L2 Inhibitors

The PD-L1 or PD-L2 inhibitor may be any PD-L1 or PD-L2 inhibitor or blocker known in the art. In particular, it is one of the PD-L1 or PD-L2 inhibitors or blockers described in more detail in the following paragraphs. The terms "inhibitor" and "blocker" are used interchangeably herein in reference to PD-L1 and PD-L2 inhibitors. For avoidance of doubt, references herein to a PD-L1 or PD-L2 inhibitor that is an antibody may refer to a compound or antigen-binding fragments, variants, conjugates, or biosimilars thereof. For avoidance of doubt, references herein to a PD-L1 or PD-L2 inhibitor may refer to a compound or a pharmaceutically acceptable salt, ester, solvate, hydrate, cocrystal, or prodrug thereof.

In some embodiments, the compositions and methods include a PD-L1 or PD-L2 inhibitor. In some embodiments, the PD-L1 and PD-L2 inhibitor is a small molecule. In some embodiments, the PD-L1 or PD-L2 inhibitor is an anti-PD-L1 or anti-PD-L2 antibody, a fragment thereof, including Fab fragments or single-chain variable fragments (scFv). In an aspect of the invention, the anti-PD-1 antibody or fragment thereof in any of the aforementioned embodiments is replaced by, or combined with, an anti-PD-L1 or anti-PD-L2 antibody or fragment thereof. In an embodiment, the antibody competes for binding with, and/or binds to an epitope on PD-L1 and/or PD-L2. In some embodiments, the PD-L1 or PD-L2 inhibitor is a monoclonal antibody. In some embodiments the PD-L1 or PD-L2 inhibitor is a polyclonal antibody. In some embodiments, a PD-L1 inhibitor is included in a composition or a method and is further combined with a BTK inhibitor, a PI3K inhibitor, and/or a JAK-2 inhibitor. In some embodiments, an anti-PD-L1 monoclonal antibody is included in a composition or a method and is further combined with a BTK inhibitor, a PI3K inhibitor, and/or a JAK-2 inhibitor. In some embodiments, a PD-L2 inhibitor is included in a composition or a method and is further combined with a BTK inhibitor, a PI3K inhibitor, and/or a JAK-2 inhibitor. In some embodiments, an anti-PD-L2 monoclonal antibody is included in a composition or a method and is further combined with a BTK inhibitor, a PI3K inhibitor, and/or a JAK-2 inhibitor. In some embodiments, a PD-L1 inhibitor is included in a composition or a method and is further combined with a BTK inhibitor. In some embodiments, an anti-PD-L1 monoclonal antibody is included in a composition or a method and is further combined with a BTK inhibitor. In some embodiments, a PD-L2 inhibitor is included in a composition or a method and is further combined with a BTK inhibitor. In some embodiments, an anti-PD-L2 monoclonal antibody is included in a composition or a method and is further combined with a BTK inhibitor. In some embodiments, a PD-L1 inhibitor is included in a composition or a method and is further combined with a PI3K inhibitor. In some embodiments, an anti-PD-L1 monoclonal antibody is included in a composition or a method and is further combined with a PI3K inhibitor. In some embodiments, a PD-L2 inhibitor is included in a composition or a method and is further combined with a PI3K inhibitor. In some embodiments, an anti-PD-L2 monoclonal antibody is included in a composition or a method and is further combined with a PI3K inhibitor. In some embodiments, a PD-L1 inhibitor is included in a composition or a method and is further combined with a JAK-2 inhibitor. In some embodiments, an anti-PD-L1 monoclonal antibody is included in a composition or a method and is further combined with a JAK-2 inhibitor. In some embodiments, a PD-L2 inhibitor is included in a composition or a method and is further combined with a JAK-2 inhibitor. In some embodiments, an anti-PD-L2 monoclonal antibody is included in a composition or a method and is further combined with a JAK-2 inhibitor. In some embodiments, both a PD-1 inhibitor and a PD-L1 inhibitor are included in a composition or method and are further combined with a BTK inhibitor, a PI3K inhibitor, and/or a JAK-2 inhibitor. In some embodiments, both an anti-PD-1 monoclonal antibody and an anti-PD-L1 monoclonal antibody are included in a composition or method and are further combined with a BTK inhibitor, a PI3K inhibitor, and/or a JAK-2 inhibitor. In some embodiments, both a PD-1 inhibitor and a PD-L2 inhibitor are included in a composition or method and are further combined with a BTK inhibitor, a PI3K inhibitor, and/or a JAK-2 inhibitor. In some embodiments, both an anti-PD-1 monoclonal antibody and an anti-PD-L2 monoclonal antibody are included in a composition or method and are further combined with a BTK inhibitor, a PI3K inhibitor, and/or a JAK-2 inhibitor.

In some embodiments, the compositions described herein provide a combination of a PD-L1 and/or PD-L2 inhibitor with a BTK inhibitor, or methods of using a combination of a PD-L1 and/or PD-L2 inhibitor with a BTK inhibitor. In some embodiments, the PD-L1 inhibitors provided herein are selective for PD-L1, in that the compounds bind or interact with PD-L1 at substantially lower concentrations than they bind or interact with other receptors, including the PD-L2 receptor. In certain embodiments, the compounds bind to the PD-L2 receptor at a binding constant that is at least about a 2-fold higher concentration, about a 3-fold higher concentration, about a 5-fold higher concentration, about a 10-fold higher concentration, about a 20-fold higher concentration, about a 30-fold higher concentration, about a 50-fold higher concentration, about a 100-fold higher concentration, about a 200-fold higher concentration, about a 300-fold higher concentration, or about a 500-fold higher concentration than to the PD-L1 receptor.

Without being bound by any theory, it is believed that tumor cells express PD-L1, and that T cells express PD-1. However, PD-L1 expression by tumor cells is not required for efficacy of PD-1 or PD-L1 inhibitors or blockers. In an embodiment, the tumor cells express PD-L1. In another embodiment, the tumor cells do not express PD-L1. In some embodiments, the methods and compositions described herein include a combination of a PD-1 and a PD-L1 antibody, such as those described herein, in combination with a BTK inhibitor. The administration of a combination of a PD-1 and a PD-L1 antibody and a BTK inhibitor may be simultaneous or sequential.

In some embodiments, the compositions and methods described include a PD-L1 and/or PD-L2 inhibitor that binds human PD-L1 and/or PD-L2 with a $K_D$ of about 100 pM or lower, binds human PD-L1 and/or PD-L2 with a $K_D$ of about 90 pM or lower, binds human PD-L1 and/or PD-L2 with a $K_D$ of about 80 pM or lower, binds human PD-L1 and/or PD-L2 with a $K_D$ of about 70 pM or lower, binds human PD-L1 and/or PD-L2 with a $K_D$ of about 60 pM or lower, a $K_D$ of about 50 pM or lower, binds human PD-L1 and/or PD-L2 with a $K_D$ of about 40 pM or lower, or binds human PD-L1 and/or PD-L2 with a $K_D$ of about 30 pM or lower, In some embodiments, the compositions and methods described include a PD-L1 and/or PD-L2 inhibitor that binds to human PD-L1 and/or PD-L2 with a $k_{assoc}$ of about $7.5 \times 10^5$ 1/M s or faster, binds to human PD-L1 and/or PD-L2 with a $k_{assoc}$ of about $8 \times 10^5$ 1/M·s or faster, binds to human PD-L1 and/or PD-L2 with a $k_{assoc}$ of about $8.5 \times 10^5$ 1/M·s or faster, binds to human PD-L1 and/or PD-L2 with a $k_{assoc}$ of about $9 \times 10^5$ 1/M·s or faster, binds to human PD-L1 and/or PD-L2 with a $k_{assoc}$ of about $9.5 \times 10^5$ 1/M·s and/or faster, or binds to human PD-L1 and/or PD-L2 with a $k_{assoc}$ of about $1 \times 10^6$ 1/Ms or faster.

In some embodiments, the compositions and methods described include a PD-L1 and/or PD-L2 inhibitor that binds to human PD-L1 or PD-L2 with a $k_{dissoc}$ of about $2 \times 10^{-5}$ 1/s or slower, binds to human PD-1 with a $k_{dissoc}$ of about $2.1 \times 10^{-5}$ 1/s or slower, binds to human PD-1 with a $k_{dissoc}$ of about $2.2 \times 10^{-5}$ 1/s or slower, binds to human PD-1 with a $k_{dissoc}$ of about $2.3 \times 10^{-5}$ 1/s or slower, binds to human PD-1 with a $k_{dissoc}$ of about $2.4 \times 10^{-5}$ 1/s or slower, binds to human PD-1 with a $k_{dissoc}$ of about $2.5 \times 10^{-5}$ 1/s or slower, binds to human PD-1 with a $k_{dissoc}$ of about $2.6 \times 10^{-5}$ 1/s or slower, binds to human PD-L1 or PD-L2 with a $k_{dissoc}$ of about $2.7 \times 10^{-5}$ 1/s or slower, or binds to human PD-L1 or PD-L2 with a $k_{dissoc}$ of about $3 \times 10^{-5}$ 1/s or slower.

In some embodiments, the compositions and methods described include a PD-L1 and/or PD-L2 inhibitor that blocks or inhibits binding of human PD-L1 or human PD-L2 to human PD-1 with an $IC_{50}$ of about 10 nM or lower; blocks or inhibits binding of human PD-L1 or human PD-L2 to human PD-1 with an $IC_{50}$ of about 9 nM or lower; blocks or inhibits binding of human PD-L1 or human PD-L2 to human PD-1 with an $IC_{50}$ of about 8 nM or lower; blocks or inhibits binding of human PD-L1 or human PD-L2 to human PD-1 with an $IC_{50}$ of about 7 nM or lower; blocks or inhibits binding of human PD-L1 or human PD-L2 to human PD-1 with an $IC_{50}$ of about 6 nM or lower; blocks or inhibits binding of human PD-L1 or human PD-L2 to human PD-1 with an $IC_{50}$ of about 5 nM or lower; blocks or inhibits binding of human PD-L1 or human PD-L2 to human PD-1 with an $IC_{50}$ of about 4 nM or lower; blocks or inhibits binding of human PD-L1 or human PD-L2 to human PD-1 with an $IC_{50}$ of about 3 nM or lower; blocks or inhibits binding of human PD-L1 or human PD-L2 to human PD-1 with an $IC_{50}$ of about 2 nM or lower; or blocks human PD-1, or blocks binding of human PD-L1 or human PD-L2 to human PD-1 with an $IC_{50}$ of about 1 nM or lower.

In an embodiment, the anti-PD-L1 antibody is durvalumab, which is also known as MEDI4736, produced by Medimmune, LLC, Gaithersburg, Md., a subsidiary of AstraZeneca plc., or antigen-binding fragments, conjugates, or variants thereof. In an embodiment, the anti-PD-L1 antibody is an antibody disclosed in U.S. Pat. No. 8,779,108 or U.S. Patent Application Publication No. 2013/0034559, the disclosures of which are specifically incorporated by reference herein. The clinical efficacy of durvalumab (MEDI4736, SEQ ID NO:39 and SEQ ID NO:40) has been described in: Page, Ann. Rev. Med., 2014, 65, 185-202; Brahmer, J. Clin. Oncol. 2014, 32, 5s (supplement, abstract 8021); and McDermott, Cancer Treatment Rev., 2014, 40, 1056-64. The durvalumab (MEDI4736) monoclonal antibody includes a $V_H$ region given by SEQ ID NO:41 (corresponding to SEQ ID NO:72 in U.S. Pat. No. 8,779,108) and a $V_L$ region given by SEQ ID NO:42 (corresponding to SEQ ID NO:77 in U.S. Pat. No. 8,779,108). The durvalumab monoclonal antibody includes disulfide linkages at 22-96, 22"-96", 23'-89', 23'''-89''', 135'-195', 135'''-195''', 148-204, 148"-204", 215'-224, 215'''-224", 230-230", 233-233", 265-325, 265"-325", 371-429, and 371"-429'; and N-glycosylation sites at Asn-301 and Asn-301".

In an embodiment, the anti-PD-L1 antibody is an immunoglobulin G1, anti-(human CD antigen CD274) (human monoclonal heavy chain), disulfide with human monoclonal κ-chain, dimer. In an embodiment, the anti-PD-L1 antibody comprises the heavy and light chains of durvalumab (MEDI4736). In an embodiment, an anti-PD-L1 antibody comprises heavy and light chains having the sequences shown in SEQ ID NO:39 and SEQ ID NO:40, respectively, or antigen binding fragments, variants, or conjugates thereof. In an embodiment, an anti-PD-L1 antibody comprises heavy and light chains that are each at least 99% identical to the sequences shown in SEQ ID NO:39 and SEQ ID NO:40, respectively. In an embodiment, an anti-PD-L1 antibody comprises heavy and light chains that are each at least 98% identical to the sequences shown in SEQ ID NO:39 and SEQ ID NO:40, respectively. In an embodiment, an anti-PD-L1 antibody comprises heavy and light chains that are each at least 97% identical to the sequences shown in SEQ ID NO:39 and SEQ ID NO:40, respectively. In an embodiment, an anti-PD-L1 antibody comprises heavy and light chains that are each at least 96% identical to the sequences shown in SEQ ID NO:39 and SEQ ID NO:40, respectively. In an embodiment, an anti-PD-L1 antibody comprises heavy and light chains that are each at least 95% identical to the sequences shown in SEQ ID NO:39 and SEQ ID NO:40, respectively.

In an embodiment, the anti-PD-L1 antibody comprises $V_H$ and $V_L$ regions having the sequences shown in SEQ ID NO:41 (corresponding to SEQ ID NO: 72 in U.S. Pat. No. 8,779,108) and SEQ ID NO:42 (corresponding to SEQ ID NO: 77 in U.S. Pat. No. 8,779,108), respectively, as described in U.S. Pat. No. 8,779,108 or U.S. Patent Application Publication No. 2013/0034559, the disclosures of which are specifically incorporated by reference herein, including antigen binding fragments, conjugates, and variants thereof. In an embodiment, an anti-PD-L1 antibody comprises $V_H$ and $V_L$ regions that are each at least 99% identical to the sequences shown in SEQ ID NO:41 and SEQ ID NO:42, respectively. In an embodiment, an anti-PD-L1 antibody comprises $V_H$ and $V_L$ regions that are each at least 98% identical to the sequences shown in SEQ ID NO:41 and SEQ ID NO:42, respectively. In an embodiment, an anti-PD-L1 antibody comprises $V_H$ and $V_L$ regions that are each at least 97% identical to the sequences shown in SEQ ID NO:41 and SEQ ID NO:42, respectively. In an embodiment, an anti-PD-L1 antibody comprises $V_H$ and $V_L$ regions that are each at least 96% identical to the sequences shown in SEQ ID NO:41 and SEQ ID NO:42, respectively. In an embodiment, an anti-PD-L1 antibody comprises $V_H$ and $V_L$ regions that are each at least 95% identical to the sequences shown in SEQ ID NO:41 and SEQ ID NO:42, respectively. In an embodiment, an anti-PD-L1 antibody comprises $V_H$ and $V_L$ regions that are each at least 90% identical to the sequences shown in SEQ ID NO:41 and SEQ ID NO:42, respectively.

In another embodiment, the anti-PD-L1 antibody comprises an amino acid sequence comprising a $V_H$ CDR1 having the amino acid sequence of SEQ ID NO:43 (corresponding to SEQ ID NO:23 in U.S. Pat. No. 8,779,108) or conservative amino acid substitutions thereof, a $V_H$ CDR2 having the amino acid sequence of SEQ ID NO:44 (corresponding to SEQ ID NO:24 in U.S. Pat. No. 8,779,108) or conservative amino acid substitutions thereof, a $V_H$ CDR3 having the amino acid sequence of SEQ ID NO:45 (corresponding to SEQ ID NO:25 in U.S. Pat. No. 8,779,108) or conservative amino acid substitutions thereof, a $V_L$ CDR1 having the amino acid sequence of SEQ ID NO:46 (corresponding to SEQ ID NO:28 in U.S. Pat. No. 8,779,108) or conservative amino acid substitutions thereof, a $V_L$ CDR2 having the amino acid sequence of SEQ ID NO:47 (corresponding to SEQ ID NO:29 in U.S. Pat. No. 8,779,108) or conservative amino acid substitutions thereof, and a $V_L$ CDR3 having the amino acid sequence of SEQ ID NO:48 (corresponding to SEQ ID NO:30 in U.S. Pat. No. 8,779,108) or conservative amino acid substitutions thereof, as described in U.S. Pat. No. 8,779,108 or U.S. Patent Application Publication No. 2013/0034559, the disclosures of which are specifically incorporated by reference herein.

In another embodiment, the anti-PD-L1 antibody comprises an amino acid sequence comprising a $V_H$ CDR1 having the amino acid sequence of SEQ ID NO:49 (corresponding to SEQ ID NO:3 in U.S. Pat. No. 8,779,108) or conservative amino acid substitutions thereof, a $V_H$ CDR2 having the amino acid sequence of SEQ ID NO:50 (corresponding to SEQ ID NO:4 in U.S. Pat. No. 8,779,108) or conservative amino acid substitutions thereof, a $V_H$ CDR3 having the amino acid sequence of SEQ ID NO:51 (corresponding to SEQ ID NO:5 in U.S. Pat. No. 8,779,108) or conservative amino acid substitutions thereof, a $V_L$ CDR1 having the amino acid sequence of SEQ ID NO:52 (corresponding to SEQ ID NO:8 in U.S. Pat. No. 8,779,108) or conservative amino acid substitutions thereof, a $V_L$ CDR2 having the amino acid sequence of SEQ ID NO:53 (corresponding to SEQ ID NO:9 in U.S. Pat. No. 8,779,108) or conservative amino acid substitutions thereof, and a $V_L$ CDR3 having the amino acid sequence of SEQ ID NO:54 (corresponding to SEQ ID NO: 10 in U.S. Pat. No. 8,779, 108) or conservative amino acid substitutions thereof, as described in U.S. Pat. No. 8,779,108 or U.S. Patent Application Publication No. 2013/0034559 A1, the disclosures of which are specifically incorporated by reference herein.

In another embodiment, the anti-PD-L1 antibody comprises an amino acid sequence comprising a $V_H$ CDR1 having the amino acid sequence of SEQ ID NO:55 (corresponding to SEQ ID NO: 13 in U.S. Pat. No. 8,779,108) or conservative amino acid substitutions thereof, a $V_H$ CDR2 having the amino acid sequence of SEQ ID NO:56 (corresponding to SEQ ID NO: 14 in U.S. Pat. No. 8,779,108) or conservative amino acid substitutions thereof, a $V_H$ CDR3 having the amino acid sequence of SEQ ID NO:57 (corresponding to SEQ ID NO: 15 in U.S. Pat. No. 8,779,108) or conservative amino acid substitutions thereof, a $V_L$ CDR1 having the amino acid sequence of SEQ ID NO:58 (corresponding to SEQ ID NO: 18 in U.S. Pat. No. 8,779,108) or conservative amino acid substitutions thereof, a $V_L$ CDR2 having the amino acid sequence of SEQ ID NO:59 (corresponding to SEQ ID NO: 19 in U.S. Pat. No. 8,779,108) or conservative amino acid substitutions thereof, and a $V_L$ CDR3 having the amino acid sequence of SEQ ID NO:60 (corresponding to SEQ ID NO: 20 in U.S. Pat. No. 8,779,108) or conservative amino acid substitutions thereof, as described in U.S. Pat. No. 8,779,108 or U.S. Patent Application Publication No. 2013/0034559, the disclosures of which are specifically incorporated by reference herein.

In another embodiment, the anti-PD-L1 antibody comprises an amino acid sequence comprising a $V_H$ CDR1 having the amino acid sequence of SEQ ID NO:61 (corresponding to SEQ ID NO:63 in U.S. Pat. No. 8,779,108) or conservative amino acid substitutions thereof, a $V_H$ CDR2 having the amino acid sequence of SEQ ID NO:62 (corresponding to SEQ ID NO:64 in U.S. Pat. No. 8,779,108) or conservative amino acid substitutions thereof, a $V_H$ CDR3 having the amino acid sequence of SEQ ID NO:63 (corresponding to SEQ ID NO:65 in U.S. Pat. No. 8,779,108) or conservative amino acid substitutions thereof, a $V_L$ CDR1 having the amino acid sequence of SEQ ID NO:64 (corresponding to SEQ ID NO:68 in U.S. Pat. No. 8,779,108) or conservative amino acid substitutions thereof, a $V_L$ CDR2 having the amino acid sequence of SEQ ID NO:65 (corresponding to SEQ ID NO:69 in U.S. Pat. No. 8,779,108) or conservative amino acid substitutions thereof, and a $V_L$ CDR3 having the amino acid sequence of SEQ ID NO:66 (corresponding to SEQ ID NO: 70 in U.S. Pat. No. 8,779,108) or conservative amino acid substitutions thereof, as described in U.S. Pat. No. 8,779,108 or U.S. Patent Application Publication No. 2013/0034559, the disclosures of which are specifically incorporated by reference herein.

In another embodiment, the anti-PD-L1 antibody comprises an amino acid sequence comprising a $V_H$ CDR1 having the amino acid sequence of SEQ ID NO:67 (corresponding to SEQ ID NO:73 in U.S. Pat. No. 8,779,108) or conservative amino acid substitutions thereof, a $V_H$ CDR2 having the amino acid sequence of SEQ ID NO:68 (corresponding to SEQ ID NO:74 in U.S. Pat. No. 8,779,108) or conservative amino acid substitutions thereof, a $V_H$ CDR3 having the amino acid sequence of SEQ ID NO:69 (corresponding to SEQ ID NO:75 in U.S. Pat. No. 8,779,108) or conservative amino acid substitutions thereof, a $V_L$ CDR1 having the amino acid sequence of SEQ ID NO:70 (corresponding to SEQ ID NO:78 in U.S. Pat. No. 8,779,108) or conservative amino acid substitutions thereof, a $V_L$ CDR2 having the amino acid sequence of SEQ ID NO:71 (corresponding to SEQ ID NO:79 in U.S. Pat. No. 8,779,108) or conservative amino acid substitutions thereof, and a $V_L$ CDR3 having the amino acid sequence of SEQ ID NO:72 (corresponding to SEQ ID NO: 80 in U.S. Pat. No. 8,779, 108) or conservative amino acid substitutions thereof, as described in U.S. Pat. No. 8,779,108 or U.S. Patent Application Publication No. 2013/0034559, the disclosures of which are specifically incorporated by reference herein.

In an embodiment, the anti-PD-L1 antibody is atezolizumab, also known as MPDL3280A or RG7446, produced by Genentech, Inc., a subsidiary of Roche, or antigen-binding fragments, conjugates, or variants thereof. In an embodiment, the anti-PD-L1 antibody is an antibody disclosed in U.S. Pat. No. 8,217,149, the disclosure of which is specifically incorporated by reference herein. In an embodiment, the anti-PD-L1 antibody is an antibody disclosed in U.S. Patent Application Publication Nos. 2010/0203056 A1, 2013/0045200 A1, 2013/0045201 A1, 2013/0045202 A1, or 2014/0065135 A1, the disclosures of which are specifically incorporated by reference herein. The atezolizumab monoclonal antibody includes a heavy chain given by SEQ ID NO:73 and a light chain given by SEQ ID NO:74.

In an embodiment, the anti-PD-L1 antibody is an immunoglobulin G1 kappa, anti-(human PD-L1) humanized monoclonal antibody. In an embodiment, the anti-PD-L1 antibody comprises the heavy and light chains of atezolizumab (MPDL3280A). In an embodiment, an anti-PD-L1 antibody comprises heavy and light chains having the sequences shown in SEQ ID NO:73 and SEQ ID NO:74, respectively, or antigen binding fragments, variants, or conjugates thereof. In an embodiment, an anti-PD-L1 antibody comprises heavy and light chains that are each at least 99% identical to the sequences shown in SEQ ID NO:73 and SEQ ID NO:74, respectively. In an embodiment, an anti-PD-L1 antibody comprises heavy and light chains that are each at least 98% identical to the sequences shown in SEQ ID NO:73 and SEQ ID NO:74, respectively. In an embodiment, an anti-PD-L1 antibody comprises heavy and light chains that are each at least 97% identical to the sequences shown in SEQ ID NO:73 and SEQ ID NO:74, respectively. In an embodiment, an anti-PD-L1 antibody comprises heavy and light chains that are each at least 96% identical to the sequences shown in SEQ ID NO:73 and SEQ ID NO:74, respectively. In an embodiment, an anti-PD-L1 antibody comprises heavy and light chains that are each at least 95% identical to the sequences shown in SEQ ID NO:73 and SEQ ID NO:74, respectively.

In an embodiment, the anti-PD-L1 antibody comprises the heavy and light chain CDRs or VRs of atezolizumab (MPDL3280A). In an embodiment, the anti-PD-L1 antibody $V_H$ region comprises the sequence shown in SEQ ID NO:75 (corresponding to SEQ ID NO:20 in U.S. Pat. No. 8,217, 149), and the anti-PD-L1 antibody $V_L$ region comprises the sequence shown in SEQ ID NO:76 (corresponding to SEQ ID NO:21 in U.S. Pat. No. 8,217,149). In an embodiment, an anti-PD-L1 antibody comprises $V_H$ and $V_L$ regions that are each at least 99% identical to the sequences shown in SEQ ID NO:75 and SEQ ID NO:76, respectively. In an embodiment, an anti-PD-L1 antibody comprises $V_H$ and $V_L$ regions that are each at least 98% identical to the sequences shown in SEQ ID NO:75 and SEQ ID NO:76, respectively. In an embodiment, an anti-PD-L1 antibody comprises $V_H$ and $V_L$ regions that are each at least 97% identical to the sequences shown in SEQ ID NO:75 and SEQ ID NO:76, respectively. In an embodiment, an anti-PD-L1 antibody comprises $V_H$ and $V_L$ regions that are each at least 96% identical to the sequences shown in SEQ ID NO:75 and SEQ ID NO:76, respectively. In an embodiment, an anti-PD-L1 antibody comprises $V_H$ and $V_L$ regions that are each at least 95% identical to the sequences shown in SEQ ID NO:75 and SEQ ID NO:76, respectively.

In an embodiment, the anti-PD-L1 antibody is avelumab, also known as MSB0010718C, produced by Merck KGaA/EMD Serono, or antigen-binding fragments, conjugates, or variants thereof. In an embodiment, the anti-PD-L1 antibody is an antibody disclosed in U.S. Patent Application Publication No. US 2014/0341917 A1, the disclosure of which is specifically incorporated by reference herein. The avelumab monoclonal antibody includes a heavy chain of SEQ ID NO:83 and a light chain of SEQ ID NO:84.

In an embodiment, the anti-PD-L1 antibody is an immunoglobulin G1 lambda-1, anti-(human PD-L1) human monoclonal antibody. In an embodiment, the anti-PD-L1 antibody comprises the heavy and light chains of avelumab (MSB0010718C). In an embodiment, an anti-PD-L1 antibody comprises heavy and light chains having the sequences shown in SEQ ID NO:83 and SEQ ID NO:84, respectively, or antigen binding fragments, variants, or conjugates thereof. In an embodiment, an anti-PD-L1 antibody comprises heavy and light chains that are each at least 99% identical to the sequences shown in SEQ ID NO:83 and SEQ ID NO:84, respectively. In an embodiment, an anti-PD-L1 antibody comprises heavy and light chains that are each at least 98% identical to the sequences shown in SEQ ID NO:83 and SEQ ID NO:84, respectively. In an embodiment, an anti-PD-L1 antibody comprises heavy and light chains that are each at least 97% identical to the sequences shown in SEQ ID NO:83 and SEQ ID NO:84, respectively. In an embodiment, an anti-PD-L1 antibody comprises heavy and light chains that are each at least 96% identical to the sequences shown in SEQ ID NO:83 and SEQ ID NO:84, respectively. In an embodiment, an anti-PD-L1 antibody comprises heavy and light chains that are each at least 95% identical to the sequences shown in SEQ ID NO:83 and SEQ ID NO:84, respectively.

In an embodiment, the anti-PD-L1 antibody $V_H$ region comprises the sequence given in SEQ ID NO:85 (corresponding to SEQ ID NO:24 in U.S. Patent Application Publication No. 2014/0341917), and the anti-PD-L1 antibody $V_L$ region comprises the sequence given in SEQ ID NO:86 (corresponding to SEQ ID NO:25 in U.S. Patent Application Publication No. 2014/0341917). In an embodiment, an anti-PD-L1 antibody comprises $V_H$ and $V_L$ regions that are each at least 99% identical to the sequences shown in SEQ ID NO:85 and SEQ ID NO:86, respectively. In an embodiment, an anti-PD-L1 antibody comprises $V_H$ and $V_L$ regions that are each at least 98% identical to the sequences shown in SEQ ID NO:85 and SEQ ID NO:86, respectively. In an embodiment, an anti-PD-L1 antibody comprises $V_H$ and $V_L$ regions that are each at least 97% identical to the sequences shown in SEQ ID NO:85 and SEQ ID NO:86, respectively. In an embodiment, an anti-PD-L1 antibody comprises $V_H$ and $V_L$ regions that are each at least 96% identical to the sequences shown in SEQ ID NO:85 and SEQ ID NO:86, respectively. In an embodiment, an anti-PD-L1 antibody comprises $V_H$ and $V_L$ regions that are each at least 95% identical to the sequences shown in SEQ ID NO:85 and SEQ ID NO:86, respectively.

In an embodiment, the anti-PD-L1 antibody comprises a heavy chain variable region ($V_H$) polypeptide that comprises an HVR-H1, HVR-H2 and HVR-H3 sequence, wherein the HVR-H1 sequence is given by SEQ ID NO:87 (corresponding to SEQ ID NO:15 in U.S. Patent Application Publication No. 2014/0341917) or conservative amino acid substitutions thereof, the HVR-H2 sequence is given by SEQ ID NO:88 (corresponding to SEQ ID NO:16 in U.S. Patent Application Publication No. 2014/0341917) or conservative amino acid substitutions thereof, and the HVR-H3 sequence is given by SEQ ID NO:89 (corresponding to SEQ ID NO: 17 in U.S. Patent Application Publication No. 2014/0341917) or conservative amino acid substitutions thereof, and the anti-PD-L1 antibody also comprises a light chain variable region ($V_L$) polypeptide that comprises an HVR-L1, HVR-L2 and HVR-L3 sequence wherein the HVR-L1 sequence is given by SEQ ID NO:90 (corresponding to SEQ ID NO: 18 in U.S. Patent Application Publication No. 2014/0341917) or conservative amino acid substitutions thereof, the HVR-L2 sequence is given by SEQ ID NO:91 (corresponding to SEQ ID NO: 19 in U.S. Patent Application Publication No. 2014/0341917) or conservative amino acid substitutions thereof, and the HVR-L3 sequence is SEQ ID NO:92 (corresponding to SEQ ID NO:20 in U.S. Patent Application Publication No. 2014/0341917) or conservative amino acid substitutions thereof.

In an embodiment, the anti-PD-L1 antibody is MDX-1105, also known as BMS-935559, which is disclosed in U.S. Pat. No. 7,943,743, the disclosures of which are specifically incorporated by reference herein. In an embodiment, the anti-PD-L1 antibody is selected from the anti-PD-L1 antibodies disclosed in U.S. Pat. No. 7,943,743 which is specifically incorporated by reference herein.

In an embodiment, the anti-PD-L1 antibody is a commercially-available monoclonal antibody, such as INVIVOMAB anti-m-PD-L1 clone 10F.9G2 (BioXCell). A number of commercially-available anti-PD-L1 antibodies are known to one of ordinary skill in the art.

In an embodiment, the anti-PD-L2 antibody is a commercially-available monoclonal antibody, such as BIOLEGEND 24F.10C12 Mouse IgG2a, κ isotype (Biolegend), anti-PD-L2 antibody (Sigma-Aldrich), or other commercially-available anti-PD-L2 antibodies known to one of ordinary skill in the art.

Monoclonal antibodies that inhibit PD-L1 and/or PD-L2 can be prepared by procedures known to those of ordinary knowledge and skill in the art, e.g. by injecting test subjects with PD-L1 or PD-L2 antigen and then isolating hybridomas expressing antibodies having the desired sequence or functional characteristics. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, myeloma cells, or other suitable cells that do not otherwise produce immunoglobulin protein, to obtain the synthesis of monoclonal antibodies in the recombinant host cells. The details of recombinant production of specific antibodies may be found in the references cited in the foregoing, the disclosures of which are incorporated by reference herein. Monoclonal antibodies that inhibit PD-1 can be prepared by standard molecular biology methods using the sequences provided herein by reverse translation and insertion into appropriate DNA or RNA vectors.

The anti-PD-L1 antibody sequences referenced in the foregoing embodiments are summarized in Table 2.

TABLE 2

Anti-PD-L1 antibody amino acid sequences.

| Identifier | Amino Acid Sequence |
| --- | --- |
| SEQ ID NO:39 | durvalumab (MEDI4736)heavy chain |
| SEQ ID NO:40 | durvalumab(MEDI4736) light chain |
| SEQ ID NO:41 | durvalumab(MEDI4736) variable heavy chain |
| SEQ ID NO:42 | durvalumab(MEDI4736) variable light chain |
| SEQ ID NO:43 | durvalumab(MEDI4736) heavy chain CDR1 |

TABLE 2-continued

Anti-PD-L1 antibody amino acid sequences.

| Identifier | Amino Acid Sequence |
| --- | --- |
| SEQ ID NO:44 | durvalumab(MEDI4736) heavy chain CDR2 |
| SEQ ID NO:45 | durvalumab(MEDI4736) heavy chain CDR3 |
| SEQ ID NO:46 | durvalumab(MEDI4736) light chain CDR1 |
| SEQ ID NO:47 | durvalumab(MEDI4736) light chain CDR2 |
| SEQ ID NO:48 | durvalumab(MEDI4736) light chain CDR3 |
| SEQ ID NO:49 | Durvalumab alternative heavy chain CDR15 |
| SEQ ID NO:50 | Durvalumab alternative heavy chain CDR2 |
| SEQ ID NO:51 | Durvalumab alternative heavy chain CDR3 |
| SEQ ID NO:52 | Durvalumab alternative light chain CDR1 |
| SEQ ID NO:53 | Durvalumab alternative light chain CDR2 |
| SEQ ID NO:54 | Durvalumab alternative light chain CDR3 |
| SEQ ID NO:55 | Durvalumab alternative heavy chain CDR1 |
| SEQ ID NO:56 | Durvalumab alternative heavy chain CDR2 |
| SEQ ID NO:57 | Durvalumab alternative heavy chain CDR3 |
| SEQ ID NO:58 | Durvalumab alternative light chain CDR1 |
| SEQ ID NO:59 | Durvalumab alternative light chain CDR2 |
| SEQ ID NO:60 | Durvalumab alternative light chain CDR3 |
| SEQ ID NO:61 | Durvalumab alternative heavy chain CDR1 |
| SEQ ID NO:62 | Durvalumab alternative heavy chain CDR2 |
| SEQ ID NO:63 | Durvalumab alternative heavy chain CDR3 |
| SEQ ID NO:64 | Durvalumab alternative light chain CDR1 |
| SEQ ID NO:65 | Durvalumab alternative light chain CDR2 |
| SEQ ID NO:66 | Durvalumab alternative light chain CDR3 |
| SEQ ID NO:67 | Durvalumab alternative heavy chain CDR1 |
| SEQ ID NO:68 | Durvalumab alternative heavy chain CDR2 |
| SEQ ID NO:69 | Durvalumab alternative heavy chain CDR3 |
| SEQ ID NO:70 | Durvalumab alternative light chain CDR1 |
| SEQ ID NO:71 | Durvalumab alternative light chain CDR2 |
| SEQ ID NO:72 | Durvalumab alternative light chain CDR3 |
| SEQ ID NO:73 | atezolizumab (MPDL3280A) heavy chain |
| SEQ ID NO:74 | Atezolizumab (MPDL3280A) light chain |
| SEQ ID NO:75 | atezolizumab (MPDL3280A) variable heavy chain |
| SEQ ID NO:76 | atezolizumab (MPDL3280A) variable light chain |
| SEQ ID NO:77 | atezolizumab (MPDL3280A) heavy chain HVR-H1 |
| SEQ ID NO:78 | atezolizumab (MPDL3280A) heavy chain HVR-H2 |
| SEQ ID NO:79 | atezolizumab (MPDL3280A) heavy chain HVR-H3 |
| SEQ ID NO:80 | atezolizumab (MPDL3280A) heavy chain HVR-L1 |
| SEQ ID NO:81 | atezolizumab (MPDL3280A) heavy chain HVR-L2 |
| SEQ ID NO:82 | atezolizumab (MPDL3280A) heavy chain HVR-L3 |
| SEQ ID NO:83 | avelumab (MSB0010718C) heavy chain |
| SEQ ID NO:84 | avelumab (MSB0010718C) light chain |
| SEQ ID NO:85 | avelumab (MSB0010718C) variable heavy chain |
| SEQ ID NO:86 | avelumab (MSB0010718C) variable light chain |
| SEQ ID NO:87 | avelumab (MSB0010718C) heavy chain HVR-H1 |
| SEQ ID NO:88 | avelumab (MSB0010718C) heavy chain HVR-H2 |
| SEQ ID NO:89 | avelumab (MSB0010718C) heavy chain HVR-H3 |
| SEQ ID NO:90 | avelumab (MSB0010718C) heavy chain HVR-L1 |
| SEQ ID NO:91 | avelumab (MSB0010718C) heavy chain HVR-L2 |
| SEQ ID NO:92 | avelumab (MSB0010718C) heavy chain HVR-L3 |

In an embodiment, the PD-L1 inhibitor is an anti-PD-L1 antibody. In an embodiment, the PD-L1 inhibitor is selected from the group consisting of Atezolizumab, Avelumab, Durvalumab, BMS-936559 and combinations thereof. In an embodiment, the anti-PD-L1 inhibitor is durvalumab (MEDI4736). In an embodiment, the anti-PD-L1 inhibitor is BMS-936559 (also known as MDX-1105-01). In an embodiment, the anti-PD-L1 inhibitor is Atezolizumab. In an embodiment, the anti-PD-L1 inhibitor is Avelumab.

In an embodiment, the PD-L2 inhibitor is an anti-PD-L2 antibody. In one embodiment, the anti-PD-L2 antibody is rHIgM12B7A.

Interferon (IFN)

IFNs are initially identified for their ability to induce cellular resistance to viral infection, and function as potent mediators in the host defense mechanism and homeostasis, modulating both the innate and adaptive immune responses. IFNs are small, inducible 20-25 K, usually glycosylated proteins that are produced by vertebrate cells in response to various biological stimuli. Mechanistically, IFNs mediate their biological activities by binding to receptors present on the surface of target cells. Specific ligand-receptor interactions trigger intracellular signaling cascade downstream, resulting in the synthesis of proteins that mediate pleiotropic activities. IFNs are classified into three groups: type I, type II or type III, based on their structure, physicochemical properties and biological activities. In mammals, eight families of type I IFN have been described. These are: IFN-α, IFN-β, IFN-δ, IFN-ε, IFN-κ, IFN-ω and IFN-tau (IFN-τ). In an embodiment, the IFNs of the present invention are interferon alpha or alpha interferon (IFN-α). In an embodiment, the IFNs of the present invention are glycosylated. In an embodiment, the IFNs of the present invention are PEGylated.

In some embodiments, the interferon is administered in a dose selected from the group consisting of about 1 million international units (MU) to about 800 MU, from about 1 MU to about 10 MU, from about 20 MU to about 40 MU, from about 2 MU to about 15 MU, from about 5 MU to about 25 MU, from about 50 MU to about 100 MU, from about 150 MU to about 250 MU, from about 300 MU to about 400 MU, and from about 500 MU to about 600 MU.

In some embodiments, the interferon is administered in a dose selected from the group consisting of from about 0.1 μg/day to about 1 mg/day, from about 10 μg/day to about 200 μg/day, from about 20 μg/day to about 150 μg/day, from about 0.1 μg/day to about 125 μg/day, from about 1 μg/day to about 20 μg/day, and about 4.5 μg/day to about 30 μg/day.

In some embodiments, the interferon is administered in a dose selected from the group consisting of 1, 2, 3, 4, 5, 6, 7, 8, 9, 10, 11, 12, 13, 14, 15, 16, 17, 18 19, 20, 21, 22, 23, 24, 25, 26, 27, 28, 29, and 30 MU/m$^2$.

In some embodiments, the interferon is PEGylated.

In some embodiments, the interferon is glycosylated.

rIFN-alpha 2b

In an embodiment, the IFN is recombinant interferon alpha-2b (rIFN-alpha2b). In an embodiment, the IFN is recombinant interferon alpha-2b with the trade name Intron A from Merck Sharp & Dohme Limited. rIFN-alpha 2b is a type I interferon consisting of 165 amino acid residues with arginine in position 23. This protein is produced by recombinant DNA technology and resembles interferon secreted by leukocytes. In an embodiment, the IFN is an interferon having the sequence set forth in SEQ ID NO: 93 or fragment, variant, conjugates or biosimilar thereof.

PEGylated rIFN-Alpha 2b

In an embodiment, the IFN is PEGylated rIFN-alpha 2b. In an embodiment, the IFN is PEGylated rIFN-alpha 2b with the trade name PEG-Intron from Merck Sharp & Dohme Limited. PEGylated rIFN-alpha 2b is derived from recombinant human interferon's alfa-2b moiety. It binds to and activates human type 1 interferon receptors causing them to dimerize.

rIFN-alpha 2a

In an embodiment, the IFN is recombinant interferon alpha-2a (rIFN-alpha2a). In an embodiment, the IFN is recombinant interferon alpha-2a with the trade name Roferon-A from Hoffmann La Roche. rIFN-alpha 2ab is a type I interferon consisting of 165 amino acid residues with lysine in position 23. This protein is produced by recombinant DNA technology and resembles interferon secreted by leukocytes. In an embodiment, the IFN is an interferon having the sequence set forth in SEQ ID NO: 94 or fragment, variant, conjugates or biosimilar thereof.

PEGylated rIFN-Alpha 2a

In an embodiment, the IFN is PEGylated rIFN-alpha 2a. In an embodiment, the IFN is PEGylated rIFN-alpha 2a with the trade name Pegasys from Hoffmann La Roche. PEGylated rIFN-alpha 2a is derived from recombinant human interferon's alfa-2a moiety. It binds to and activates human type 1 interferon receptors causing them to dimerize.

Interferon Alpha

In an embodiment, the IFN is interferon alpha, also named as natural alpha interferon. Interferon alfa contains several naturally occurring IFN-α subtypes and is purified by affinity chromatography. Interferon alpha proteins are mainly involved in innate immune response against viral infection. They come in 13 subtypes that are called IFN-α 1, IFN-α 2, IFN-α 4, IFN-α5, IFN-α 6, IFN-α 7, IFN-α 8, IFN-α 10, IFN-α 13, IFN-α 14, IFN-α 16, IFN-α 17, IFN-α 21. In an embodiment, the IFN is interferon alpha with the trade name Multiferon from Swedish Orphan Biovitrim. Multiferon consists of the 6 major subtypes are IFN-α1, IFN-α2, IFN-α8, IFN-α10, IFN-α14 and IFN-α21. Of these, IFN-α2 and IFN-α14 are glycosylated. In an embodiment, the IFN is interferon alpha selected from the group consisting of IFN-α 1, IFN-α 2, IFN-α 4, IFN-α 5, IFN-α 6, IFN-α 7, IFN-α 8, IFN-α 10, IFN-α 13, IFN-α 14, IFN-α 16, IFN-α 17, IFN-α 21, and combinations thereof. In an embodiment, the IFN is interferon alpha selected from the group consisting of IFN-α1, IFN-α2, IFN-α8, IFN-α10, IFN-α14, α21, and combinations thereof. In an embodiment, the IFN is IFN-α1. In an embodiment, the IFN an interferon having the sequence set forth in SEQ ID NO: 95 or fragment, variant, conjugates or biosimilar thereof.

In an embodiment, the IFN is IFN-α2. In an embodiment, the IFN an interferon having the sequence set forth in SEQ ID NO: 96 or fragment, variant, conjugates or biosimilar thereof.

In an embodiment, the IFN is IFN-α8. In an embodiment, the IFN an interferon having the sequence set forth in SEQ ID NO: 97 or fragment, variant, conjugates or biosimilar thereof.

In an embodiment, the IFN is IFN-α10. In an embodiment, the IFN an interferon having the sequence set forth in SEQ ID NO: 98 or fragment, variant, conjugates or biosimilar thereof.

In an embodiment, the IFN is IFN-α14. In an embodiment, the IFN an interferon having the sequence set forth in SEQ ID NO: 99 or fragment, variant, conjugates or biosimilar thereof.

In an embodiment, the IFN is IFN-α21. In an embodiment, the IFN an interferon having the sequence set forth in SEQ ID NO: 100 or fragment, variant, conjugates or biosimilar thereof Interferon Alfacon-1

In an embodiment, the IFN is interferon alfacon-1. Interferon alfacon-1 is a recombinant non-naturally occurring type-I interferon. The 166-amino acid sequence of Interferon alfacon-1 was derived by scanning the sequences of several natural interferon alpha subtypes and assigning the most frequently observed amino acid in each corresponding position. Four additional amino acid changes were made to facilitate the molecular construction, and a corresponding synthetic DNA sequence was constructed using chemical synthesis methodology. Interferon alfacon-1 differs from interferon alfa-2b at 20/166 amino acids (88% homology), and comparison with interferon-beta shows identity at over 30% of the amino acid positions. In an embodiment, the IFN is interferon alfacon-1 under the trade name Infergen from Three Rivers Pharmaceuticals LLC. In an embodiment, the IFN an interferon having the sequence set forth in SEQ ID NO: 101 or fragment, variant, conjugates or biosimilar thereof.

Interferon Alfa-n1

In an embodiment, the IFN is interferon alfa-n1, also named as interferon alpha-2, or interferon alpha-A. Interferon alfa-n1 is a purified, natural (n is for natural) glycosylated human interferon alpha protein having 166 residues. In an embodiment, the IFN is interferon alfa-n1 under the trade name Wellferon from The Wellcome Foundation Ltd. In an embodiment, the IFN an interferon having the sequence set forth in SEQ ID NO: 102 or fragment, variant, conjugates or biosimilar thereof.

Interferon Alfa-n3

In an embodiment, the IFN is interferon alfa-n3. Interferon alfa-n3 is a purified, natural (n is for natural) human interferon alpha proteins (consists of 3 forms or polymorphisms including interferon alfa-2a, 2b and 2c, set forth in SEQ ID Nos: 103-106 respectively), having 166 residues, and some are glycosylated. In an embodiment, the IFN is interferon alfa-n3 under the trade name Alferon from Hemispherx Biopharma. In an embodiment, the IFN an interferon having the sequence set forth in SEQ ID NO: 103 or fragment, variant, conjugates or biosimilar thereof. In an embodiment, the IFN an interferon having the sequence set forth in SEQ ID NO: 104 or fragment, variant, conjugates or biosimilar thereof. In an embodiment, the IFN an interferon having the sequence set forth in SEQ ID NO: 105 or fragment, variant, conjugates or biosimilar thereof. In an embodiment, the IFN an interferon having the sequence set forth in SEQ ID NO: 106 or fragment, variant, conjugates or biosimilar thereof.

Albinterferon Alpha-2b

In an embodiment, the IFN is albinterferon alpha-2b, also referred as Albumin-interferon alpha or alb-IFN. Albumin-interferon alpha (Albuferon) is a novel, long-acting form of interferon alpha. In an embodiment, the IFN is albinterferon alpha-2b under the trade name Albuferon from Human Genome Sciences.

IFN Alpha-2b XL

In an embodiment, the IFN is IFN alpha-2b XL, referred as interferon alpha-2b controlled-release from Avadel Pharmaceuticals.

BLX-883

In an embodiment, the IFN is BLX-883, also referred as Locteron. BLX-883 is a form of alfa interferon from Biolex Therapeutics, and has been under clinical investigation (NCT00863239, NCT00953589, and NCT00593151).

AVI-005

In an embodiment, the IFN is AVI-005. AVI-005 is a form of glycosylated interferon alpha-2b from AviGenics Inc.

Belerofon

In an embodiment, the IFN is belerofon. Belerofon is a form of long-lasting human interferon alpha from Nautilus Biotech.

Cepeginterferon Alfa-2b

In an embodiment, the IFN is Cepeginterferon alfa-2b. Cepeginterferon alfa-2b is a long-acting PEGylated interferon alfa 2b that is developed by Biocad and is under clinical investigation (NCT01889433).

PI3K Inhibitors

The PI3K inhibitor may be any PI3K inhibitor known in the art. In particular, it is one of the PI3K inhibitors described in more detail in the following paragraphs. Preferably, it is a PI3K inhibitor selected from the group consisting of a PI3K-γ inhibitor, a PI3K-δ inhibitor, and a PI3K-γ,δ inhibitor. In one specific embodiment, it is a PI3K-δ inhibitor. For avoidance of doubt, references herein to a PI3K inhibitor may refer to a compound or a pharmaceutically acceptable salt, ester, solvate, hydrate, cocrystal, or prodrug thereof.

In an embodiment, the PI3K inhibitor, which is preferably selected from the group consisting of a PI3K-γ inhibitor, a PI3K-δ inhibitor, and a PI3K-γ,δ inhibitor, is a compound selected from the structures disclosed in U.S. Pat. Nos. 8,193,182 and 8,569,323, and U.S. Patent Application Publication No. 2012/0184568, 2013/0344061, and 2013/0267521, the disclosures of which are incorporated by reference herein.

In an embodiment, the PI3K-γ,δ inhibitor is a compound of Formula (III-A):

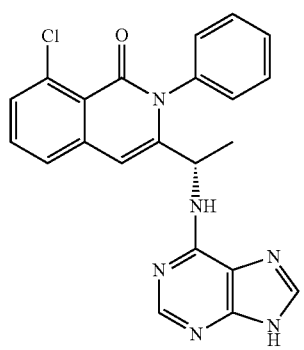

Formula (III-A)

or a pharmaceutically acceptable salt, solvate, hydrate, cocrystal, or prodrug thereof. Formula (III-A) is also known as IPI-145 or duvelisib (Infinity Pharmaceuticals) and has been studied at doses of 5 mg and 25 mg in clinical trials, including those described in Flinn, *Blood*, 2014, 124, 802, and O'Brien, *Blood*, 2014, 124, 3334.

In an embodiment, the PI3K inhibitor is a compound of Formula (IV):

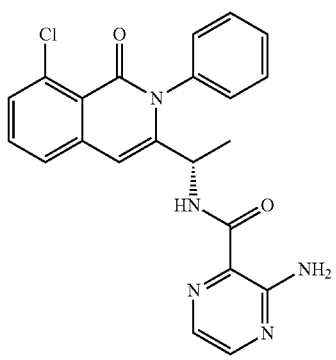

Formula (IV)

or a pharmaceutically acceptable salt, solvate, hydrate, cocrystal, or prodrug thereof.

In a preferred embodiment, the PI3K inhibitor is (S)-3-(1-((9H-purin-6-yl)amino)ethyl)-8-chloro-2-phenylisoquinolin-1(2H)-one or a pharmaceutically acceptable salt, solvate, hydrate, cocrystal, or prodrug thereof.

In an embodiment, the PI3K inhibitor is (S)-3-amino-N-(1-(5-chloro-4-oxo-3-phenyl-3,4-dihydroquinazolin-2-yl)ethyl)pyrazine-2-carboxamide or a pharmaceutically acceptable salt, solvate, hydrate, cocrystal, or prodrug thereof.

In an embodiment, the PI3K inhibitor (which may be a PI3K-γ inhibitor, PI3K-δ inhibitor, or PI3K-γ,δ inhibitor) is a compound selected from the structures disclosed in U.S. Pat. Nos. 8,193,199, 8,586,739, and 8,901,135, the disclosure of each of which is incorporated by reference herein.

In an embodiment, the PI3K-δ inhibitor is a compound of Formula (IX):

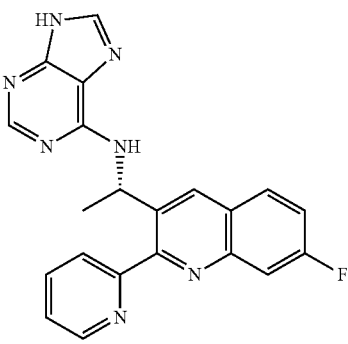

Formula (IX)

or a pharmaceutically acceptable salt, solvate, hydrate, cocrystal, or prodrug thereof.

In an embodiment, the PI3K inhibitor or PI3K-δ inhibitor is (S)—N-(1-(7-fluoro-2-(pyridin-2-yl)quinolin-3-yl)ethyl)-9H-purin-6-amine or a pharmaceutically acceptable salt, solvate, hydrate, cocrystal, or prodrug thereof.

In an embodiment, the PI3K-δ inhibitor is a compound of Formula (X):

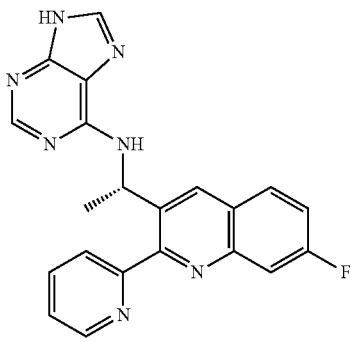

Formula (X)

or a pharmaceutically acceptable salt, solvate, hydrate, cocrystal, or prodrug thereof.

In an embodiment, the PI3K inhibitor or PI3K-δ inhibitor is (S)—N-(1-(6-fluoro-3-(pyridin-2-yl)quinoxalin-2-yl)ethyl)-9H-purin-6-amine or a pharmaceutically acceptable salt, solvate, hydrate, cocrystal, or prodrug thereof.

In an embodiment, the PI3K-δ inhibitor is a compound of Formula (XI):

Formula (XI)

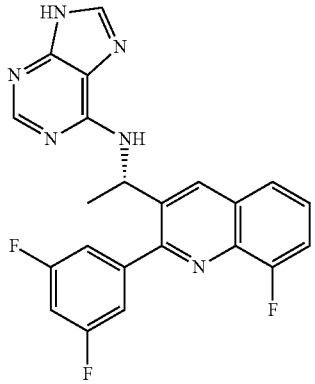

or a pharmaceutically acceptable salt, solvate, hydrate, cocrystal, or prodrug thereof.

In an embodiment, the PI3K-δ inhibitor is (S)—N-(1-(2-(3,5-difluorophenyl)-8-fluoroquinolin-3-yl)ethyl)-9H-purin-6-amine or a pharmaceutically-acceptable salt, solvate, hydrate, cocrystal, or prodrug thereof.

In an embodiment, the PI3K-δ inhibitor is a compound of Formula (XII):

Formula (XII)

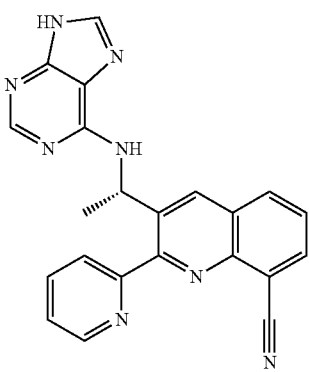

or a pharmaceutically acceptable salt, solvate, hydrate, cocrystal, or prodrug thereof.

In an embodiment, the PI3K-δ inhibitor is (S)-3-(1-((9H-purin-6-yl)amino)ethyl)-2-(pyridin-2-yl)quinoline-8-carbonitrile or a pharmaceutically acceptable salt, solvate, hydrate, cocrystal, or prodrug thereof.

In an embodiment, the PI3K-δ inhibitor is a compound of Formula (XIII):

Formula (XIII)

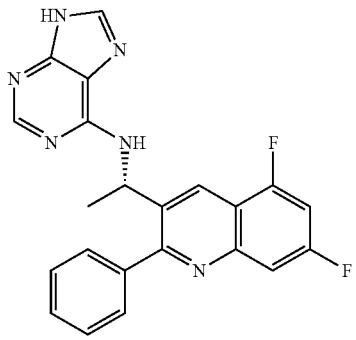

or a pharmaceutically acceptable salt, solvate, hydrate, cocrystal, or prodrug thereof.

In an embodiment, the PI3K-δ inhibitor is (S)—N-(1-(5,7-difluoro-2-(pyridin-2-yl)quinolin-3-yl)ethyl)-9H-purin-6-amine or a pharmaceutically acceptable salt, solvate, hydrate, cocrystal, or prodrug thereof.

In an embodiment, the PI3K inhibitor (which may be a PI3K-γ inhibitor, PI3K-δ inhibitor, or PI3K-γ,δ inhibitor) is idelalisib. In an embodiment, the PI3K inhibitor (which may be a PI3K-γ inhibitor, PI3K-δ inhibitor, or PI3K-γ,δ inhibitor) is the compound of Formula (XVI).

Formula (XVI)

or a pharmaceutically acceptable salt, solvate, hydrate, cocrystal, or prodrug thereof.

In an embodiment, the PI3K inhibitor (which may be a PI3K-γ inhibitor, PI3K-δ inhibitor, or PI3K-γ,δ inhibitor) is (S)-2-(1-((9H-purin-6-yl)amino)propyl)-5-fluoro-3-phenylquinazolin-4(3H)-one or a pharmaceutically acceptable salt, solvate, hydrate, cocrystal, or prodrug thereof.

In an embodiment, the PI3K inhibitor (which may be a PI3K-γ inhibitor, PI3K-δ inhibitor, or PI3K-γ,δ inhibitor) is 4(3H)-quinazolinone, 5-fluoro-3-phenyl-2-[(1S)-1-(9H-purin-6-ylamino)propyl]-5-fluoro-3-phenyl-2-{(1S)-1-[(7H-purin-6-yl)amino]propyl}quinazolin-4(3H)-one or a pharmaceutically acceptable salt, solvate, hydrate, cocrystal, or prodrug thereof.

Other PI3K inhibitors suitable for use in the described combination with a BTK inhibitor also include, but are not limited to, those described in, for example, U.S. Pat. No. 8,193,182 and U.S. Published Application No. 2013/0267521; 2013/0053362; 2013/0029984; 2013/0029982;

2012/0184568; and 2012/0059000, the disclosures of each of which are incorporated by reference in their entireties.

Buparlisib

In an embodiment, the PI3K inhibitor is Buparlisib. Buparlisib has the chemical structure and name shown as: 5-(2,6-dimorpholin-4-ylpyrimidin-4-yl)-4-(trifluoromethyl)pyridin-2-amine

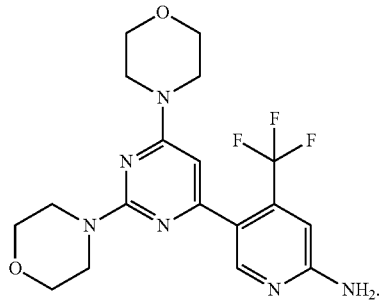 [SMILES: Nc1cc(C(F)(F)F)c(-c2cc(N3CCOCC3)nc(N3CCOCC3)n2)cn1]

Alpelisib

In an embodiment, the PI3K inhibitor is Alpelisib. Alpelisib has the chemical structure and name shown as: (2S)-1-N-[4-methyl-5-[2-(1,1,1-trifluoro-2-methylpropan-2-yl)pyridin-4-yl]-1,3-thiazol-2-yl]pyrrolidine-1,2-dicarboxamide

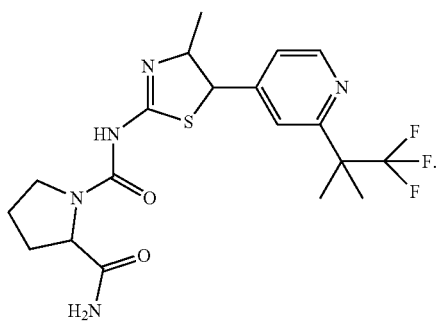 [SMILES: CC1N=C(NC(=O)N2CCCC2C(N)=O)SC1c1ccnc(C(C)(C)C(F)(F)F)c1]

Pictilisib

In an embodiment, the PI3K inhibitor is Pictilisib. Pictilisib has the chemical structure and name shown as: 4-[2-(1H-indazol-4-yl)-6-[(4-methylsulfonylpiperazin-1-yl)methyl]thieno[3,2-d]pyrimidin-4-yl]morpholine

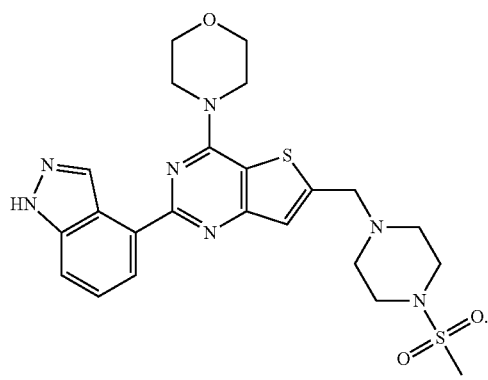 [SMILES: CS(=O)(=O)N1CCN(Cc2cc3nc(-c4cccc5[nH]ncc45)nc(N4CCOCC4)c3s2)CC1]

Pilaralisib

In an embodiment, the PI3K inhibitor is Pilaralisib. Pilaralisib has the chemical structure and name shown as: 2-amino-N-[3-[[3-(2-chloro-5-methoxyanilino)quinoxalin-2-yl]sulfamoyl]phenyl]-2-methylpropanamide

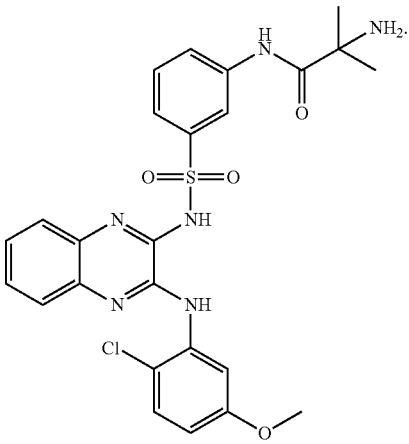 [SMILES: COc1ccc(Cl)c(Nc2nc3ccccc3nc2NS(=O)(=O)c2cccc(NC(=O)C(C)(C)N)c2)c1]

Sonolisib

In an embodiment, the PI3K inhibitor is Sonolisib. Sonolisib has the chemical structure and name shown as: (4S,4aR,5R,6aS,9aR,E)-1-((diallylamino)methylene)-11-hydroxy-4-(methoxymethyl)-4a,6a-dimethyl-2,7,10-trioxo-1,2,4,4a,5,6,6a,7,8,9,9a,10-dodecahydroindeno[4,5-h]isochromen-5-yl acetate

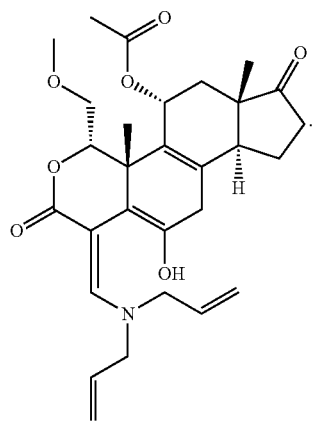 [SMILES: C=CCN(/C=C1/C(=O)O[C@H](COC)[C@@]2(C)C1=C(O)CC1=C2[C@H](OC(C)=O)C[C@]2(C)C(=O)CC[C@@H]12)CC=C]

Copanlisib

In an embodiment, the PI3K inhibitor is Copanlisib. Copanlisib has the chemical structure and name shown as: 2-amino-N-(7-methoxy-8-(3-morpholinopropoxy)-2,3-dihydroimidazo[1,2-c]quinazolin-5-yl)pyrimidine-5-carboxamide

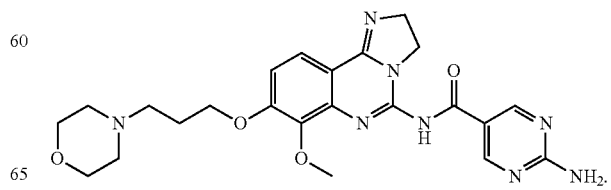

CH5132799

In an embodiment, the PI3K inhibitor is CH5132799. CH5132799 has the chemical structure and name shown as: 5-(7-methylsulfonyl-2-morpholin-4-yl-5,6-dihydropyrrolo[2,3-d]pyrimidin-4-yl)pyrimidin-2-amine

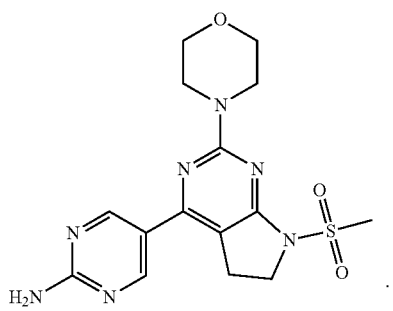 [SMILES: CS(=O)(=O)N1CCc2c(-c3cnc(N)nc3)nc(N3CCOCC3)nc21]

Serabelisib

In an embodiment, the PI3K inhibitor is Serabelisib. Serabelisib has the chemical structure and name shown as: [6-(2-amino-1,3-benzoxazol-5-yl)imidazo[1,2-a]pyridin-3-yl]-morpholin-4-ylmethanone

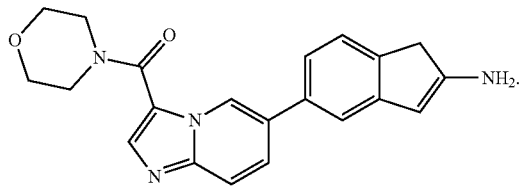 [SMILES: NC1=Cc2cc(-c3ccc4ncc(C(=O)N5CCOCC5)n4c3)ccc2C1]

AZD8186

In an embodiment, the PI3K inhibitor is AZD8186. AZD8186 has the chemical structure and name shown as: 8-[(1R)-1-(3,5-difluoroanilino)ethyl]-N,N-dimethyl-2-morpholin-4-yl-4-oxochromene-6-carboxamide

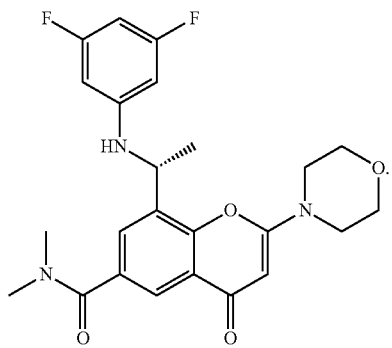 [SMILES: C[C@@H](Nc1cc(F)cc(F)c1)c1cc(C(=O)N(C)C)cc2c(=O)cc(N3CCOCC3)oc12]

SAR260301

In an embodiment, the PI3K inhibitor is SAR260301. SAR260301 has the chemical structure and name shown as: (S)-2-(2-(2-methylindolin-1-yl)-2-oxoethyl)-6-morpholino-pyrimidin-4(3H)-one

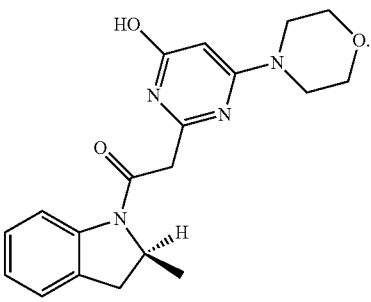 [SMILES: C[C@H]1Cc2ccccc2N1C(=O)Cc1nc(O)cc(N2CCOCC2)n1]

GSK2636771

In an embodiment, the PI3K inhibitor is GSK2636771. GSK2636771 has the chemical structure and name shown as: 2-methyl-1-(2-methyl-3-(trifluoromethyl)benzyl)-6-morpholino-1H-benzo[d]imidazole-4-carboxylic acid

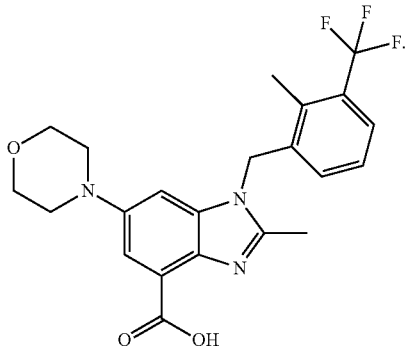 [SMILES: Cc1c(Cn2c(C)nc3c(C(=O)O)cc(N4CCOCC4)cc32)cccc1C(F)(F)F]

Idelalisib

In an embodiment, the PI3K inhibitor is Idelalisib. Idelalisib has the chemical structure and name shown as: (S)-2-(1-((9H-purin-6-yl)amino)propyl)-5-fluoro-3-phenylquinazolin-4(3H)-one

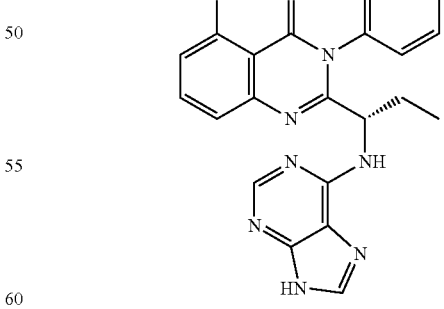

AMG319

In an embodiment, the PI3K inhibitor is AMG319. AMG319 has the chemical structure and name shown as: N-[(1S)-1-(7-fluoro-2-pyridin-2-ylquinolin-3-yl)ethyl]-7H-purin-6-amine

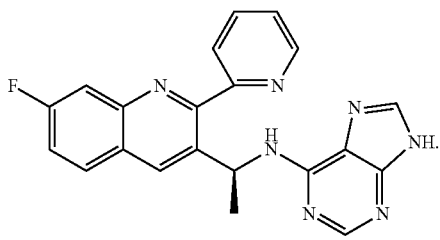 [SMILES: C[C@H](Nc1ncnc2[nH]cnc12)c1cc2ccc(F)cc2nc1-c1ccccn1]

Acalisib

In an embodiment, the PI3K inhibitor is Acalisib. Acalisib has the chemical structure and name shown as: 6-fluoro-3-phenyl-2-[(1S)-1-(7H-purin-6-ylamino)ethyl]quinazolin-4-one

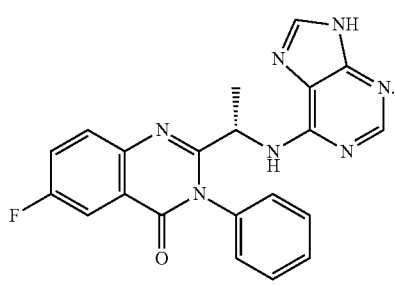 [SMILES: C[C@H](Nc1ncnc2[nH]cnc12)c1nc2ccc(F)cc2c(=O)n1-c1ccccc1]

Duvelisib

In an embodiment, the PI3K inhibitor is Duvelisib. Duvelisib has the chemical structure and name shown as: 8-chloro-2-phenyl-3-[(1S)-1-(7H-purin-6-ylamino)ethyl]isoquinolin-1-one

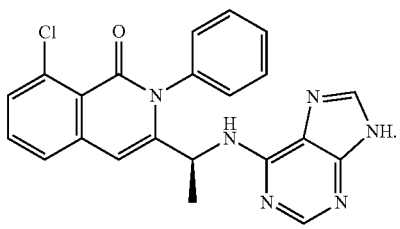 [SMILES: C[C@H](Nc1ncnc2[nH]cnc12)c1cc2cccc(Cl)c2c(=O)n1-c1ccccc1]

Taselisib

In an embodiment, the PI3K inhibitor is Taselisib. Taselisib has the chemical structure and name shown as: 2-methyl-2-[4-[2-(5-methyl-2-propan-2-yl-1,2,4-triazol-3-yl)-5,6-dihydroimidazo[1,2-d][1,4]benzoxazepin-9-yl]pyrazol-1-yl]propanamide

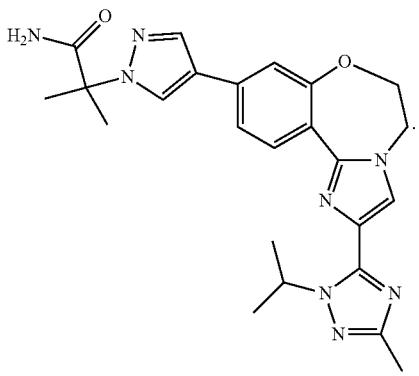 [SMILES: Cc1nc(-c2cn3c(n2)-c2ccc(-c4cnn(C(C)(C)C(N)=O)c4)cc2OCC3)n(C(C)C)n1]

GDC-0084

In an embodiment, the PI3K inhibitor is GDC-0084. GDC-0084 has the chemical structure and name shown as: 5-(6,6-dimethyl-4-morpholin-4-yl-8,9-dihydropurino[8,9-c][1,4]oxazin-2-yl)pyrimidin-2-amine

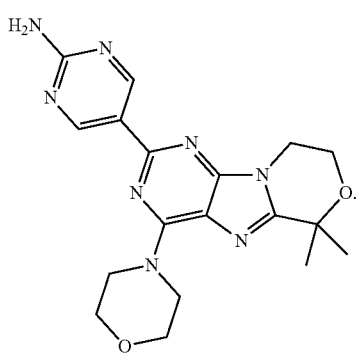 [SMILES: CC1(C)OCCn2c1nc1c(N3CCOCC3)nc(-c3cnc(N)nc3)nc12]

AKT Inhibitors

SB-203580

In an embodiment, the AKT inhibitor is SB-203580. SB-203580 has the chemical structure and name shown as: 4-[4-(4-fluorophenyl)-2-(4-methylsulfinylphenyl)-1H-imidazol-5-yl]pyridine

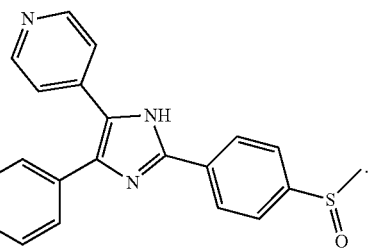

MK-2206

In an embodiment, the AKT inhibitor is MK-2206. MK-2206 has the chemical structure and name shown as: 8-[4-(1-aminocyclobutyl)phenyl]-9-phenyl-2H-[1,2,4]triazolo[3,4-f][1,6]naphthyridin-3-one

SC79

In an embodiment, the AKT inhibitor is SC79. SC79 has the chemical structure and name shown as: ethyl 2-amino-6-chloro-4-(1-cyano-2-ethoxy-2-oxoethyl)-4H-chromene-3-carboxylate

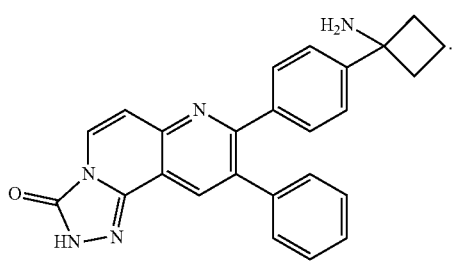 [SMILES: NC1(c2ccc(-c3nc4ccn5c(=O)[nH]nc5c4cc3-c3ccccc3)cc2)CCC1]

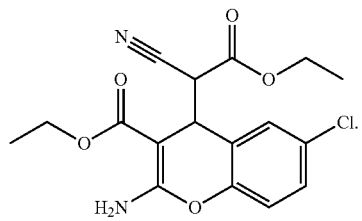 [SMILES: CCOC(=O)C1=C(N)Oc2ccc(Cl)cc2C1C(C#N)C(=O)OCC]

AZD5363

In an embodiment, the AKT inhibitor is AZD5363. AZD5363 has the chemical structure and name shown as: 4-amino-N-[(1S)-1-(4-chlorophenyl)-3-hydroxypropyl]-1-(7H-pyrrolo[2,3-d]pyrimidin-4-yl)piperidine-4-carboxamide

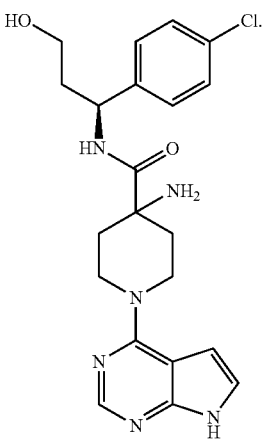 [SMILES: NC1(C(=O)N[C@@H](CCO)c2ccc(Cl)cc2)CCN(c2ncnc3[nH]ccc23)CC1]

Miltefosine

In an embodiment, the AKT inhibitor is Miltefosine. Miltefosine has the chemical structure and name shown as: hexadecyl 2-(trimethylazaniumyl)ethyl phosphate

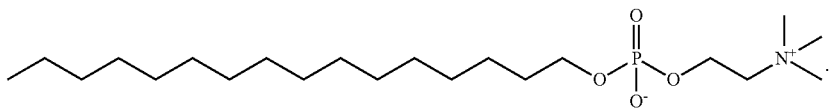 [SMILES: CCCCCCCCCCCCCCCCOP(=O)([O-])OCC[N+](C)(C)C]

Perifosine

In an embodiment, the AKT inhibitor is Perifosine. Perifosine has the chemical structure and name shown as: (1,1-dimethylpiperidin-1-ium-4-yl) octadecyl phosphate

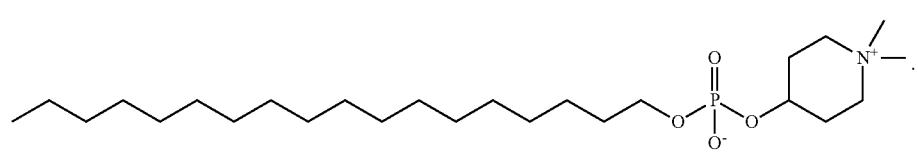 [SMILES: CCCCCCCCCCCCCCCCCCOP(=O)([O-])OC1CC[N+](C)(C)CC1]

PF-04691502

In an embodiment, the AKT inhibitor is PF-04691502. PF-04691502 has the chemical structure and name shown as: 2-amino-8-[4-(2-hydroxyethoxy)cyclohexyl]-6-(6-methoxypyridin-3-yl)-4-methylpyrido[2,3-d]pyrimidin-7-one

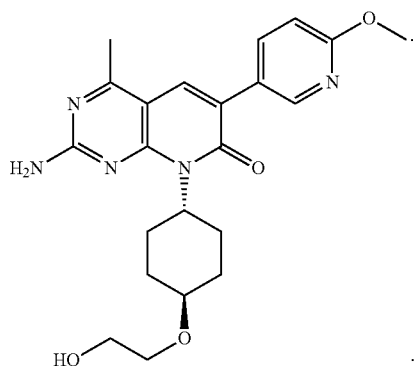 [SMILES: COc1ccc(-c2cc3c(C)nc(N)nc3n([C@H]3CC[C@H](OCCO)CC3)c2=O)cn1]

CCT128930

In an embodiment, the AKT inhibitor is CCT128930. CCT128930 has the chemical structure and name shown as: 4-[(4-chlorophenyl)methyl]-1-(7H-pyrrolo[2,3-d]pyrimidin-4-yl)piperidin-4-amine

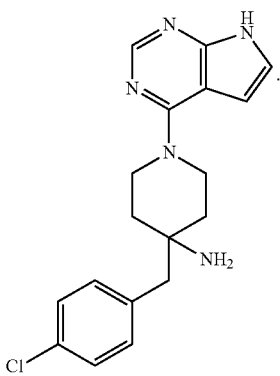 [SMILES: NC1(Cc2ccc(Cl)cc2)CCN(c2ncnc3[nH]ccc23)CC1]

A-674563

In an embodiment, the AKT inhibitor is A-674563. A-674563 has the chemical structure and name shown as: (2S)-1-[5-(3-methyl-2H-indazol-5-yl)pyridin-3-yl]oxy-3-phenylpropan-2-amine

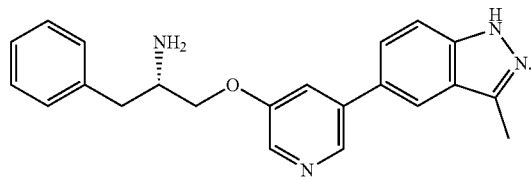 [SMILES: Cc1n[nH]c2ccc(-c3cncc(OC[C@@H](N)Cc4ccccc4)c3)cc12]

RX-0201 (Archexin)

In an embodiment, the AKT inhibitor is RX-0201 (Archexin). In an embodiment, the AKT inhibitor is an oligodeoxynucleotide with the sequence of 5' gctgcatgatctccttggcg 3'.

PBI-05204 (Oleandrin)

In an embodiment, the AKT inhibitor is PBI-05204 (Oleandrin). PBI-05204 has the chemical structure and name shown as: [(3S,5R,8R,9S,10S,13R,14S,16S,17R)-14-hydroxy-3-[(2R,4S,5S,6S)-5-hydroxy-4-methoxy-6-methyloxan-2-yl]oxy-10,13-dimethyl-17-(5-oxo-2H-furan-3-yl)-1,2,3,4,5,6,7,8,9,11,12,15,16,17-tetradecahydrocyclopenta[a]phenanthren-16-yl]acetate

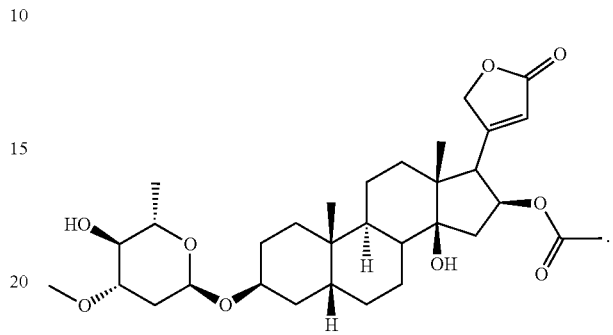

AKT Inhibitor VIII

In an embodiment, the AKT inhibitor is AKT inhibitor VIII. AKT inhibitor VIII has the chemical structure and name shown as: 3-[1-[[4-(7-phenyl-3H-imidazo[4,5-g]quinoxalin-6-yl)phenyl]methyl]piperidin-4-yl]-1H-benzimidazol-2-one

AT7867

In an embodiment, the AKT inhibitor is AT7867. AT7867 has the chemical structure and name shown as: 4-(4-chlorophenyl)-4-[4-(1H-pyrazol-4-yl)phenyl]piperidine

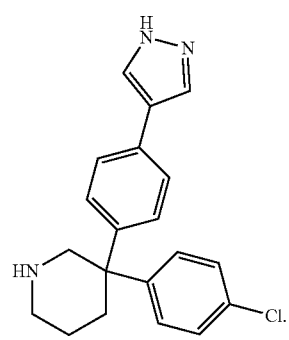 [SMILES: Clc1ccc(C2(c3ccc(-c4cn[nH]c4)cc3)CCCNC2)cc1]

AT13148

In an embodiment, the AKT inhibitor is AT13148. AT13148 has the chemical structure and name shown as: (1S)-2-amino-1-(4-chlorophenyl)-1-[4-(1H-pyrazol-4-yl)phenyl]ethanol

GDC-0068 (I.patasertib)

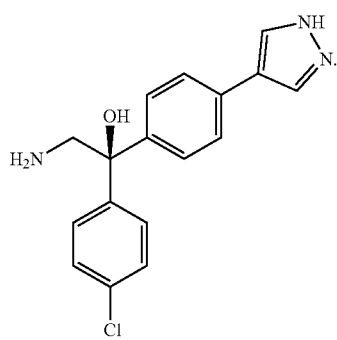 [SMILES: NC[C@@](O)(c1ccc(Cl)cc1)c1ccc(-c2cn[nH]c2)cc1]

In an embodiment, the AKT inhibitor is GDC-0068 (Ipatasertib). GDC-0068 has the chemical structure and name shown as: (S)-2-(4-Chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one

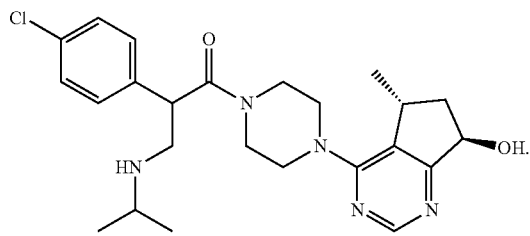 [SMILES: CC(C)NCC(C(=O)N1CCN(c2ncnc3c2[C@H](C)C[C@H]3O)CC1)c1ccc(Cl)cc1]

TIC10

In an embodiment, the AKT inhibitor is TIC10. TIC10 has the chemical structure and name shown as: 7-benzyl-4-(2-methylbenzyl)-1,2,6,7,8,9-hexahydroimidazo[1,2-a]pyrido[3,4-e]pyrimidin-5(4H)-one

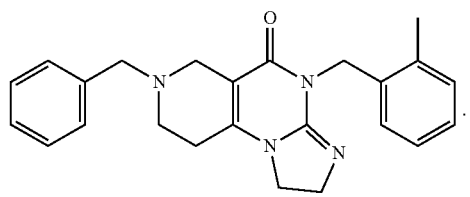 [SMILES: Cc1ccccc1CN1C(=O)C2=C(CCN(Cc3ccccc3)C2)N2CCN=C12]

SC79

In an embodiment, the AKT inhibitor is SC79. SC79 has the chemical structure and name shown as: ethyl 2-amino-6-chloro-4-(1-cyano-2-ethoxy-2-oxoethyl)-4H-chromene-3-carboxylate

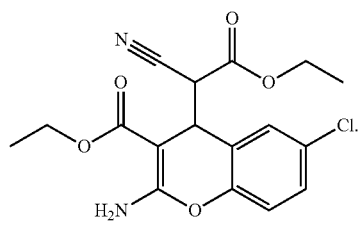 [SMILES: CCOC(=O)C1=C(N)Oc2ccc(Cl)cc2C1C(C#N)C(=O)OCC]

GSK690693

In an embodiment, the AKT inhibitor is GSK690693. GSK690693 has the chemical structure and name shown as: 4-[2-(4-amino-1,2,5-oxadiazol-3-yl)-1-ethyl-7-[[(3S)-piperidin-3-yl]methoxy]imidazo[4,5-c]pyridin-4-yl]-2-methyl-but-3-yn-2-ol

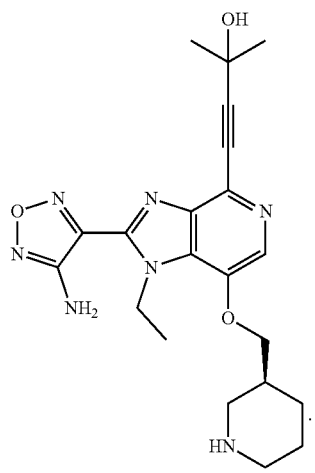 [SMILES: CCn1c(-c2nonc2N)nc2c(C#CC(C)(C)O)ncc(OC[C@H]3CCCNC3)c21]

GSK2110183

In an embodiment, the AKT inhibitor is GSK2110183. GSK2110183 has the chemical structure and name shown as: N-[(2S)-1-amino-3-(3,4-difluorophenyl)propan-2-yl]-5-chloro-4-(4-chloro-2-methylpyrazol-3-yl)thiophene-2-carboxamide

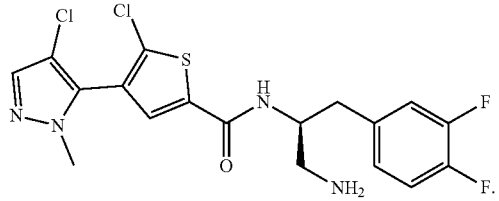 [SMILES: Cn1ncc(Cl)c1-c1cc(C(=O)N[C@H](CN)Cc2ccc(F)c(F)c2)sc1Cl]

GSK2141795 In an embodiment, the AKT inhibitor is GSK2141795. GSK2141795 has the chemical structure and name shown as: N-[(2S)-1-amino-3-(3,4-difluorophenyl)propan-2-yl]-5-chloro-4-(4-chloro-2-methylpyrazol-3-yl)furan-2-carboxamide

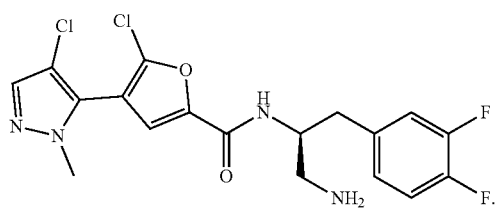

mTOR Inhibitor
Sirolimus

In an embodiment, the mTOR inhibitor is Sirolimus. Sirolimus has the chemical structure and name shown as: (3S,6R,7E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]oxaazacyclohentriacontine-1,5,11,28,29 (4H,6H,31H)-pentone

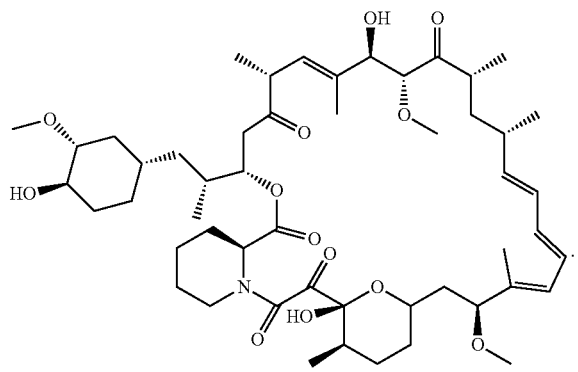 [SMILES: CO[C@H]1CC2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]
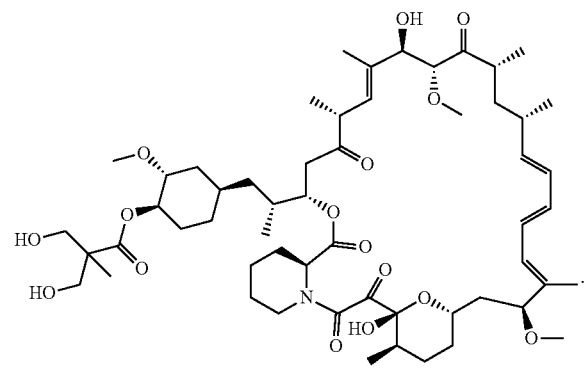

Everolimus

In an embodiment, the mTOR inhibitor is Everolimus. Everolimus has the chemical structure and name shown as: (1R,9S,12S,15R,16E,18R,19R,21R,23S,24E,26E,28E,30S,32S,35R)-1,18-dihydroxy-12-{(1R)-2-[(1S,3R,4R)-4-(2hydroxyethoxy)-3-methoxycyclohexyl]-1-methylethyl}-19,30-dimethoxy-15,17,21,23,29,35-hexamethyl-11,36-dioxa-4-aza-tricyclo[30.3.1.04,9]hexatriaconta16,24,26,28-tetraene-2,3,10,14,20-pentaone Zotarolimus In an embodiment, the mTOR inhibitor is Zotarolimus. Zotarolimus has the chemical structure and name shown as: (3S,6R,7E,9R,10R,12R,14S,15E,17E,19E,21S,23S,26R,27R,34aS)-9,27-dihydroxy-10,21-dimethoxy-3-{(1R)-2-[(1S,3R,4S)-3-methoxy-4-(1H-tetrazol-1-yl)cyclohexyl]-1-methylethyl}-6,8,12,14,20,26-hexamethyl-4,9,10,12,13,14,21,22,23,24,25,26,27,32,33,34,34a-heptadecahydro-3H-23,27-epoxypyrido[2,1-c][1,4]oxazacyclohentriacontine-1,5,11,28,29(6H,31H)-pentone

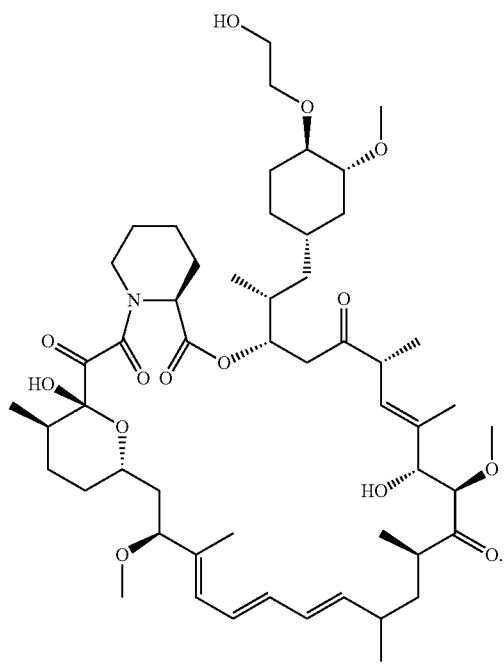 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)CC(C)/C=C/C=C/C=C/1C]

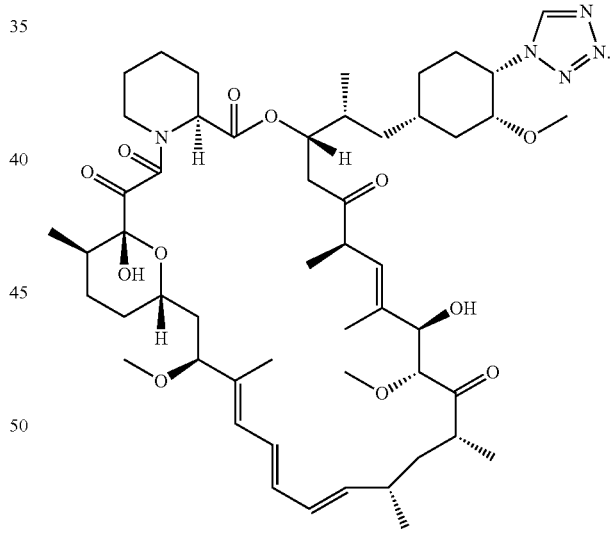

Temsirolimus

In an embodiment, the mTOR inhibitor is Temsirolimus. Temsirolimus has the chemical structure and name shown as: (1R,2R,4S)-4-{(2R)-2-[(3S,6R,7E,9R,10R,12R,14S,15E,17E,19E,21S,23S,26R,27R,34aS)-9,27-dihydroxy-10,21-dimethoxy-6,8,12,14,20,26-hexamethyl-1,5,11,28,29-pentaoxo-1,4,5,6,9,10,11,12,13,14,21,22,23,24,25,26,27,28,29,31,32,33,34,34a-tetracosahydro-3H-23,27-epoxypyrido[2,1-c][1,4]oxazacyclohentriacontin-3-yl]propyl}-2-methoxycyclohexyl 3-hydroxy-2-(hydroxymethyl)-2-methylpropanoate Deforolimus In an embodiment, the mTOR inhibitor is Deforolimus. Deforolimus has the chemical structure and name shown as: (1R,2R,4S)-4-[(2R)-2-[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.04,9]hexatriaconta-16,24,26,28-tetraen-12-yl]propyl]-2-methoxycyclohexyl dimethylphosphinate

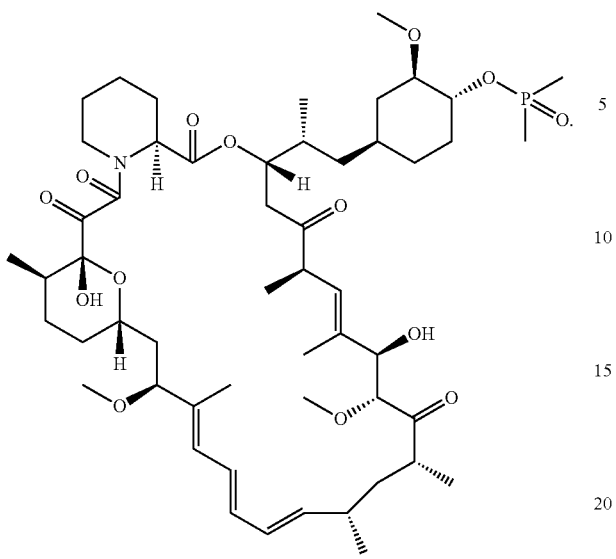

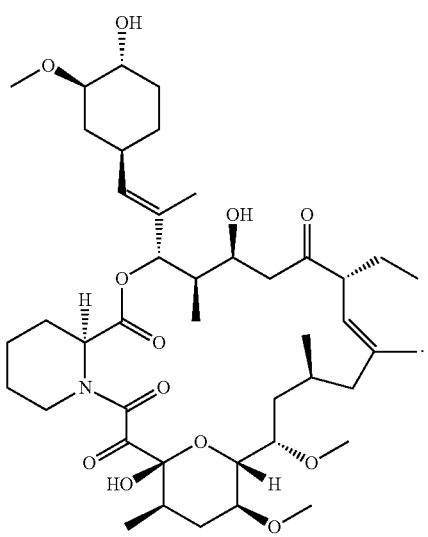

Tacrolimus

In an embodiment, the mTOR inhibitor is Tacrolimus. Tacrolimus has the chemical structure and name shown as: [3S [3R*[E(1S*,3S*,4S*)], 4S*,5R*,8S*,9E,12R*,14R*, 15S*,16R*,18S*,19S*,26aR*]]-5,6,8,11,12,13,14,15,16,17, 18,19,24,25,26,26a-hexadecahydro-5,19-dihydroxy-3-[2-(4-hydroxy-3-methoxycyclohexyl)-1-methylethenyl]-14, 16-dimethoxy-4,10,12,18-tetramethyl-8-(2-propenyl)-15, 19-epoxy-3H-pyrido[2,1-c][1,4] oxaazacyclotricosine-1,7, 20,21(4H,23H)-tetrone Wortmannin In an embodiment, the mTOR inhibitor is Wortmannin. Wortmannin has the chemical structure and name shown as: (1S,6bR,9aS,11R,11bR)-1-(methoxymethyl)-9a,11b-dimethyl-3,6,9-trioxo-3,6,6b,7,8,9,9a,10,11,11b-decahydro-1H-furo[4,3,2-de]indeno[4,5-h]isochromen-11-yl acetate

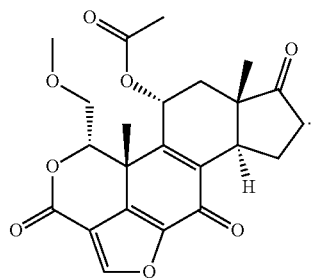 [SMILES: COC[C@H]1OC(=O)c2coc3c2[C@@]1(C)C1=C(C3=O)[C@@H]2CCC(=O)[C@@]2(C)C[C@H]1OC(C)=O]

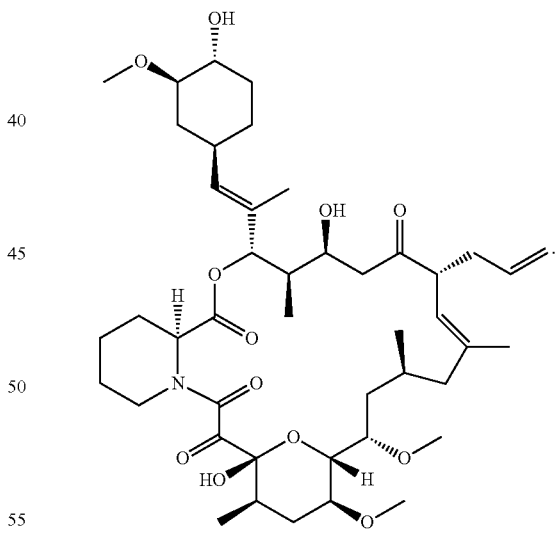

Ascomycin

In an embodiment, the mTOR inhibitor is Ascomycin. Ascomycin has the chemical structure and name shown as: (3S,4R,5S,8R,9E,12S,14S,15R,16S,18R,19R,26aS)-8-ethyl-5,6,8,11,12,13,14,15,16,17,18,19,24,25,26,26a-hexadecahydro-5,19-dihydroxy-3-[(1E)-2-[(1R,3R,4R)-4-hydroxy-3-methoxycyclohexyl]-1-methylethenyl]-14,16-dimethoxy-4,10,12,18-tetramethyl-15,19-epoxy-3H-pyrido[2,1-c][1,4]oxaazacyclotricosine-1,7,20,21(4H,23H)-tetrone

KU-0063794

In an embodiment, the mTOR inhibitor is KU-0063794. KU-0063794 has the chemical structure and name shown as: [5-[2-[(2R,6S)-2,6-dimethylmorpholin-4-yl]-4-morpholin-4-ylpyrido[2,3-d]pyrimidin-7-yl]-2-methoxyphenyl]methanol

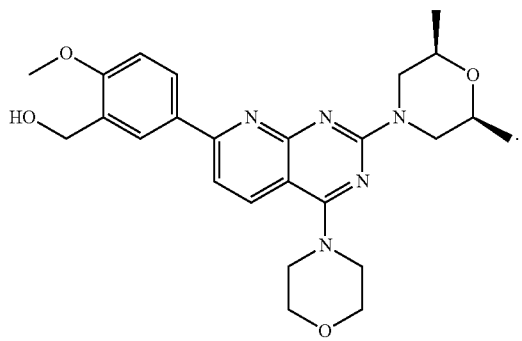 [SMILES: COc1ccc(-c2ccc3c(N4CCOCC4)nc(N4C[C@@H](C)O[C@@H](C)C4)nc3n2)cc1CO]

Sapanisertib

In an embodiment, the mTOR inhibitor is Sapanisertib. Sapanisertib has the chemical structure and name shown as: 5-(4-amino-1-propan-2-ylpyrazolo[3,4-d]pyrimidin-3-yl)-1,3-benzoxazol-2-amine

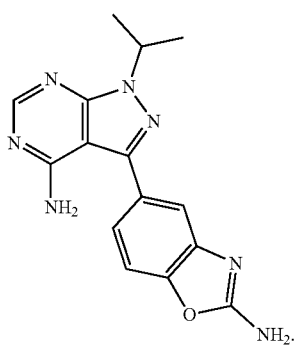 [SMILES: CC(C)n1nc(-c2ccc3oc(N)nc3c2)c2c(N)ncnc21]

AZD8055

In an embodiment, the mTOR inhibitor is AZD8055. AZD8055 has the chemical structure and name shown as: [5-[2,4-bis[(3S)-3-methylmorpholin-4-yl]pyrido[2,3-d]pyrimidin-7-yl]-2-methoxyphenyl]methanol

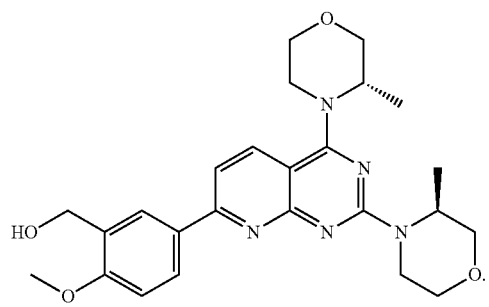 [SMILES: COc1ccc(-c2ccc3c(N4CCOC[C@@H]4C)nc(N4CCOC[C@@H]4C)nc3n2)cc1CO]

Vistusertib

In an embodiment, the mTOR inhibitor is Vistusertib. Vistusertib has the chemical structure and name shown as: 3-[2,4-bis[(3S)-3-methylmorpholin-4-yl]pyrido[2,3-d]pyrimidin-7-yl]-N-methylbenzamide

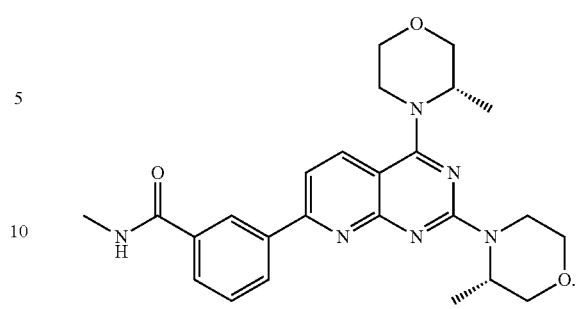

CC-223

In an embodiment, the mTOR inhibitor is CC-223. CC-223 has the chemical structure and name shown as: 3-[6-(2-hydroxypropan-2-yl)pyridin-3-yl]-5-(4-methoxycyclohexyl)-7,8-dihydropyrazino[2,3-b]pyrazin-6-one

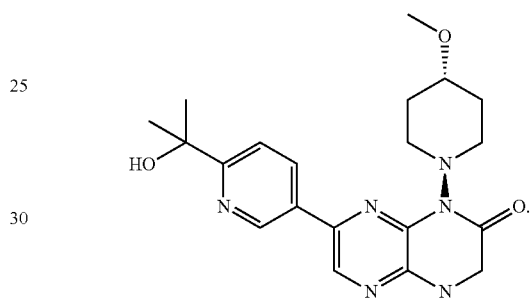

OSI-027

In an embodiment, the mTOR inhibitor is OSI-027. OSI-027 has the chemical structure and name shown as: 4-(4-amino-5-(7-methoxy-1H-indol-2-yl)imidazo[5,1-f][1,2,4]triazin-7-yl)cyclohexanecarboxylic acid

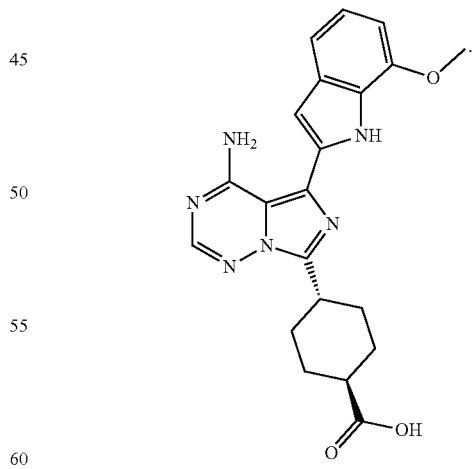

Voxtalisib

In an embodiment, the mTOR inhibitor is Voxtalisib. Voxtalisib has the chemical structure and name shown as: N-[4-[[3-(3,5-dimethoxyanilino)quinoxalin-2-yl]sulfamoyl]phenyl]-3-methoxy-4-methylbenzamide

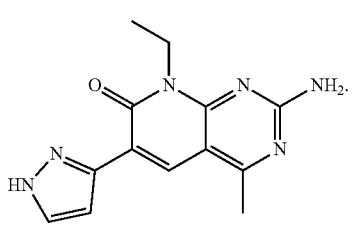 [SMILES: CCn1c(=O)c(-c2cc[nH]n2)cc2c(C)nc(N)nc21]

Palomid 529

In an embodiment, the mTOR inhibitor is Palomid 529. Palomid 529 has the chemical structure and name shown as: 8-(1-hydroxyethyl)-2-methoxy-3-[(4-methoxyphenyl)methoxy]benzo[c]chromen-6-one

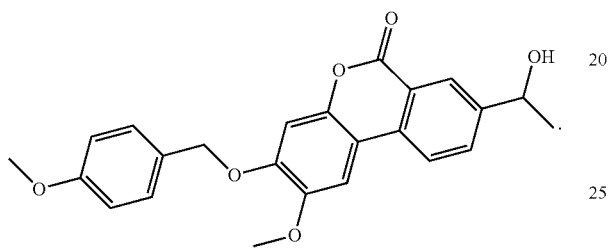

PP 242

In an embodiment, the mTOR inhibitor is PP 242. PP 242 has the chemical structure and name shown as: (2E)-2-(4-amino-1-propan-2-yl-2H-pyrazolo[3,4-d]pyrimidin-3-ylidene)indol-5-ol

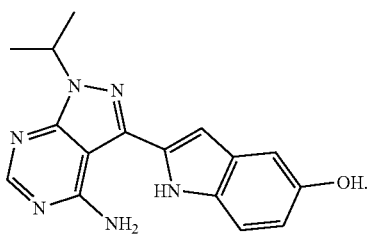 [SMILES: CC(C)n1nc(-c2cc3cc(O)ccc3[nH]2)c2c(N)ncnc21]

Dactolisib

In an embodiment, the mTOR inhibitor is Dactolisib. Dactolisib has the chemical structure and name shown as: 2-methyl-2-[4-(3-methyl-2-oxo-8-quinolin-3-ylimidazo[4,5-c]quinolin-1-yl)phenyl]propanenitrile

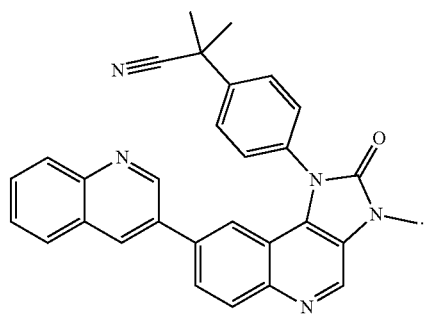 [SMILES: Cn1c(=O)n(-c2ccc(C(C)(C)C#N)cc2)c2c3cc(-c4cnc5ccccc5c4)ccc3ncc21]

BGT226

In an embodiment, the mTOR inhibitor is BGT226. BGT226 has the chemical structure and name shown as: (Z)-but-2-enedioic acid; 8-(6-methoxypyridin-3-yl)-3-methyl-1-[4-piperazin-1-yl-3-(trifluoromethyl)phenyl]imidazo[4,5-c]quinolin-2-one

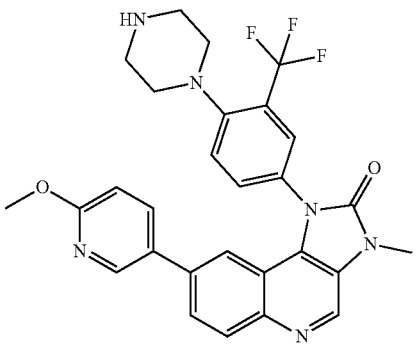

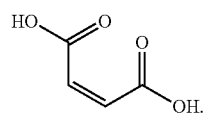

Apitolisib

In an embodiment, the mTOR inhibitor is Apitolisib. Apitolisib has the chemical structure and name shown as: (2S)-1-[4-[[2-(2-aminopyrimidin-5-yl)-7-methyl-4-morpholin-4-ylthieno[3,2-d]pyrimidin-6-yl]methyl]piperazin-1-yl]-2-hydroxypropan-1-one

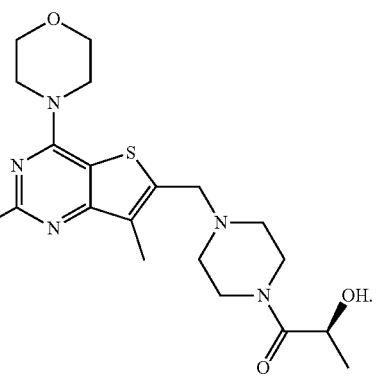

Omipalisib

In an embodiment, the mTOR inhibitor is Omipalisib. Omipalisib has the chemical structure and name shown as: 2,4-difluoro-N-[2-methoxy-5-(4-pyridazin-4-ylquinolin-6-yl)pyridin-3-yl]benzenesulfonamide

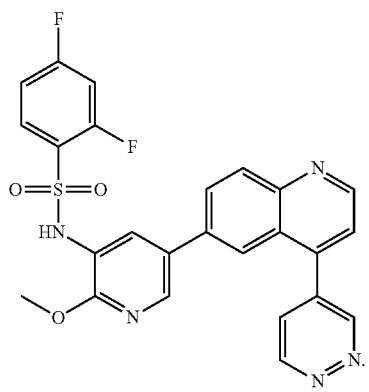 [SMILES: COc1ncc(-c2ccc3nccc(-c4ccnnc4)c3c2)cc1NS(=O)(=O)c1ccc(F)cc1F]

PF-04691502

In an embodiment, the mTOR inhibitor is PF-04691502. PF-04691502 has the chemical structure and name shown as: 2-amino-8-[4-(2-hydroxyethoxy)cyclohexyl]-6-(6-methoxypyridin-3-yl)-4-methylpyrido[2,3-d]pyrimidin-7-one

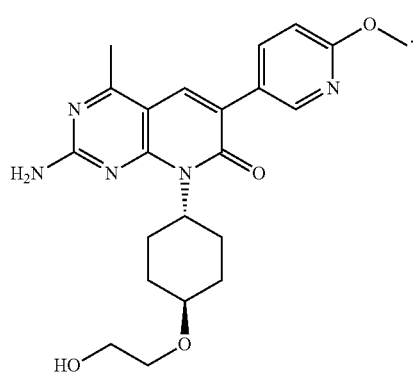 [SMILES: COc1ccc(-c2cc3c(C)nc(N)nc3n([C@H]3CC[C@H](OCCO)CC3)c2=O)cn1]

Gedatolisib

In an embodiment, the mTOR inhibitor is Gedatolisib. Gedatolisib has the chemical structure and name shown as: 1-[4-[4-(dimethylamino)piperidine-1-carbonyl]phenyl]-3-[4-(4,6-dimorpholin-4-yl-1,3,5-triazin-2-yl)phenyl]urea

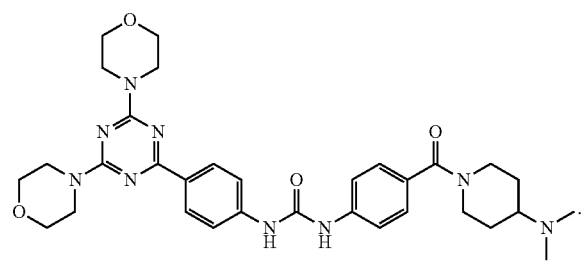 [SMILES: CN(C)C1CCN(C(=O)c2ccc(NC(=O)Nc3ccc(-c4nc(N5CCOCC5)nc(N5CCOCC5)n4)cc3)cc2)CC1]

Nucleoside Analogs

Decitabine

In an embodiment, the nucleoside analog is decitabine. decitabine has the chemical structure and name shown as: 4-amino-1-[(2R,4S,5R)-4-hydroxy-5-(hydroxymethyl)oxolan-2-yl]-1,3,5-triazin-2-one

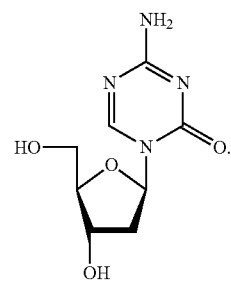 [SMILES: Nc1ncn([C@H]2C[C@@H](O)[C@@H](CO)O2)c(=O)n1]

Cytarabine

In an embodiment, the nucleoside analog is cytarabine. Cytarabine has the chemical structure and name shown as: 4-amino-1-[(2R,3S,4S,5R)-3,4-dihydroxy-5-(hydroxymethyl)oxolan-2-yl]pyrimidin-2-one

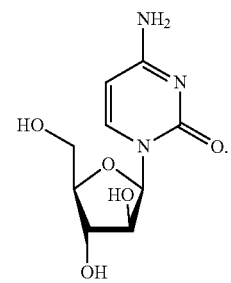

Azacitidine

In an embodiment, the nucleoside analog is azacitidine. Azacitidine has the chemical structure and name shown as: 4-amino-1-[(2R,3R,4S,5R)-3,4-dihydroxy-5-(hydroxymethyl)oxolan-2-yl]-1,3,5-triazin-2-one

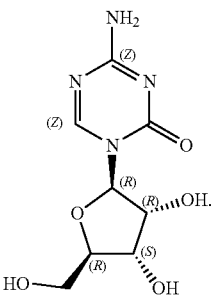

Zebularine

In an embodiment, the nucleoside analog is zebularine. Zebularine has the chemical structure and name shown as: 1-[(2R,3R,4S,5R)-3,4-dihydroxy-5-(hydroxymethyl)oxolan-2-yl]pyrimidin-2-one

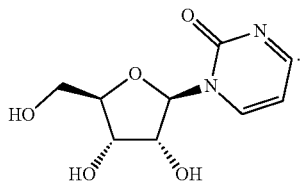 [SMILES: O=c1ncccn1[C@@H]1O[C@H](CO)[C@@H](O)[C@H]1O]

Pharmaceutical Compositions

In some embodiments, the invention provides pharmaceutical compositions comprising a combination comprising a MDM2 inhibitor and a therapeutic agent for treating a myeloproliferative neoplasm (MPN), wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. In an embodiment, the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD). In an embodiment, the myelofibrosis is selected from the group consisting of primary myelofibrosis (PMF), post-polycythemia vera myelofibrosis (post-PV MF), and post-essential thrombocythemia myelofibrosis (post-ET MF). In an embodiment, the primary myelofibrosis (PMF) is selected from the group consisting of prefibrotic/early stage PMF and overt fibrotic stage PMF. In an embodiment, the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T).

In an embodiment, the MDM2 inhibitor is a compound of Formula (I) or Formula (II) or a pharmaceutically acceptable salt thereof.

In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, R08994, Nutlin-3, Nutlin-3a, Nutlin-3b, Serdemetan, NSC59984, CHEMBL2386350, MK-8242, DS-3032, DS-3032B, R06839921, APG-115, MI-1601, and pharmaceutically acceptable salts thereof.

In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, R06839921, APG-115, MI-1601, and pharmaceutically acceptable salts thereof.

In an embodiment, the JAK inhibitor is selected from the group consisting of AC-410, AT9283, AZ960, AZD-1480, Baricitinib, BMS-911543, CEP-33779, Cerdulatinib, CHZ868, CYT387, Decernotinib, ENMD-2076, Filgotinib, Ganetespib, INCB039110, INCB-047986, Itacitinib, JAK3-IN-1, JANEX-1, LFM-A13, LY2784544, NS-018, NSC42834, NVP-BSK805, Oclacitinib, Pacritinib, Peficitinib, Pyridone 6, R348, RGB-286638, Ruxolitinib, Ruxolitinib-S, SAR-20347, SB1317, Solcitinib, TG101209, TG101348, Tofacitinib(3R,4S), Tofacitinib(3S,4R), Tofacitinib(3S,4S), Tofacitinib, TYK2-IN-2, Upadacitinib, WHI-P154, WHI-P97, WP1066, XL019, ZM39923, and pharmaceutically acceptable salts thereof.

In an embodiment, the JAK inhibitor is selected from the group consisting of Baricitinib phosphate, CYT387 Mesylate, CYT387 sulfate salt, NS-018 hydrochloride, NS-018 maleate, NVP-BSK805 dihydrochloride, Oclacitinib maleate, Ruxolitinib phosphate, Ruxolitinib sulfate, Tofacitinib citrate, and ZM39923 hydrochloride.

In an embodiment, the PD-1 inhibitor is selected from group consisting of nivolumab, pembrolizumab, pidilizumab, AMP-224, AMP-514, PDR001, and fragments, conjugates, or variants thereof.

In an embodiment, the PD-L1 inhibitor is an anti-PD-L1 antibody. In an embodiment, the PD-L1 inhibitor is selected from the group consisting of Atezolizumab, Avelumab, Durvalumab, BMS-936559, and fragments, conjugates, or variants thereof.

In an embodiment, the anti-PD-L2 antibody is rHIgM12B7A.

In an embodiment, the AKT inhibitor is selected from the group consisting of SB0203580, MK-2206, AZD5363, Miltefosine, Perifosine, PF-04691502, CCT128930, A-674563, RX-0201, PBI-05204, AKT inhibitor VIII, AT7867, AT13148, GDC-0068, TIC10, SC79, GSK690693, GSK2110183, GSK2141795, and pharmaceutically acceptable salts thereof.

In an embodiment, the mTOR inhibitor is selected from the group consisting of Sirolimus, Everolimus, Temsirolimus, Zotarolimus, Deforolimus, Wortmannin, Ascomycin, Tacrolimus, KU-0063794, Sapanisertib, AZD8055, Vistusertib, CC-223, OSI-027, Voxtalisib, Palomid 529, PP 242, Dactolisib, BGT226, Apitolisib, Omipalisib, PF-04691502, Gedatolisib, and pharmaceutically acceptable salts thereof.

In an embodiment, the PI3K inhibitor is selected from the group consisting of Buparlisib, Alpelisib, Pictilisib, Pilaralisib, Sonolisib, Copanlisib, CH5132799, Serabelisib, AZD8186, SAR260301, GSK2636771, Idelalisib, Acalisib, Duvelisib, Taselisib, AMG319, GDC-0084, and pharmaceutically acceptable salts thereof.

In an embodiment, the IDH inhibitor is selected from the group consisting of Enasidenib, Ivosidenib, AGI-5198, AGI-6780, CHEMBL3682093, Vorasidenib, IDH-305, BAY-1436032, GSK864, (R,S)-Ivosidenib, IDH1-IN-2, IDH1-IN-1, Enasidenib mesylate, and pharmaceutically acceptable salts thereof.

In an embodiment, the interferon is selected from the group consisting of interferon alpha (IFN-α), interferon beta (IFN-β), interferon lambda (IFN-λ), interferon gamma (IFN-γ), and combinations thereof.

In an embodiment, the interferon is selected from the group consisting of interferon-alpha-2a, interferon-alpha-2b, interferon-alpha-2c, interferon-alpha-n1, interferon-alpha-n3, PEGylated interferon-alpha-2a, PEGylated interferon-alpha-2b, PEGylated interferon-alpha-2c, PEGylated interferon-alpha-n1, PEGylated interferon-alpha-n3, and combinations thereof.

In an embodiment, thrombocythemia is essential thrombocythemia (ET).

In an embodiment, myelofibrosis is selected from primary myelofibrosis (PMF), post-polycythemia vera myelofibrosis (post-PV MF), and post-essential thrombocythemia myelofibrosis (post-ET MF).

Polycythemia Vera

In some embodiments, the invention provides pharmaceutical compositions comprising a combination of the compound of Formula (I) or Formula (II) or a pharmaceutically acceptable salt thereof and a therapeutic agent for treating polycythemia vera, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, a mTOR inhibitor, and combinations thereof; wherein the JAK inhibitor is selected from the group consisting of AC-410, AT9283, AZ960, AZD-1480, Baricitinib, BMS-911543, CEP-33779, Cerdulatinib, CHZ868, CYT387, Decernotinib, ENMD-2076, Filgotinib, Ganetespib, INCB039110, INCB-047986, Itacitinib, JAK3-IN-1, JANEX-1, LFM-A13, LY2784544, NS-018, NSC42834, NVP-BSK805, Oclacitinib, Pacritinib, Peficitinib, Pyridone 6, R348, RGB-286638, Ruxolitinib, Ruxolitinib-S, SAR-20347, SB1317, Solcitinib, TG101209, TG101348, Tofacitinib(3R,4S), Tofacitinib(3S,4R), Tofacitinib(3S,4S), Tofacitinib, TYK2-IN-2, Upadacitinib, WHI-P154, WHI-P97, WP1066, XL019, ZM39923, and pharmaceutically acceptable salts thereof; wherein, the PD-1 inhibitor is selected from group consisting of nivolumab, pembrolizumab, pidilizumab, AMP-224, AMP-514, PDR001, and fragments, conjugates, or variants thereof; wherein the PD-L1 inhibitor is selected from the group consisting of Atezolizumab, Avelumab, Durvalumab, BMS-936559, and fragments, conjugates, or variants thereof; wherein the anti-PD-L2 inhibitor is rHIgM12B7A; wherein the AKT inhibitor is selected from the group consisting of SB0203580, MK-2206, AZD5363, Miltefosine, Perifosine, PF-04691502, CCT128930, A-674563, RX-0201, PBI-05204, AKT inhibitor VIII, AT7867, AT13148, GDC-0068, TIC10, SC79, GSK690693, GSK2110183, GSK2141795, and pharmaceutically acceptable salts thereof; wherein the mTOR inhibitor is selected from the group consisting of Sirolimus, Everolimus, Temsirolimus, Zotarolimus, Deforolimus, Wortmannin, Ascomycin, Tacrolimus, KU-0063794, Sapanisertib, AZD8055, Vistusertib, CC-223, OSI-027, Voxtalisib, Palomid 529, PP 242, Dactolisib, BGT226, Apitolisib, Omipalisib, PF-04691502, Gedatolisib, and pharmaceutically acceptable salts thereof; wherein the PI3K inhibitor is selected from the group consisting of Buparlisib, Alpelisib, Pictilisib, Pilaralisib, Sonolisib, Copanlisib, CH5132799, Serabelisib, AZD8186, SAR260301, GSK2636771, Idelalisib, Acalisib, Duvelisib, Taselisib, AMG319, GDC-0084, and pharmaceutically acceptable salts thereof; wherein the IDH inhibitor is selected from the group consisting of Enasidenib, Ivosidenib, AGI-5198, AGI-6780, CHEMBL3682093, Vorasidenib, IDH-305, BAY-1436032, GSK864, (R,S)-Ivosidenib, IDH1-IN-2, IDH1-IN-1, Enasidenib mesylate, and pharmaceutically acceptable salts thereof; wherein the interferon is selected from the group consisting of interferon-alpha-2a, interferon-alpha-2b, interferon-alpha-2c, interferon-alpha-n1, interferon-alpha-n3, PEGylated interferon-alpha-2a, PEGylated interferon-alpha-2b, PEGylated interferon-alpha-2c, PEGylated interferon-alpha-n1, PEGylated interferon-alpha-n3, and combinations thereof.

Essential Thrombocythemia (ET)

In some embodiments, the invention provides pharmaceutical compositions comprising a combination of the compound of Formula (I) or Formula (II) or a pharmaceutically acceptable salt thereof and a therapeutic agent for treating essential thrombocythemia, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, a mTOR inhibitor, and combinations thereof; wherein the JAK inhibitor is selected from the group consisting of AC-410, AT9283, AZ960, AZD-1480, Baricitinib, BMS-911543, CEP-33779, Cerdulatinib, CHZ868, CYT387, Decernotinib, ENMD-2076, Filgotinib, Ganetespib, INCB039110, INCB-047986, Itacitinib, JAK3-IN-1, JANEX-1, LFM-A13, LY2784544, NS-018, NSC42834, NVP-BSK805, Oclacitinib, Pacritinib, Peficitinib, Pyridone 6, R348, RGB-286638, Ruxolitinib, Ruxolitinib-S, SAR-20347, SB1317, Solcitinib, TG101209, TG101348, Tofacitinib(3R,4S), Tofacitinib(3S,4R), Tofacitinib(3S,4S), Tofacitinib, TYK2-IN-2, Upadacitinib, WHI-P154, WHI-P97, WP1066, XL019, ZM39923, and pharmaceutically acceptable salts thereof; wherein, the PD-1 inhibitor is selected from group consisting of nivolumab, pembrolizumab, pidilizumab, AMP-224, AMP-514, PDR001, and fragments, conjugates, or variants thereof; wherein the PD-L1 inhibitor is selected from the group consisting of Atezolizumab, Avelumab, Durvalumab, BMS-936559, and fragments, conjugates, or variants thereof; wherein the anti-PD-L2 inhibitor is rHIgM12B7A; wherein the AKT inhibitor is selected from the group consisting of SB0203580, MK-2206, AZD5363, Miltefosine, Perifosine, PF-04691502, CCT128930, A-674563, RX-0201, PBI-05204, AKT inhibitor VIII, AT7867, AT13148, GDC-0068, TIC10, SC79, GSK690693, GSK2110183, GSK2141795, and pharmaceutically acceptable salts thereof; wherein the mTOR inhibitor is selected from the group consisting of Sirolimus, Everolimus, Temsirolimus, Zotarolimus, Deforolimus, Wortmannin, Ascomycin, Tacrolimus, KU-0063794, Sapanisertib, AZD8055, Vistusertib, CC-223, OSI-027, Voxtalisib, Palomid 529, PP 242, Dactolisib, BGT226, Apitolisib, Omipalisib, PF-04691502, Gedatolisib, and pharmaceutically acceptable salts thereof; wherein the PI3K inhibitor is selected from the group consisting of Buparlisib, Alpelisib, Pictilisib, Pilaralisib, Sonolisib, Copanlisib, CH5132799, Serabelisib, AZD8186, SAR260301, GSK2636771, Idelalisib, Acalisib, Duvelisib, Taselisib, AMG319, GDC-0084, and pharmaceutically acceptable salts thereof; wherein the IDH inhibitor is selected from the group consisting of Enasidenib, Ivosidenib, AGI-5198, AGI-6780, CHEMBL3682093, Vorasidenib, IDH-305, BAY-1436032, GSK864, (R,S)-Ivosidenib, IDH1-IN-2, IDH1-IN-1, Enasidenib mesylate, and pharmaceutically acceptable salts thereof; wherein the interferon is selected from the group consisting of interferon-alpha-2a, interferon-alpha-2b, interferon-alpha-2c, interferon-alpha-n1, interferon-alpha-n3, PEGylated interferon-alpha-2a, PEGylated interferon-alpha-2b, PEGylated interferon-alpha-2c, PEGylated interferon-alpha-n1, PEGylated interferon-alpha-n3, and combinations thereof.

Myelofibrosis

In some embodiments, the invention provides pharmaceutical compositions comprising a combination of the compound of Formula (I) or Formula (II) or a pharmaceutically acceptable salt thereof and a therapeutic agent for treating myelofibrosis, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, a mTOR inhibitor, and combinations thereof; wherein the JAK inhibitor is selected from the group consisting of AC-410, AT9283, AZ960, AZD-1480, Baricitinib, BMS-911543, CEP-33779, Cerdulatinib, CHZ868, CYT387, Decernotinib, ENMD-2076, Filgotinib, Ganetespib, INCB039110, INCB-047986, Itacitinib, JAK3-IN-1, JANEX-1, LFM-A13, LY2784544, NS-018, NSC42834, NVP-BSK805, Oclacitinib, Pacritinib, Peficitinib, Pyridone 6, R348, RGB-286638, Ruxolitinib, Ruxolitinib-S, SAR-20347, SB1317, Solcitinib, TG101209, TG101348, Tofacitinib(3R,4S), Tofacitinib(3S,4R), Tofacitinib(3S,4S), Tofacitinib, TYK2-IN-2, Upadacitinib, WHI-P154, WHI-P97, WP1066, XL019, ZM39923, and pharmaceutically acceptable salts thereof; wherein, the PD-1 inhibitor is selected from group consisting of nivolumab, pembrolizumab, pidilizumab, AMP-224, AMP-514, PDR001, and fragments, conjugates, or variants thereof; wherein the PD-L1 inhibitor is selected from the group consisting of Atezolizumab, Avelumab, Durvalumab, BMS-936559, and fragments, conjugates, or variants thereof; wherein the anti-PD-L2 inhibitor is rHIgM12B7A; wherein the AKT inhibitor is selected from the group consisting of SB0203580, MK-2206, AZD5363, Miltefosine, Perifosine, PF-04691502, CCT128930, A-674563, RX-0201, PBI-05204, AKT inhibitor VIII, AT7867, AT13148, GDC-0068, TIC10, SC79, GSK690693, GSK2110183, GSK2141795, and pharmaceutically acceptable salts thereof; wherein the mTOR inhibitor is selected from the group consisting of Sirolimus, Everolimus, Temsirolimus, Zotarolimus, Deforolimus, Wortmannin, Ascomycin, Tacrolimus, KU-0063794, Sapanisertib, AZD8055, Vistusertib, CC-223, OSI-027, Voxtalisib, Palomid 529, PP 242, Dactolisib, BGT226, Apitolisib, Omipalisib, PF-04691502, Gedatolisib, and pharmaceutically acceptable salts thereof; wherein the PI3K inhibitor is selected from the group consisting of Buparlisib, Alpelisib, Pictilisib, Pilaralisib, Sonolisib, Copanlisib, CH5132799, Serabelisib, AZD8186, SAR260301, GSK2636771, Idelalisib, Acalisib, Duvelisib, Taselisib, AMG319, GDC-0084, and pharmaceutically acceptable salts thereof; wherein the IDH inhibitor is selected from the group consisting of Enasidenib, Ivosidenib, AGI-5198, AGI-6780, CHEMBL3682093, Vorasidenib, IDH-305, BAY-1436032, GSK864, (R,S)-Ivosidenib, IDH1-IN-2, IDH1-IN-1, Enasidenib mesylate, and pharmaceutically acceptable salts thereof; wherein the interferon is selected from the group consisting of interferon-alpha-2a, interferon-alpha-2b, interferon-alpha-2c, interferon-alpha-n1, interferon-alpha-n3, PEGylated interferon-alpha-2a, PEGylated interferon-alpha-2b, PEGylated interferon-alpha-2c, PEGylated interferon-alpha-n1, PEGylated interferon-alpha-n3, and combinations thereof.

In an embodiment, myelofibrosis is selected from primary myelofibrosis (PMF), post-polycythemia vera myelofibrosis (post-PV MF), and post-essential thrombocythemia myelofibrosis (post-ET ME).

The pharmaceutical compositions are typically formulated to provide a therapeutically effective amount of a MDM2 inhibitor and a therapeutically effective amount of a therapeutic agent, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. Where desired, the pharmaceutical compositions contain a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

In selected embodiments, the concentration of a MDM2 inhibitor and a therapeutic agent provided in the pharmaceutical compositions of the invention is independently less than, for example, 100%, 90%, 80%, 70%, 60%, 50%, 40%, 30%, 20%, 19%, 18%, 17%, 16%, $15^{5\%}$, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In selected embodiments, the concentration of a MDM2 inhibitor and a therapeutic agent provided in the pharmaceutical compositions of the invention is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In selected embodiments, the concentration of a MDM2 inhibitor and a therapeutic agent is independently in the range from approximately 0.0001% to approximately 50%, approximately 0.0010% to approximately 40%, approximately 0.010% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.10% to approximately 210%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12% or approximately 1% to approximately 10% w/w, w/v or v/v, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In selected embodiments, the concentration of a MDM2 inhibitor and a therapeutic agent is independently in the range from approximately 0.0010% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In selected embodiments, the amount of a MDM2 inhibitor and a therapeutic agent is independently equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g or 0.0001 g, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In selected embodiments, the amount of a MDM2 inhibitor and a therapeutic agent is independently more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g or 10 g, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

A MDM2 inhibitor is effective over a wide dosage range. For example, in the treatment of adult humans, dosages independently ranging from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

Pharmaceutical Compositions for Oral Administration

In selected embodiments, the invention provides a pharmaceutical composition for oral administration a combination comprising a MDM2 inhibitor and a therapeutic agent, and a pharmaceutical excipient suitable for oral administration, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In selected embodiments, the invention provides a solid pharmaceutical composition for oral administration containing: (i) a combination comprising an effective amount of a MDM2 inhibitor and a therapeutic agent, in combination with (ii) a pharmaceutical excipient suitable for oral administration, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. In selected embodiments, the composition further contains (iii) an effective amount of at least one additional active ingredient.

In selected embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

A combination of a MDM2 inhibitor with a therapeutic agent can be further combined in an intimate admixture with a pharmaceutical carrier according to conventional pharmaceutical compounding techniques, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and combinations thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and combinations thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or combinations thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or combinations thereof. Additional lubricants include, for example, a syloid silica gel, a coagulated aerosol of synthetic silica, or combinations thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and combinations thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and combinations thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and combinations thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and combinations thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and combinations thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and combinations thereof. Within this group, preferred lipophilic surfactants include glycerol fatty acid esters, propylene glycol fatty acid esters, and combinations thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use, such as for compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, epsilon-caprolactone and isomers thereof, S-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and combinations thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Examples may include, but are not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In selected embodiments, the invention provides a pharmaceutical composition for injection comprising a combination comprising a MDM2 inhibitor and a therapeutic agent, and a pharmaceutical excipient suitable for injection, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable combinations thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid and thimerosal.

Sterile injectable solutions are prepared by incorporating a MDM2 inhibitor and a therapeutic agent in the required amounts in the appropriate solvent with various other ingredients as enumerated above, as required, followed by filtered sterilization, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Administration of a combination comprising a MDM2 inhibitor and a therapeutic agent can be effected by any method that enables delivery of the compounds to the site of action, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. These methods include oral routes, intraduodenal routes, parenteral injection (including intravenous, intra-arterial, subcutaneous, intramuscular, intravascular, or infusion), topical (e.g., transdermal application), via local delivery by catheter or stent.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include a MDM2 inhibitor and a therapeutic agent, either alone or in combination in suitable packaging, and written material that can include instructions for use, discussion of clinical studies and listing of side effects, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer. In an embodiment, the invention provides a kit comprising a combination comprising a MDM2 inhibitor and a therapeutic agent for use in the treatment of a MPN, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. In an embodiment, the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD). In an embodiment, the myelofibrosis is selected from the group consisting of primary myelofibrosis (PMF), post-polycythemia vera myelofibrosis (post-PV MF), and post-essential thrombocythemia myelofibrosis (post-ET MF). In an embodiment, the primary myelofibrosis (PMF) is selected from the group consisting of prefibrotic/early stage PMF and overt fibrotic stage PMF. In an embodiment, the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T).

Dosages and Dosing Regimens

The amount of a MDM2 inhibitor and a therapeutic agent administered will be independently dependent on the human being treated, the severity of the disorder or condition, the rate of administration, the disposition of the compounds and the discretion of the prescribing physician, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day.

In some embodiments, a MDM2 inhibitor and a therapeutic agent are independently administered in a single dose, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. Typically, such administration will be by injection—e.g., intravenous injection, in order to introduce the agents quickly. However, other routes may be used as appropriate. A single dose of a MDM2 inhibitor and a therapeutic agent may also be used for treatment of an acute condition, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In some embodiments, a MDM2 inhibitor and a therapeutic agent are independently administered in multiple doses for treating a MPN, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. In an embodiment, a MDM2 inhibitor and a JAK inhibitor are independently administered in multiple doses by injection—e.g., intravenous injection. In an embodiment, dosing may be once, twice, three times, four times, five times, six times, or more than six times per day. In an embodiment, dosing may be selected from the group consisting of once a day, twice a day, three times a day, four times a day, five times a day, six times a day, once every other day, once weekly, twice weekly, three times weekly, four times weekly, biweekly, and monthly. In some embodiments a MDM2 inhibitor and a therapeutic agent are independently administered three times a week, including every Monday, Wednesday, and Friday, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

Administration of a MDM2 inhibitor and a therapeutic agent may independently continue as long as necessary, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. In some embodiments, the MDM2 inhibitor and the therapeutic agent are independently administered for more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days. In some embodiments, the MDM2 inhibitor and the therapeutic agent are independently administered for less than 28, 14, 7, 6, 5, 4, 3, 2, or 1 day. In some embodiments, the MDM2 inhibitor and the therapeutic agent are independently administered for about 14 days, about 21 days, about 28 days, about 35 days, about 42 days, about 49 days, or about 56 days. In some embodiments, the MDM2 inhibitor and the therapeutic agent are independently administered chronically on an ongoing basis—e.g., for the treatment of chronic effects. In another embodiment, the administration of the MDM2 inhibitor and the therapeutic agent independently continues for less than about 7 days. In yet another embodiment the administration continues for more than about 6, 10, 14, 28 days, two months, three months, four months, five months, six months, seven months, eight months, nine months, ten months, eleven months or one year. In some embodiments, the administration continues for more than about one year, two years, three years, four years, or five years. In some embodiments, continuous dosing is achieved and maintained as long as necessary.

In some embodiments, an effective dosage of the MDM2 inhibitor and the therapeutic agent is independently in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof. In some embodiments, an effective dosage of the MDM2 inhibitor and the therapeutic agent is about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In some embodiments, an effective dosage of a MDM2 inhibitor or a JAK inhibitor is 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In some embodiments, an effective dosage of the MDM2 inhibitor or the therapeutic agent is independently in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of a MDM2 inhibitor or a JAK inhibitor is about 0.35 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg, wherein the therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

In some embodiments, a MDM2 inhibitor or a pharmaceutically acceptable salt thereof is administered at a dosage of 10 to 500 mg BID, including a dosage of 15 mg, 25 mg, 30 mg, 50 mg, 60 mg, 75 mg, 100 mg, 120 mg, 150 mg, 175 mg, 200 mg, 225 mg, 240 mg, 250 mg, 275 mg, 300 mg, 325 mg, 350 mg, 360 mg, 375 mg, and 480 mg BID.

In some embodiments, a MDM2 inhibitor or a pharmaceutically acceptable salt thereof is administered at a dosage of 10 to 500 mg QD, including a dosage of 15 mg, 25 mg, 30 mg, 50 mg, 60 mg, 75 mg, 100 mg, 120 mg, 150 mg, 175 mg, 200 mg, 225 mg, 240 mg, 250 mg, 275 mg, 300 mg, 325 mg, 350 mg, 360 mg, 375 mg, and 480 mg QD.

In some embodiments, the interferon is administered in a dose selected from the group consisting of about 1 million international units (MU) to about 800 MU, from about 1 MU to about 10 MU, from about 20 MU to about 40 MU, from about 2 MU to about 15 MU, from about 5 MU to about 25 MU, from about 50 MU to about 100 MU, from about 150 MU to about 250 MU, from about 300 MU to about 400 MU, and from about 500 MU to about 600 MU.

In some embodiments, the interferon is administered in a dose selected from the group consisting of from about 0.1 µg/day to about 1 mg/day, from about 10 µg/day to about 200 µg/day, from about 20 µg/day to about 150 µg/day, from about 0.1 µg/day to about 125 µg/day, from about 1 µg/day to about 20 µg/day, and about 4.5 µg/day to about 30 µg/day.

In some embodiments, the interferon is administered in a dose selected from the group consisting of 1, 2, 3, 4, 5, 6, 7, 8, 9, 10, 11, 12, 13, 14, 15, 16, 17, 18 19, 20, 21, 22, 23, 24, 25, 26, 27, 28, 29, and 30 MU/m$^2$.

An effective amount of the MDM2 inhibitor or the therapeutic agent may be administered in either single or multiple doses by any of the accepted modes of administration of agents having similar utilities, including buccal, sublingual, and transdermal routes, by intra-arterial injection, intravenously, parenterally, intramuscularly, subcutaneously or orally.

In some embodiments, the MDM2 inhibitor and the therapeutic agent are independently administered to a subject intermittently, known as intermittent administration. By "intermittent administration", it is meant a period of administration of a therapeutically effective dose of a MDM2 inhibitor and/or the therapeutic agent, followed by a time period of discontinuance, which is then followed by another administration period and so on. In each administration period, the dosing frequency can be independently select from three times daily, twice daily, daily, once weekly, twice weekly, three times weekly, four times weekly, five times weekly, six times weekly or monthly. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, R08994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, R06839921, APG-115, MI-1601, and pharmaceutically acceptable salts thereof. In an embodiment, the JAK inhibitor is selected from the group consisting of AC-410, AT9283, AZ960, AZD-1480, Baricitinib, BMS-911543, CEP-33779, Cerdulatinib, CHZ868, CYT387, Decernotinib, ENMD-2076, Filgotinib, Ganetespib, INCB039110, INCB-047986, Itacitinib, JAK3-IN-1, JANEX-1, LFM-A13, LY2784544, NS-018, NSC42834, NVP-BSK805, Oclacitinib, Pacritinib, Peficitinib, Pyridone 6, R348, RGB-286638, Ruxolitinib, Ruxolitinib-S, SAR- 20347, SB1317, Solcitinib, TG101209, TG101348, Tofacitinib(3R,4S), Tofacitinib(3S,4R), Tofacitinib(3S,4S), Tofacitinib, TYK2-IN-2, Upadacitinib, WHI-P154, WHI-P97, WP1066, XL019, ZM39923, and pharmaceutically acceptable salts thereof. In an embodiment, the JAK inhibitor is selected from the group consisting of Baricitinib phosphate, CYT387 Mesylate, CYT387 sulfate salt, NS-018 hydrochloride, NS-018 maleate, NVP-BSK805 dihydrochloride, Oclacitinib maleate, Ruxolitinib phosphate, Ruxolitinib sulfate, Tofacitinib citrate, and ZM39923 hydrochloride. In an embodiment, the PD-1 inhibitor is selected from group consisting of nivolumab, pembrolizumab, pidilizumab, AMP-224, AMP-514, PDR001, and fragments, conjugates, or variants thereof. In an embodiment, the PD-L1 inhibitor is an anti-PD-L1 antibody. In an embodiment, the PD-L1 inhibitor is selected from the group consisting of Atezolizumab, Avelumab, Durvalumab, BMS-936559, and fragments, conjugates, or variants thereof. In an embodiment, the anti-PD-L2 antibody is rHIgM12B7A. In an embodiment, the AKT inhibitor is selected from the group consisting of SB0203580, MK-2206, AZD5363, Miltefosine, Perifosine, PF-04691502, CCT128930, A-674563, RX-0201, PBI-05204, AKT inhibitor VIII, AT7867, AT13148, GDC-0068, TIC10, SC79, GSK690693, GSK2110183, GSK2141795, and pharmaceutically acceptable salts thereof. In an embodiment, the mTOR inhibitor is selected from the group consisting of Sirolimus, Everolimus, Temsirolimus, Zotarolimus, Deforolimus, Wortmannin, Ascomycin, Tacrolimus, KU-0063794, Sapanisertib, AZD8055, Vistusertib, CC-223, OSI-027, Voxtalisib, Palomid 529, PP 242, Dactolisib, BGT226, Apitolisib, Omipalisib, PF-04691502, Gedatolisib, and pharmaceutically acceptable salts thereof. In an embodiment, the PI3K inhibitor is selected from the group consisting of Buparlisib, Alpelisib, Pictilisib, Pilaralisib, Sonolisib, Copanlisib, CH5132799, Serabelisib, AZD8186, SAR260301, GSK2636771, Idelalisib, Acalisib, Duvelisib, Taselisib, AMG319, GDC-0084, and pharmaceutically acceptable salts thereof. In an embodiment, the IDH inhibitor is selected from the group consisting of Enasidenib, Ivosidenib, AGI-5198, AGI-6780, CHEMBL3682093, Vorasidenib, IDH-305, BAY-1436032, GSK864, (R,S)-Ivosidenib, IDH1-IN-2, IDH1-IN-1, Enasidenib mesylate, and pharmaceutically acceptable salts thereof. In an embodiment, the interferon is selected from the group consisting of interferon alpha (IFN-α), interferon beta (IFN-β), interferon lambda (IFN-λ), interferon gamma (IFN-γ), and combinations thereof. In an embodiment, the interferon is selected from the group consisting of interferon-alpha-2a, interferon-alpha-2b, interferon-alpha-2c, interferon-alpha-n1, interferon-alpha-n3, PEGylated interferon-alpha-2a, PEGylated interferon-alpha-2b, PEGylated interferon-alpha-2c, PEGylated interferon-alpha-n1, PEGylated interferon-alpha-n3, and combinations thereof.

By "period of discontinuance" or "discontinuance period" or "rest period", it is meant to the length of time when discontinuing of the administration of the MDM2 inhibitor and/or the therapeutic agent. The time period of discontinuance may be longer or shorter than the administration period or the same as the administration period. For example, where the administration period comprises three times daily, twice daily, daily, once weekly, twice weekly, three times weekly, four times weekly, five times weekly, six times weekly or monthly dosing, the discontinuance period may be at least about 2, 3, 4, 5, 6, 7, 8, 9, 10, 11, 12, 13, 14, 15, 16, 17, 18, 19, 20, 21, 22, 23, 24, 25, 26, 27, 28, 29, one month, two months, three months, four months or more days. During the discontinuance period, other therapeutic agents other than a MDM2 inhibitor and the therapeutic agent may be administered.

In an embodiment, the MDM2 inhibitor and the therapeutic agent are independently administered to a human subject in need thereof for treating a myeloproliferative neoplasm (MPN) for a first administration period, then followed by a discontinuance period, then followed by a second administration period, and so on. In an embodiment, the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD). In an embodiment, the myelofibrosis is selected from the group consisting of primary myelofibrosis (PMF), post-polycythemia vera myelofibrosis (post-PV MF), and post-essential thrombocythemia myelofibrosis (post-ET MF). In an embodiment, the primary myelofibrosis (PMF) is selected from the group consisting of prefibrotic/early stage PMF and overt fibrotic stage PMF. In an embodiment, the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T). The first administration period, the second administration period, and the discontinuance period are independently selected from the group consisting of more than 1, 2, 3, 4,5,6,7,8,9, 10, 11, 12, 13, 14, 15, 16, 17, 18, 19, 20, 21, 22, 23, 24, 25, 26, 27, 28, 29, one month, two months, three months, four months and more days, in which the MDM2 inhibitor and the therapeutic agent are independently administered to a subject three times daily, twice daily, daily, once weekly, twice weekly, three times weekly, four times weekly, five times weekly, six times weekly or monthly. In an embodiment, the first administration period is at same length as the second administration period. In an embodiment, the first administration period is shorter than the second administration period. In an embodiment, the first administration period is longer than the second administration period. In an embodiment, the first administration period and the second administration period are about three weeks, in which the MDM2 inhibitor and the therapeutic agent are independently administered to a subject daily; and the discontinuance is about two weeks. In an embodiment, the first administration period and the second administration period are about three weeks, in which the MDM2 inhibitor and the therapeutic agent are independently administered to a subject weekly; and the discontinuance is about two weeks. In an embodiment, the first administration period and the second administration period are about four weeks, in which the MDM2 inhibitor and the therapeutic agent are independently administered to a subject daily; and the discontinuance is about two weeks. In an embodiment, the first administration period and the second administration period are about four weeks, in which the MDM2 inhibitor and the therapeutic agent are independently administered to a subject weekly; and the discontinuance is about two weeks. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, R08994, Nutlin-3, Nutlin-3a, Nutlin-3b, Serdemetan, NSC59984, CHEMBL2386350, MK-8242, DS-3032, DS-3032B, R06839921, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, R06839921, APG-115, MI-1601, and pharmaceutically acceptable salts thereof. In an embodiment, the JAK inhibitor is selected from the group consisting of AC-410, AT9283, AZ960, AZD-1480, Baricitinib, BMS-911543, CEP-33779, Cerdulatinib, CHZ868, CYT387, Decernotinib, ENMD-2076, Filgotinib, Ganetespib, INCB039110, INCB-047986, Itacitinib, JAK3-IN-1, JANEX-1, LFM-A13, LY2784544, NS-018, NSC42834, NVP-BSK805, Oclacitinib, Pacritinib, Peficitinib, Pyridone 6, R348, RGB-286638, Ruxolitinib, Ruxolitinib-S, SAR-20347, SB1317, Solcitinib, TG101209, TG101348, Tofacitinib(3R,4S), Tofacitinib(3S,4R), Tofacitinib(3S,4S), Tofacitinib, TYK2-IN-2, Upadacitinib, WHI-P154, WHI-P97, WP1066, XL019, ZM39923, and pharmaceutically acceptable salts thereof. In an embodiment, the JAK inhibitor is selected from the group consisting of Baricitinib phosphate, CYT387 Mesylate, CYT387 sulfate salt, NS-018 hydrochloride, NS-018 maleate, NVP-BSK805 dihydrochloride, Oclacitinib maleate, Ruxolitinib phosphate, Ruxolitinib sulfate, Tofacitinib citrate, and ZM39923 hydrochloride. In an embodiment, the PD-1 inhibitor is selected from group consisting of nivolumab, pembrolizumab, pidilizumab, AMP-224, AMP-514, PDR001, and fragments, conjugates, or variants thereof. In an embodiment, the PD-L1 inhibitor is an anti-PD-L1 antibody. In an embodiment, the PD-L1 inhibitor is selected from the group consisting of Atezolizumab, Avelumab, Durvalumab, BMS-936559, and fragments, conjugates, or variants thereof. In an embodiment, the anti-PD-L2 antibody is rHIgM12B7A. In an embodiment, the AKT inhibitor is selected from the group consisting of SB0203580, MK-2206, AZD5363, Miltefosine, Perifosine, PF-04691502, CCT128930, A-674563, RX-0201, PBI-05204, AKT inhibitor VIII, AT7867, AT13148, GDC-0068, TIC10, SC79, GSK690693, GSK2110183, GSK2141795, and pharmaceutically acceptable salts thereof. In an embodiment, the mTOR inhibitor is selected from the group consisting of Sirolimus, Everolimus, Temsirolimus, Zotarolimus, Deforolimus, Wortmannin, Ascomycin, Tacrolimus, KU-0063794, Sapanisertib, AZD8055, Vistusertib, CC-223, OSI-027, Voxtalisib, Palomid 529, PP 242, Dactolisib, BGT226, Apitolisib, Omipalisib, PF-04691502, Gedatolisib, and pharmaceutically acceptable salts thereof. In an embodiment, the PI3K inhibitor is selected from the group consisting of Buparlisib, Alpelisib, Pictilisib, Pilaralisib, Sonolisib, Copanlisib, CH5132799, Serabelisib, AZD8186, SAR260301, GSK2636771, Idelalisib, Acalisib, Duvelisib, Taselisib, AMG319, GDC-0084, and pharmaceutically acceptable salts thereof. In an embodiment, the IDH inhibitor is selected from the group consisting of Enasidenib, Ivosidenib, AGI-5198, AGI-6780, CHEMBL3682093, Vorasidenib, IDH-305, BAY-1436032, GSK864, (R,S)-Ivosidenib, IDH1-IN-2, IDH1-IN-1, Enasidenib mesylate, and pharmaceutically acceptable salts thereof. In an embodiment, the interferon is selected from the group consisting of interferon alpha (IFN-α), interferon beta (IFN-β), interferon lambda (IFN-λ), interferon gamma (IFN-γ), and combinations thereof. In an embodiment, the interferon is selected from the group consisting of interferon-alpha-2a, interferon-alpha-2b, interferon-alpha-2c, interferon-alpha-n1, interferon-alpha-n3, PEGylated interferon-alpha-2a, PEGylated interferon-alpha-2b, PEGylated interferon-alpha-2c, PEGylated interferon-alpha-n1, PEGylated interferon-alpha-n3, and combinations thereof.

In an embodiment, the MDM2 inhibitor is administered to a human intermittently; while the therapeutic agent is administered to a human non-intermittently. In an embodiment, the therapeutic agent is administered to a human intermittently; while the MDM2 inhibitor is administered to a human non-intermittently. In an embodiment, both the MDM2 inhibitor and the therapeutic agent are administered to a human intermittently. In an embodiment, both the MDM2 inhibitor and the therapeutic agent are administered to a human non-intermittently.

Methods of Treating a Myeloproliferative Neoplasm (MPN)

In an embodiment, the invention relates to a method of treating a MPN in a human that comprises the step of administering to said human a therapeutically effective amount of a MDM2 inhibitor and a therapeutic agent in a dosage independently selected from the group consisting of 15 mg QD, 25 mg QD, 30 mg QD, 50 mg QD, 60 mg QD, 75 mg QD, 100 mg QD, 120 mg QD, 150 mg QD, 175 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 100 mg BID, 120 mg BID, 150 mg BID, 175 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD). In an embodiment, the myelofibrosis is selected from the group consisting of primary myelofibrosis (PMF), post-polycythemia vera myelofibrosis (post-PV MF), and post-essential thrombocythemia myelofibrosis (post-ET MF). In an embodiment, the primary myelofibrosis (PMF) is selected from the group consisting of prefibrotic/ early stage PMF and overt fibrotic stage PMF. In an embodiment, the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T). In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, R08994, Nutlin-3, Nutlin-3a, Nutlin-3b, Serdemetan, NSC59984, CHEMBL2386350, MK-8242, DS-3032, DS-3032B, R06839921, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, R06839921, APG-115, MI-1601, and pharmaceutically acceptable salts thereof. In an embodiment, the JAK inhibitor is selected from the group consisting of AC-410, AT9283, AZ960, AZD-1480, Baricitinib, BMS-911543, CEP-33779, Cerdulatinib, CHZ868, CYT387, Decernotinib, ENMD-2076, Filgotinib, Ganetespib, INCB039110, INCB-047986, Itacitinib, JAK3-IN-1, JANEX-1, LFM-A13, LY2784544, NS-018, NSC42834, NVP-BSK805, Oclacitinib, Pacritinib, Peficitinib, Pyridone 6, R348, RGB-286638, Ruxolitinib, Ruxolitinib-S, SAR-20347, SB1317, Solcitinib, TG101209, TG101348, Tofacitinib(3R,4S), Tofacitinib(3S,4R), Tofacitinib(3S,4S), Tofacitinib, TYK2-IN-2, Upadacitinib, WHI-P154, WHI-P97, WP1066, XL019, ZM39923, and pharmaceutically acceptable salts thereof. In an embodiment, the JAK inhibitor is selected from the group consisting of Baricitinib phosphate, CYT387 Mesylate, CYT387 sulfate salt, NS-018 hydrochloride, NS-018 maleate, NVP-BSK805 dihydrochloride, Oclacitinib maleate, Ruxolitinib phosphate, Ruxolitinib sulfate, Tofacitinib citrate, and ZM39923 hydrochloride. In an embodiment, the PD-1 inhibitor is selected from group consisting of nivolumab, pembrolizumab, pidilizumab, AMP-224, AMP-514, PDR001, and fragments, conjugates, or variants thereof. In an embodiment, the PD-L1 inhibitor is an anti-PD-L1 antibody. In an embodiment, the PD-L1 inhibitor is selected from the group consisting of Atezolizumab, Avelumab, Durvalumab, BMS-936559, and fragments, conjugates, or variants thereof. In an embodiment, the anti-PD-L2 antibody is rHIgM12B7A. In an embodiment, the AKT inhibitor is selected from the group consisting of SB0203580, MK-2206, AZD5363, Miltefosine, Perifosine, PF-04691502, CCT128930, A-674563, RX-0201, PBI-05204, AKT inhibitor VIII, AT7867, AT13148, GDC-0068, TIC10, SC79, GSK690693, GSK2110183, GSK2141795, and pharmaceutically acceptable salts thereof. In an embodiment, the mTOR inhibitor is selected from the group consisting of Sirolimus, Everolimus, Temsirolimus, Zotarolimus, Deforolimus, Wortmannin, Ascomycin, Tacrolimus, KU-0063794, Sapanisertib, AZD8055, Vistusertib, CC-223, OSI-027, Voxtalisib, Palomid 529, PP 242, Dactolisib, BGT226, Apitolisib, Omipalisib, PF-04691502, Gedatolisib, and pharmaceutically acceptable salts thereof. In an embodiment, the PI3K inhibitor is selected from the group consisting of Buparlisib, Alpelisib, Pictilisib, Pilaralisib, Sonolisib, Copanlisib, CH5132799, Serabelisib, AZD8186, SAR260301, GSK2636771, Idelalisib, Acalisib, Duvelisib, Taselisib, AMG319, GDC-0084, and pharmaceutically acceptable salts thereof. In an embodiment, the IDH inhibitor is selected from the group consisting of Enasidenib, Ivosidenib, AGI-5198, AGI-6780, CHEMBL3682093, Vorasidenib, IDH-305, BAY-1436032, GSK864, (R,S)-Ivosidenib, IDH1-IN-2, IDH1-IN-1, Enasidenib mesylate, and pharmaceutically acceptable salts thereof. In an embodiment, the interferon is selected from the group consisting of interferon alpha (IFN-α), interferon beta (IFN-β), interferon lambda (IFN-λ), interferon gamma (IFN-γ), and combinations thereof. In an embodiment, the interferon is selected from the group consisting of interferon-alpha-2a, interferon-alpha-2b, interferon-alpha-2c, interferon-alpha-n1, interferon-alpha-n3, PEGylated interferon-alpha-2a, PEGylated interferon-alpha-2b, PEGylated interferon-alpha-2c, PEGylated interferon-alpha-n1, PEGylated interferon-alpha-n3, and combinations thereof.

In an embodiment, the invention relates to a combination of a therapeutically effective amount of a MDM2 inhibitor and a therapeutic agent for use of treating a MPN in a human, wherein the MDM2 inhibitor and the therapeutic agent are administered independently selected from the group consisting of 15 mg QD, 25 mg QD, 30 mg QD, 50 mg QD, 60 mg QD, 75 mg QD, 100 mg QD, 120 mg QD, 150 mg QD, 175 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 100 mg BID, 120 mg BID, 150 mg BID, 175 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD). In an embodiment, the myelofibrosis is selected from the group consisting of primary myelofibrosis (PMF), post-polycythemia vera myelofibrosis (post-PV MF), and post-essential thrombocythemia myelofibrosis (post-ET MF). In an embodiment, the primary myelofibrosis (PMF) is selected from the group consisting of prefibrotic/early stage PMF and overt fibrotic stage PMF. In an embodiment, the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T). In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, R08994, Nutlin-3, Nutlin-3a, Nutlin-3b, Serdemetan, NSC59984, CHEMBL2386350, MK-8242, DS-3032, DS-3032B, R06839921, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, R06839921, APG-115, MI-1601, and pharmaceutically acceptable salts thereof. In an embodiment, the JAK inhibitor is selected from the group consisting of AC-410, AT9283, AZ960, AZD-1480, Baricitinib, BMS-911543, CEP-33779, Cerdulatinib, CHZ868, CYT387, Decernotinib, ENMD-2076, Filgotinib, Ganetespib, INCB039110, INCB-047986, Itacitinib, JAK3-IN-1, JANEX-1, LFM-A13, LY2784544, NS-018, NSC42834, NVP-BSK805, Oclacitinib, Pacritinib, Peficitinib, Pyridone 6, R348, RGB-286638, Ruxolitinib, Ruxolitinib-S, SAR-20347, SB1317, Solcitinib, TG101209, TG101348, Tofacitinib(3R,4S), Tofacitinib(3S,4R), Tofacitinib(3S,4S), Tofacitinib, TYK2-IN-2, Upadacitinib, WHI-P154, WHI-P97, WP1066, XL019, ZM39923, and pharmaceutically acceptable salts thereof. In an embodiment, the JAK inhibitor is selected from the group consisting of Baricitinib phosphate, CYT387 Mesylate, CYT387 sulfate salt, NS-018 hydrochloride, NS-018 maleate, NVP-BSK805 dihydrochloride, Oclacitinib maleate, Ruxolitinib phosphate, Ruxolitinib sulfate, Tofacitinib citrate, and ZM39923 hydrochloride. In an embodiment, the PD-1 inhibitor is selected from group consisting of nivolumab, pembrolizumab, pidilizumab, AMP-224, AMP-514, PDR001, and fragments, conjugates, or variants thereof. In an embodiment, the PD-L1 inhibitor is an anti-PD-L1 antibody. In an embodiment, the PD-L1 inhibitor is selected from the group consisting of Atezolizumab, Avelumab, Durvalumab, BMS-936559, and fragments, conjugates, or variants thereof. In an embodiment, the anti-PD-L2 antibody is rHIgM12B7A. In an embodiment, the AKT inhibitor is selected from the group consisting of SB0203580, MK-2206, AZD5363, Miltefosine, Perifosine, PF-04691502, CCT128930, A-674563, RX-0201, PBI-05204, AKT inhibitor VIII, AT7867, AT13148, GDC-0068, TIC10, SC79, GSK690693, GSK2110183, GSK2141795, and pharmaceutically acceptable salts thereof. In an embodiment, the mTOR inhibitor is selected from the group consisting of Sirolimus, Everolimus, Temsirolimus, Zotarolimus, Deforolimus, Wortmannin, Ascomycin, Tacrolimus, KU-0063794, Sapanisertib, AZD8055, Vistusertib, CC-223, OSI-027, Voxtalisib, Palomid 529, PP 242, Dactolisib, BGT226, Apitolisib, Omipalisib, PF-04691502, Gedatolisib, and pharmaceutically acceptable salts thereof. In an embodiment, the PI3K inhibitor is selected from the group consisting of Buparlisib, Alpelisib, Pictilisib, Pilaralisib, Sonolisib, Copanlisib, CH5132799, Serabelisib, AZD8186, SAR260301, GSK2636771, Idelalisib, Acalisib, Duvelisib, Taselisib, AMG319, GDC-0084, and pharmaceutically acceptable salts thereof. In an embodiment, the IDH inhibitor is selected from the group consisting of Enasidenib, Ivosidenib, AGI-5198, AGI-6780, CHEMBL3682093, Vorasidenib, IDH-305, BAY-1436032, GSK864, (R,S)-Ivosidenib, IDH1-IN-2, IDH1-IN-1, Enasidenib mesylate, and pharmaceutically acceptable salts thereof. In an embodiment, the interferon is selected from the group consisting of interferon alpha (IFN-α), interferon beta (IFN-β), interferon lambda (IFN-λ), interferon gamma (IFN-γ), and combinations thereof. In an embodiment, the interferon is selected from the group consisting of interferon-alpha-2a, interferon-alpha-2b, interferon-alpha-2c, interferon-alpha-n1, interferon-alpha-n3, PEGylated interferon-alpha-2a, PEGylated interferon-alpha-2b, PEGylated interferon-alpha-2c, PEGylated interferon-alpha-n1, PEGylated interferon-alpha-n3, and combinations thereof.

The methods described above may be used as first-line cancer therapy, or after treatment with conventional chemotherapic active pharmaceutical ingredients, including cyclophosphamide, fludarabine (FC chemotherapy), and chlorambucil.

The combination of the MDM2 inhibitor and the therapeutic agent may also be used in combination with radiation therapy, hormone therapy, surgery and immunotherapy, which therapies are well known to those skilled in the art.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: Effects of the Combination of the Compound of Formula (I) with a Therapeutic Agent on Polycythemia Vera Cells The procedure of testing the effects of the combination of the compound of Formula (I) with a therapeutic agent on polycythemia vera cells follows that described in Lu, Blood, 2012, 120(15); 3098-3105, the entirety of which is incorporated by reference. The following describes the procedure briefly. The therapeutic agent is selected from the group consisting of a JAK inhibitor, an IDH inhibitor, a PD-1 inhibitor, a PD-L1 inhibitor, a PD-L2 inhibitor, an interferon, a PI3K inhibitor, an AKT inhibitor, an mTOR inhibitor, a nucleoside analog, and combinations thereof.

Cell Preparation:

Peripheral blood will be obtained from polycythemia vera (PV) patients. Appropriate approval will be obtained from the Institutional Review Board. Informed consent will be obtained before the study. All patients will meet the World Health Organization diagnostic criteria for polycythemia vera (PV). The peripheral blood samples are layered onto Ficoll-Hypaque (1.077 g/mL; GE Healthcare) and low-density mononuclear cells are separated via centrifugation. The CD34+ cells will be isolated using a human CD34+ cell selection kit (StemCell Technologies) according to the manufacturer's instructions. The purity of the CD34+ cell population will be analyzed using a FACSCalibur flow cytometer (BD Biosciences); and is required for at least 85% for all experiments. Fresh normal human bone marrow CD34+ cells will be purchased from ALLCELLS as a control.

HPC Assays

The effects of the compound of Formula (I) on polycythemia vera (PV) patients can be assessed by the HPC assays, described in Lu, Blood, 2012, 3098-3105, the entirety of which is incorporated by reference. In brief, CD34+ cells will be cultured in serum free medium (StemCell Technologies) containing 50 ng/mL stem cell factor (SCF), 50 ng/mL thrombopoietin (TPO), 50 ng/mL fms-like tyrosine kinase 3 (Flt-3) ligand, and 50 ng/mL IL-3, and will be treated with various dose of the compound of Formula (I) for 4 days. After 4 days of treatment, CD34+ cells will be assayed in semisolid media as described in Bruno, Blood, 2006, 3128-3134, the entirety of which is incorporated by reference. Briefly, $5 \times 10^2$ CD34+ cells will be plated per dish in duplicate cultures containing 1 mL IMDM with 1.1% methylcellulose and 20% FBS, to which SCF, TPO, Flt-3 ligand, IL-3, and GM-CSF at each 50 ng/mL, and 2 U/mL erythropoietin (EPO) will be added. Colonies will be enumerated after 14 days of incubation, and individual colonies will be plucked and genotyped for JAK2V617F.

Nested Allele-Specific PCR for JAK2V617F-Positive Colonies

Genomic DNA will be isolated from randomized plucked colonies using the Extract-N-Amp Blood PCR Kits (Sigma-Aldrich). JAK2V617F will be detected by using a nested allele-specific PCR as described in Bruno, Blood, 2006, 3128-3134, the entirety of which is incorporated by reference. The final PCR products will be analyzed on 2.0% agarose gels. A 279-bp product indicates allele-specific JAK2V617F-positive, whereas a 229-bp product indicates JAK2V617F-negative. Colonies will be classified as homozygous for JAK2V617F if they contained only the 279-bp band, whereas heterozygous colonies will be identified based on the presence of both the 279-bp and 229-bp bands.

Apoptosis Assay

Treated cells will be collected and washed with PBS for staining with annexin-V (BD Biosciences); the staining procedures will be performed according to the protocols provided by the manufacturer. Data will be acquired on a FACSCalibur flow cytometer (BD Biosciences), and at least 10 000 live cells will be acquired for each analysis (BD FACS Diva software; BD Biosciences).

Western Blot Analysis

CD34+ cells will be purified from the peripheral blood of patients with polycythemia vera (PV) and cultured in serum-free medium contained with SCF, FL-3 ligand, IL-3, and TPO. The cells will be treated with various dose of the compound of Formula (I) for 4 hours. Cells will be harvested and the whole cells protein extracts will be prepared with RIPA lysis buffer (Boston BioProducts) for Western blotting.

To prepare the cytoplasmic and nuclear protein fractions of cells from patients with polycythemia vera (PV), CD34+ cells will be expanded in serum-free media containing SCF, FL-3 ligand, and IL-3 for 10 days. CD34+ cells will be then repurified and treated with various doses of the compound of Formula (I) for 48 hours in the presence of SCF, FL-3 ligand, IL-3, and TPO. The protein extracts will be prepared using the NE-PER nuclear and cytoplasmic extraction reagent (Thermo Scientific) according to the manufacturer's instructions.

Before Western blotting, all the samples will be denatured with Laemmli SDS-sample buffer (Boston BioProducts) by heating at 95° C. for 5 minutes; each sample will be separated on SDS-PAGE gels and transferred to polyvinyldifluoridine membranes (Bio-Rad). Phospho-p53, p53, MDM2, p21, p-STAT1, PUMA, and Bak were visualized using the antibodies (Cell Signaling Technologies) and ECL Western blotting reagents (Denville Scientific).

Example 2. Modeling Transformation of JAK2V617F Mutated MPNs: Role of Interferon Alpha and MDM2 Inhibition in Prevention of Disease Progression Philadelphia chromosome-negative myeloproliferative neoplasms are clonal hematological malignancies characterized by increased proliferation of myeloid lineages, leading to an abnormally high number of mature blood cells. They comprise polycythemia vera (PV), essential thrombocytemia (ET) and primary myelofibrosis (PMF). At the opposite of PMF, PV and ET are chronic diseases with a median survival over 15 years. However, the major risk is the progression to secondary acute myeloid leukemia (sAML) associated to a very poor outcome. The hematopoietic stem or progenitor cells in MPN accumulate genetic and epigenetic alterations that model the phenotype and promote the hematologic evolution. The genomic landscape of sAML is close to that observed in therapy-related acute myeloid leukemia (tAML) with mutations of TP53. Indeed, leukemic transformation of PV and ET harbour TP53 mutations (loss of function mutation mainly) in approximatively 35-50% of cases.

Treatments are restricted to bone marrow transplantation when sAML develop, and currently available therapies (cytarabine, anthracyclines, hypomethylating agents etc.) remain poorly successful in such cases. Medical treatments for PMF developed to date are more or less only palliative (JAK2 inhibitors, hypomethylating agents, hydroxyurea) and don't prevent disease progression.

Modelling the myeloproliferation and the acute transformation in mice models harbouring JAK2V617F mutation and inactivated or not for TP53 and test in these models the influence on disease development of treatments with interferon-alpha (IFNa), the compound of Formula (I) or (II), or combination of both drugs.

In order to study disease progression in vivo, the cooperation of 2 mutations JAK2 with P53 deletion through mice models are studied. The inducible KI JAK2V617F mice will be used, which develop polycythemia, granulocytosis and thrombocytosis along with myelofibrosis. The JAK2V617F mutation is expressed in these CD45.2 mice after crossing with CD45.2 Tg(Vav-cre) A2Kio mice. The CD45.2 vav-cre mice crossed with the JAK2V617F induce a MPN in less than 6 weeks leading to development of myelofibrosis without leukemia in 6 months. These JAK2V617F KI mice and vav-cre will be crossed to P53 KO mice and then backcrossed in TP53KO background in order to obtain on one hand vav-cre/TP53 KO mice and JAK2V617F flox+/−/TP53 KO mice on the other hand. The two types of mice will be crossed to obtain CD45.2 vav-cre/JAK2V617F/TP53 KO mice.

The combination of JAK2V617F and P53KO has already been studied though retroviral mouse models, the mice develop AML with a massive expansion of erythromegakaryocytic progenitors. However, these studies used retroviral mouse models then the expression level of the transgene vary from one clone to another, and the JAK2V617F KI mice used here will be closer to what occurs in patients with expression of JAK2V617F at the same level in all stem cells.

Bone marrow transplanted cells will be used in order to mix normal and mutant cells in a mouse recipient. Then, bone marrow cells of the JAK2V617F mice marrow (CD45.2 phenotype), of the JAK2V617F/TP53 KO mice (CD45.2), or of CD451+2 normal mice will be sorted. A healthy mouse (WT) of CD45.1 phenotype, will serve as a host after irradiation. Either the JAK2V617F CD45.1 and the normal CD451+2 cells in CD45.2 background or the CD45.1 JAK2V617F/TP53 KO cells with CD451+2 normal cells in CD45.2 irradiated mice will be transplanted. The ratio of pathological cells versus normal cells will be 20/80, a ratio previously demonstrated as able to induce MPN in recipients in less than 2 months. Ten mice will be transplanted from one donor, leading to 10 grafted mice/pathological mouse. Groups of 20 mice will be studied.

To measure the impact of IFN alpha, the compound of Formula (I) or (II), or combination therapy on the potential effect on malignant clones, the grafted mice will be divided into four groups that will be treated at day 15 after BMT (normalization of blood cell count after transplant): one by IFN alpha, one by the compound of Formula (I) or (II), one by a combination of both drugs and one with PBS as control. Chimerism and phenotype (weight, hematologic parameters, etc.) will be analyzed every week (on blood), and on bone marrow chimerism in each stem cell and progenitor compartment (SLAM, Short term, progenitors) at months 1, 3 and 6. Secondary transplantations will be performed if chimerism demonstrates statistically significant modification in the blood. The monitoring of their hematological parameters will help detect the chronic disease, namely a PV/MF phase (increase in the number of red blood cells, platelets, etc.) or AML (increase in the number of circulating immature cells). If treatments modify the chimerism and allow for the selection of normal cells, in the group of treated mice, an increase in the percentage of CD451+2 cells leading to a lower rate or absence of transformation to AML will be observed. Such an outcome indicates that the treatments are able to reduce or cure the JAK2V617F clones and/or the P53 mutated/inactivated JAK2V617F sub-clones respectively.

Example 3: Effect of the Combination of the Compound of Formula (I) and Decitabine on MPN-BP Stem Cells NPN-BP Cell Preparation Currently, $CD3^+$ cell-depleted mononuclear cells (MNC) from 1 patient with MPN-BP who had WT TP53 gene have been shown to be capable of serially engrafting and causing leukemia in NSG mice. In order to harvest sufficient cells to assess the effects of the combination of the compound of Formula (I) and decitabine on MPN-BP stem cells, MPN-BP cells collected from the bone marrow (BM) or spleens of NSG mice will be passaged in NSG mice by serial transplantation. The mutational patterns and karyotypic abnormalities present in the cells following serial transplantation will be determined by capture based next generation sequencing (NGS) and fluorescence in situ hybridization (FISH).

Effects of the Combination of the Compound of Formula (I) and Decitabine

In order to examine the effects of the combination of the compound of Formula (I) and decitabine on MPN-BP stem cells, $0.5-2\times10^6$ cells/mouse harvested from NSG mice receiving MPN-BP cells will be transplanted into sublethally irradiated (220 cGy) 8-9-week-old NSG mice. The mice will then be monitored daily for their general condition and their body weight measured weekly. Twenty-eight days after transplantation, peripheral blood from the recipient mice will be collected and analyzed with the performance of complete blood counts (CBC) and flow cytometric analysis to determine if human MPN-BP has developed in these mice. These mice will be used in the following studies.

High Dose Study of the Compound of Formula (I) or Decetabine

The mice that have developed MPN-BP and have a similar leukemic burden in peripheral blood will be randomly divided into 4 groups of 3-4 mice. Two groups of mice will be treated with vehicle or the compound of Formula (I) (high dose, either 100 or 150 mg/kg) by oral gavage once per day for 7 days. The other two groups of mice will be treated with vehicle or decitabine at 5 mg/kg by IP injection 3 times/week for 7 days. After the treatment, peripheral blood blast count will be monitored using flow cytometric analysis weekly. Tolerability to the treatment will be assessed by daily body weight (BW) measurements. These analyses will allow to establish dynamics of MPN-BP return following each drug treatment which will be used to determine the treatment-free interval for the following survival and combination treatment studies.

Combination Treatment with Low Doses of the Compound of Formula (I) and Decitabine NSG mice engrafted with MPN-BP cells will be randomly assigned to 4 groups of 4-5 mice. These mice will be treated with the compound of Formula (I), decitabine alone or in combination as following. Group 1: the compound of Formula (I)+PBS; Group; 2: Vehicle+decitabine; Group 3: the compound of Formula (I)+decitabine; Group 4: Vehicle+ PBS. The compound of Formula (I) at 30-50 mg/kg or vehicle will be dosed once daily by oral gavage on days 1-7 for 7 days. Decitabine (2.5 mg/kg) or PBS will be dosed by IP injection 3 times/week for 7 days. Treatments will be repeated for up to 3 cycles. After the treatment, survival and disease progression will be monitored and mice will be sacrificed and analyzed. After the mice are sacrificed, cells will be recovered from the BM, spleen, and the peripheral blood. The presence of human $CD45^+$, $CD34^+$, $CD33^+$, $CD14^+$, Gly $A^+$, $CD41a^+$, $CD19^+$, and $CD3^+$ cells in these organs will be determined by mAb staining and flow cytometric analysis.

Example 4: An Open-Label, Multicenter, Phase 1b/2 Study of the Safety and Efficacy of the Compound of Formula I Combined with Low-Dose Cytarabine (LDAC) or Decitabine in Patients with Acute Myeloid Leukemia (AML)

All subjects will receive the compound of formula I combined with low-dose cytarabine (LDAC) or decitabine. Dosing Formulation for the compound of formula I: this compound is formulated as an immediate-release, oral, solid dosage form, in tablet strengths of 15 mg and 60 mg. For administration: the compound of formula I should be taken on an empty stomach in the morning (no food or liquids except water 2 hours prior to drug) and refrain from food and liquid intake (except water) for 2 hours post dose. Tablets should not be crushed, chewed, or dissolved in water. The compound of formula I will be administered on Days 1 through 7 of every treatment cycle, which is 28 days.

For cytarabine, LDAC will be administered at 20 mg/m2/day by subcutaneous (SC) injection once daily on Days 1 through 10 of each 28-day cycle. For decitabine, it will be administered at 20 mg/m2/day intravenously (IV) once daily on Days 1 through 5 of each 28-day cycle.

Study Polulation
  Part A (Phase 1b): The subject population will consist of male or female individuals age 18 years or older with relapsed or refractory AML.
  Part B (Phase 2): The subject population will consist of male or female individuals age 18 years or older with newly diagnosed or relapsed or refractory AML secondary to myeloproliferative neoplasms (MPN).

Study Treatments

All subjects will receive the compound of formula I combined with low-dose cytarabine (LDAC) or decitabine.

Study Design

Part A (Phase 1b): The phase 1b portion of the study follows a 3+3 dose-escalation design to determine the recommended phase 2 dose (RP2D) of the compound of formula I for the phase 2 portion of the study. The investigator may assign subjects to either Cohort 1 (LDAC) or Cohort 2 (decitabine) if there are open spots for enrollment in that cohort, and if the subject meets eligibility criteria for that cohort.

Compound of formula I Dose Level 1 (Starting Dose): 240 mg orally once daily administered on Days 1 through 7 of each 28-day cycle in combination with LDAC at 20 mg/m$^2$/day SC once daily on Days 1 through 10 of each 28-day cycle (Cohort 1A, n=3 to 6 subjects), or Decitabine 20 mg/m$^2$/day IV once daily on Days 1 through 5 of each 28-day cycle (Cohort 2A, n=3 to 6 subjects).

If there are no dose-limiting toxicities (DLTs) in the first 3 subjects enrolled in Dose Level 1 (Cohort 1A or Cohort 2A), Dose Level 2 will open for that cohort. If there is at least 1 DLT among the first 3 subjects enrolled in Cohort 1A or Cohort 2A, then 3 additional subjects will be added to the cohort in which the DLT occurred, for a total of 6 subjects in the cohort. If there is <1 DLT among the 6 subjects in a cohort, then Dose Level 2 will open for that cohort. If there are 2 or more DLTs in Cohort 1A or Cohort 2A, then the Dose Level 1 Step-Down cohorts will open.

Dose Level 1 Step-Down Cohorts: 180 mg of the compound of formula I orally once daily administered on Days 1 through 7 of each 28-day cycle in combination with LDAC at 20 mg/m$^2$/day SC once daily on Days 1 through 10 of each 28-day cycle (Cohort 1A-1, n=3 to 6 subjects), or Decitabine 20 mg/m2/day IV once daily on Days 1 through 5 of each 28-day cycle (Cohort 2A-1, n=3 to 6 subjects). If there are no DLTs among the first 3 subjects enrolled in the Dose Level 1 Step-Down (Cohort 1A-1 or Cohort 2A-1), then the Dose Level 1 Step-Down will be declared the RP2D for that cohort. If there is at least 1 DLT among the first 3 subjects enrolled in Cohort 1A-1 or Cohort 2A-1, 3 additional subjects will be added to the cohort in which the DLT occurred, for a total of 6 subjects in the cohort. If there is <1 DLT among the 6 subjects in a cohort, then the Dose Level 1 Step-Down will be declared the recommended RP2D for the cohort. If there are 2 or more DLTs at the Dose Level 1 Step-Down (Cohort 1A-1 or Cohort 2A-1), then that cohort will be closed.

Dose Level 2: 360 mg of the compound of formula I orally once daily administered on Days 1 through 7 of each 28-day cycle in combination with LDAC at 20 mg/m$^2$/day SC once daily on Days 1 through 10 of each 28-day cycle (Cohort 1B, n=3 to 6 subjects), or decitabine 20 mg/m$^2$/day IV once daily on Days 1 through 5 of each 28-day cycle (Cohort 2B, n=3 to 6 subjects). If there are no DLTs among the first 3 subjects enrolled in Dose Level 2 (Cohort 1B or Cohort 2B), then the compound of formula I Dose Level 3 will open for that cohort. If there is at least 1 DLT among the 3 subjects enrolled in Dose Level 2 (Cohort 1B or Cohort 2B), then 3 additional subjects will be added to the cohort in which the DLT occurred, for a total of 6 subjects in the cohort. If there is <1 DLT among the 6 subjects in a cohort, then Dose Level 3 will open for that Cohort. If there are 2 or more DLTs in Cohort 1B or Cohort 2B, then the Dose Level 2 Step-Down cohorts will open.

Dose Level 2 Step-Down Cohorts: 300 mg of the compound of formula I orally once daily administered on Days 1 through 7 of each 28-day cycle in combination with LDAC at 20 mg/m$^2$/day SC once daily on Days 1 through 10 of each 28-day cycle (Cohort 1B-1, n=3 to 6 subjects), or decitabine 20 mg/m$^2$/day IV once daily on Days 1 through 5 of each 28-day cycle (Cohort 2B-1, n=3 to 6 subjects). If there are no DLTs among the first 3 subjects enrolled in the Dose Level 2 Step-Down (Cohort 1B-1 or Cohort 2B-1), then the Dose Level 2 Step-Down will be declared the RP2D for that cohort. If there is at least 1 DLT among the first 3 subjects enrolled in Cohort 1B-1 or Cohort 2B-1, 3 additional subjects will be added to the cohort in which the DLT occurred, for a total of 6 subjects in the cohort. If there is <1 DLT among the 6 subjects in a cohort, then the Dose Level 2 Step-Down will be declared the recommended RP2D for the cohort. If there are 2 or more DLTs at the Dose Level 2 Step-Down (Cohort 1B-1 or Cohort 2B-1), then Dose Level 1 for that cohort will be declared the RP2D.

Dose Level 3: Cycle 1 only: 480 mg of the compound of formula I orally once daily administered on Days 1 through 7 of the first 28-day cycle in combination with LDAC or decitabine. Cycle 2 and beyond: 360 mg of the compound of formula I orally once daily administered on Days 1 through 7 of each 28-day cycle in combination with LDAC or decitabine. LDAC at 20 mg/m$^2$/day SC once daily on Days 1 through 10 of each 28-day cycle (Cohort 1C, n=3 to 6 subjects), or decitabine 20 mg/m$^2$/day IV once daily on Days 1 through 5 of each 28-day cycle (Cohort 2C, n=3 to 6 subjects). If there are no DLTs among the first 3 subjects enrolled in Cohort 1C or Cohort 2C, then Dose Level 3 will be considered the RP2D for the cohort. If there is at least 1 DLT among the first 3 subjects enrolled in Cohort 1C or Cohort 2C, then 3 additional subjects will be added to the cohort in which the DLT occurred, for a total of 6 subjects in the cohort. If there is <1 DLT among the 6 subjects in a cohort, that dose of will be declared the RP2D for the cohort. If there are 2 or more DLTs in Cohort 1C or Cohort 2C, then the Dose Level 3 Step-Down cohorts will open.

Dose Level 3 Step-Down Cohorts: Cycle 1 only will be 420 mg of the compound of formula I orally once daily administered on Days 1 through 7 of the first 28-day cycle in combination with LDAC or decitabine. Cycle 2 and beyond: 360 mg of the compound of formula I orally once daily administered on Days 1 through 7 of each 28-day cycle in combination with LDAC or decitabine. LDAC at 20 mg/m$^2$/day SC once daily on Days 1 through 10 of each 28-day cycle (Cohort 1C-1, n=3 to 6 subjects), or decitabine 20 mg/m2/day IV once daily on Days 1 through 5 of each 28-day cycle (Cohort 2C-1, n=3 to 6 subjects). If there are no DLTs among the first 3 subjects enrolled in the Dose Level 3 Step-Down (Cohort 1C-1 or Cohort 2C-1), then the Dose Level 3 Step-Down will be declared the RP2D for that cohort. If there is at least 1 DLT among the first 3 subjects enrolled in Cohort 1C-1 or Cohort 2C-1, 3 additional subjects will be added to the cohort in which the DLT occurred, for a total of 6 subjects in the cohort. If there is <1 DLT among the 6 subjects in a cohort, then the Dose Level 3 Step-Down will be declared the recommended RP2D for the cohort. If there are 2 or more DLTs at the Dose Level 3 Step-Down (Cohort 1C-1 or Cohort 2C-1), then Dose Level 2 for that cohort will be declared the RP2D.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

The invention claimed is:

1. A method of treating a myeloproliferative neoplasm (MPN) comprising administering to a human in need thereof, therapeutically effective amounts of a MDM2 inhibitor in combination with a JAK inhibitor, wherein the MDM2 inhibitor is a compound of Formula (I):

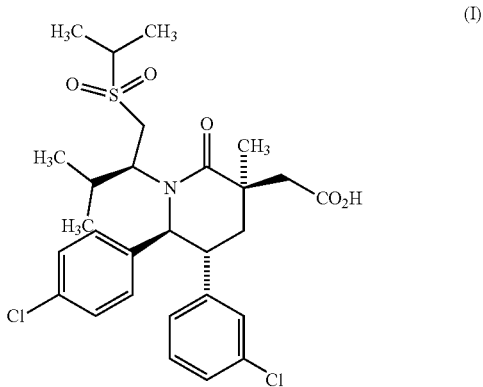

or a pharmaceutically acceptable salt thereof.

2. The method of claim 1, wherein the MPN is polycythemia vera (PV).

3. The method of claim 1, wherein the MPN is thrombocythemia.

4. The method of claim 3, wherein thrombocythemia is essential thrombocythemia (ET).

5. The method of claim 1, wherein the MPN is myelofibrosis.

6. The method of claim 5, wherein the myelofibrosis is selected from primary myelofibrosis (PMF), post-polycythemia vera myelofibrosis (post-PV MF), and post-essential thrombocythemia myelofibrosis (post-ET MF).

7. The method of claim 1, wherein the JAK inhibitor is selected from the group consisting of AC-410, AT9283, AZ960, AZD-1480, Baricitinib, BMS-911543, CEP-33779, Cerdulatinib, CHZ868, CYT387, Decernotinib, ENMD-2076, Filgotinib, Ganetespib, INCB039110, INCB-047986, Itacitinib, JAK3-IN-1, JANEX-1, LFM-A13, LY2784544, NS-018, NSC42834, NVP-BSK805, Oclacitinib, Pacritinib, Peficitinib, Pyridone 6, R348, RGB-286638, Ruxolitinib, Ruxolitinib-S, SAR-20347, SB1317, Solcitinib, TG101209, TG101348, Tofacitinib (3R,4S), Tofacitinib (3S,4R), Tofacitinib (3S,4S), Tofacitinib, TYK2-IN-2, Upadacitinib, WHI-P154, WHI-P97, WP1066, XL019, ZM39923, and pharmaceutically acceptable salts thereof.

8. The method of claim 1, wherein the MPN in the human subject has a JAK2V617F mutation.

9. The method of claim 1, wherein the JAK inhibitor is Ruxolitinib.

10. The method of claim 1, wherein the JAK inhibitor is (R)-3-(4-(7H-pyrrolo[2,3-d]pyrimidin-4-yl)-1H-pyrazol-1-yl)-3-cyclopentylpropanenitrile phosphate.

11. The method of claim 1, wherein the compound of Formula (I) or a pharmaceutically acceptable salt thereof is administered once daily at a dose of 240 mg.

12. The method of claim 1, wherein the compound of Formula (I) or a pharmaceutically acceptable salt thereof is administered on days 1 through 7 of each 28-day treatment cycle.

* * * * *

SEQUENCE LISTING

<160> NUMBER OF SEQ ID NOS: 106

<210> SEQ ID NO 1
<211> LENGTH: 440
<212> TYPE: PRT
<213> ORGANISM: Artificial Sequence
<220> FEATURE:
<223> OTHER INFORMATION: nivolumab heavy chain

<400> SEQUENCE: 1

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val

```
                35                  40                  45
Ala Val Ile Trp Tyr Asp Gly Ser Lys Arg Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
                100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 2
```

```
<211> LENGTH: 214
<212> TYPE: PRT
<213> ORGANISM: Artificial Sequence
<220> FEATURE:
<223> OTHER INFORMATION: nivolumab light chain

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 113
<212> TYPE: PRT
<213> ORGANISM: Artificial Sequence
<220> FEATURE:
<223> OTHER INFORMATION: nivolumab variable heavy chain

<400> SEQUENCE: 3

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
```

```
                    100                 105                 110
Ser

<210> SEQ ID NO 4
<211> LENGTH: 107
<212> TYPE: PRT
<213> ORGANISM: Artificial Sequence
<220> FEATURE:
<223> OTHER INFORMATION: nivolumab variable light chain

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 5
<211> LENGTH: 5
<212> TYPE: PRT
<213> ORGANISM: Artificial Sequence
<220> FEATURE:
<223> OTHER INFORMATION: nivolumab heavy chain CDR1

<400> SEQUENCE: 5

Asn Ser Gly Met His
1               5

<210> SEQ ID NO 6
<211> LENGTH: 17
<212> TYPE: PRT
<213> ORGANISM: Artificial Sequence
<220> FEATURE:
<223> OTHER INFORMATION: nivolumab heavy chain CDR2

<400> SEQUENCE: 6

Val Ile Trp Tyr Asp Gly Ser Lys Arg Tyr Tyr Ala Asp Ser Val Lys
1               5                   10                  15

Gly

<210> SEQ ID NO 7
<211> LENGTH: 4
<212> TYPE: PRT
<213> ORGANISM: Artificial Sequence
<220> FEATURE:
<223> OTHER INFORMATION: nivolumab heavy chain CDR3

<400> SEQUENCE: 7

Asn Asp Asp Tyr
1

<210> SEQ ID NO 8
<211> LENGTH: 11
```

```
<212> TYPE: PRT
<213> ORGANISM: Artificial Sequence
<220> FEATURE:
<223> OTHER INFORMATION: nivolumab light chain CDR1

<400> SEQUENCE: 8

Arg Ala Ser Gln Ser Val Ser Ser Tyr Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: nivolumab light chain CDR2

<400> SEQUENCE: 9

Asp Ala Ser Asn Arg Ala Thr
1               5

<210> SEQ ID NO 10
<211> LENGTH: 9
<212> TYPE: PRT
<213> ORGANISM: Artificial Sequence
<220> FEATURE:
<223> OTHER INFORMATION: nivolumab light chain CDR3

<400> SEQUENCE: 10

Gln Gln Ser Ser Asn Trp Pro Arg Thr
1               5

<210> SEQ ID NO 11
<211> LENGTH: 466
<212> TYPE: PRT
<213> ORGANISM: Artificial Sequence
<220> FEATURE:
<223> OTHER INFORMATION: pembrolizumab heavy chain

<400> SEQUENCE: 11

Met Ala Val Leu Gly Leu Leu Phe Cys Leu Val Thr Phe Pro Ser Cys
1               5                   10                  15

Val Leu Ser Gln Val Gln Leu Val Gln Ser Gly Val Glu Val Lys Lys
                20                  25                  30

Pro Gly Ala Ser Val Lys Val Ser Cys Lys Ala Ser Gly Tyr Thr Phe
            35                  40                  45

Thr Asn Tyr Tyr Met Tyr Trp Val Arg Gln Ala Pro Gly Gln Gly Leu
        50                  55                  60

Glu Trp Met Gly Gly Ile Asn Pro Ser Asn Gly Gly Thr Asn Phe Asn
65                  70                  75                  80

Glu Lys Phe Lys Asn Arg Val Thr Leu Thr Thr Asp Ser Ser Thr Thr
                85                  90                  95

Thr Ala Tyr Met Glu Leu Lys Ser Leu Gln Phe Asp Asp Thr Ala Val
            100                 105                 110

Tyr Tyr Cys Ala Arg Arg Asp Tyr Arg Phe Asp Met Gly Phe Asp Tyr
        115                 120                 125

Trp Gly Gln Gly Thr Thr Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175
```

-continued

```
Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys
465

<210> SEQ ID NO 12
<211> LENGTH: 447
<212> TYPE: PRT
<213> ORGANISM: Artificial Sequence
<220> FEATURE:
<223> OTHER INFORMATION: pembrolizumab heavy chain

<400> SEQUENCE: 12

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60
```

```
Lys Asn Arg Val Thr Leu Thr Thr Asp Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 13
<211> LENGTH: 130
<212> TYPE: PRT
<213> ORGANISM: Artificial Sequence
<220> FEATURE:
<223> OTHER INFORMATION: pembrolizumab variable light chainamino acid
```

<400> SEQUENCE: 13

```
Met Ala Pro Val Gln Leu Leu Gly Leu Leu Val Leu Phe Leu Pro Ala
1               5                   10                  15

Met Arg Cys Glu Ile Val Leu Thr Gln Ser Pro Ala Thr Leu Ser Leu
            20                  25                  30

Ser Pro Gly Glu Arg Ala Thr Leu Ser Cys Arg Ala Ser Lys Gly Val
        35                  40                  45

Ser Thr Ser Gly Tyr Ser Tyr Leu His Trp Tyr Gln Gln Lys Pro Gly
    50                  55                  60

Gln Ala Pro Arg Leu Leu Ile Tyr Leu Ala Ser Tyr Leu Glu Ser Gly
65                  70                  75                  80

Val Pro Ala Arg Phe Ser Gly Ser Gly Ser Gly Thr Asp Phe Thr Leu
                85                  90                  95

Thr Ile Ser Ser Leu Glu Pro Glu Asp Phe Ala Val Tyr Tyr Cys Gln
                100                 105                 110

His Ser Arg Asp Leu Pro Leu Thr Phe Gly Gly Gly Thr Lys Val Glu
            115                 120                 125

Ile Lys
    130
```

<210> SEQ ID NO 14
<211> LENGTH: 237
<212> TYPE: PRT
<213> ORGANISM: Artificial Sequence
<220> FEATURE:
<223> OTHER INFORMATION: pembrolizumab light chain

<400> SEQUENCE: 14

```
Met Ala Pro Val Gln Leu Leu Gly Leu Leu Val Leu Phe Leu Pro Ala
1               5                   10                  15

Met Arg Cys Glu Ile Val Leu Thr Gln Ser Pro Ala Thr Leu Ser Leu
            20                  25                  30

Ser Pro Gly Glu Arg Ala Thr Leu Ser Cys Arg Ala Ser Lys Gly Val
        35                  40                  45

Ser Thr Ser Gly Tyr Ser Tyr Leu His Trp Tyr Gln Gln Lys Pro Gly
    50                  55                  60

Gln Ala Pro Arg Leu Leu Ile Tyr Leu Ala Ser Tyr Leu Glu Ser Gly
65                  70                  75                  80

Val Pro Ala Arg Phe Ser Gly Ser Gly Ser Gly Thr Asp Phe Thr Leu
                85                  90                  95

Thr Ile Ser Ser Leu Glu Pro Glu Asp Phe Ala Val Tyr Tyr Cys Gln
                100                 105                 110

His Ser Arg Asp Leu Pro Leu Thr Phe Gly Gly Gly Thr Lys Val Glu
            115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205
```

```
Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 15
<211> LENGTH: 15
<212> TYPE: PRT
<213> ORGANISM: Artificial Sequence
<220> FEATURE:
<223> OTHER INFORMATION: pembrolizumab light chain CDR1

<400> SEQUENCE: 15

Arg Ala Ser Lys Gly Val Ser Thr Ser Gly Tyr Ser Tyr Leu His
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: pembrolizumab light chain CDR2

<400> SEQUENCE: 16

Leu Ala Ser Tyr Leu Glu Ser
1               5

<210> SEQ ID NO 17
<211> LENGTH: 9
<212> TYPE: PRT
<213> ORGANISM: Artificial Sequence
<220> FEATURE:
<223> OTHER INFORMATION: pembrolizumab light chain CDR3

<400> SEQUENCE: 17

Gln His Ser Arg Asp Leu Pro Leu Thr
1               5

<210> SEQ ID NO 18
<211> LENGTH: 5
<212> TYPE: PRT
<213> ORGANISM: Artificial Sequence
<220> FEATURE:
<223> OTHER INFORMATION: pembrolizumab heavy chain CDR1

<400> SEQUENCE: 18

Asn Tyr Tyr Met Tyr
1               5

<210> SEQ ID NO 19
<211> LENGTH: 16
<212> TYPE: PRT
<213> ORGANISM: Artificial Sequence
<220> FEATURE:
<223> OTHER INFORMATION: pembrolizumab heavy chain CDR2

<400> SEQUENCE: 19

Gly Ile Asn Pro Ser Asn Gly Gly Thr Asn Phe Asn Glu Lys Phe Lys
1               5                   10                  15

<210> SEQ ID NO 20
<211> LENGTH: 11
<212> TYPE: PRT
<213> ORGANISM: Artificial Sequence
<220> FEATURE:
<223> OTHER INFORMATION: pembrolizumab heavy chain CDR3
```

```
<400> SEQUENCE: 20

Arg Asp Tyr Arg Phe Asp Met Gly Phe Asp Tyr
1               5                   10

<210> SEQ ID NO 21
<211> LENGTH: 447
<212> TYPE: PRT
<213> ORGANISM: Artificial Sequence
<220> FEATURE:
<223> OTHER INFORMATION: pidilizumab heavy chain

<400> SEQUENCE: 21

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
```

```
                340             345             350
Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445
```

<210> SEQ ID NO 22
<211> LENGTH: 213
<212> TYPE: PRT
<213> ORGANISM: Artificial Sequence
<220> FEATURE:
<223> OTHER INFORMATION: pidilizumab light chain

<400> SEQUENCE: 22

```
Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
                20                  25                  30

His Trp Phe Gln Gln Lys Pro Gly Lys Ala Pro Lys Leu Trp Ile Tyr
            35                  40                  45

Arg Thr Ser Asn Leu Ala Ser Gly Val Pro Ser Arg Phe Ser Gly Ser
        50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
    210
```

<210> SEQ ID NO 23
<211> LENGTH: 117
<212> TYPE: PRT
<213> ORGANISM: Artificial Sequence
<220> FEATURE:
<223> OTHER INFORMATION: pidilizumab variable heavy chain

<400> SEQUENCE: 23

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser
            115

<210> SEQ ID NO 24
<211> LENGTH: 106
<212> TYPE: PRT
<213> ORGANISM: Artificial Sequence
<220> FEATURE:
<223> OTHER INFORMATION: pidilizumab variable light chain

<400> SEQUENCE: 24

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 25
<211> LENGTH: 7
<212> TYPE: PRT
<213> ORGANISM: Artificial Sequence
<220> FEATURE:
<223> OTHER INFORMATION: Synthetic

<400> SEQUENCE: 25

Ser Asn Thr Ser Glu Ser Phe
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic

```
<400> SEQUENCE: 26

Phe Ser Glu Ser Thr Asn Ser
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic

<400> SEQUENCE: 27

Ser Asn Thr Ser Glu Ser Phe
1               5

<210> SEQ ID NO 28
<211> LENGTH: 14
<212> TYPE: PRT
<213> ORGANISM: Artificial Sequence
<220> FEATURE:
<223> OTHER INFORMATION: Synthetic

<400> SEQUENCE: 28

Phe Arg Val Thr Gln Leu Ala Pro Lys Ala Gln Ile Lys Glu
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthetic

<400> SEQUENCE: 29

Phe Ser Glu Ser Thr Asn Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic

<400> SEQUENCE: 30

Ser Asn Thr Ser Glu Ser Phe
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic

<400> SEQUENCE: 31

Phe Arg Val Thr Gln Leu Ala Pro
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic

<400> SEQUENCE: 32
```

```
Ala Gln Ile Lys Glu
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic

<400> SEQUENCE: 33

Phe Ser Glu Ser Thr Asn Ser
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic

<400> SEQUENCE: 34

Ser Asn Thr Ser Glu Ser Phe
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic

<400> SEQUENCE: 35

Phe Arg Val Thr Gln Leu Ala Pro
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic

<400> SEQUENCE: 36

Ala Gln Ile Lys Glu
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic

<400> SEQUENCE: 37

Ser Asn Thr Ser Glu Ser Phe Lys
1               5

<210> SEQ ID NO 38
<211> LENGTH: 13
<212> TYPE: PRT
<213> ORGANISM: Artificial Sequence
<220> FEATURE:
<223> OTHER INFORMATION: Synthetic

<400> SEQUENCE: 38
```

Phe Arg Val Thr Gln Leu Ala Pro Lys Ala Gln Ile Lys
1               5                   10

<210> SEQ ID NO 39
<211> LENGTH: 451
<212> TYPE: PRT
<213> ORGANISM: Artificial Sequence
<220> FEATURE:
<223> OTHER INFORMATION: durvalumab (MEDI4736) heavy chain

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

```
Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 40
<211> LENGTH: 265
<212> TYPE: PRT
<213> ORGANISM: Artificial Sequence
<220> FEATURE:
<223> OTHER INFORMATION: durvalumab (MEDI4736) light chain

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Glu Ile Val Leu Thr Gln Ser Pro Gly Thr Leu Ser Leu Ser
    50                  55                  60

Pro Gly Glu Arg Ala Thr Leu Ser Cys Arg Ala Ser Gln Arg Val Ser
65                  70                  75                  80

Ser Ser Tyr Leu Ala Trp Tyr Gln Gln Lys Pro Gly Gln Ala Pro Arg
                85                  90                  95

Leu Leu Ile Tyr Asp Ala Ser Ser Arg Ala Thr Gly Ile Pro Asp Arg
            100                 105                 110

Phe Ser Gly Ser Gly Ser Gly Thr Asp Phe Thr Leu Thr Ile Ser Arg
        115                 120                 125

Leu Glu Pro Glu Asp Phe Ala Val Tyr Tyr Cys Gln Gln Tyr Gly Ser
    130                 135                 140

Leu Pro Trp Thr Phe Gly Gln Gly Thr Lys Val Glu Ile Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255
```

Thr Lys Ser Phe Asn Arg Gly Glu Cys
         260                 265

<210> SEQ ID NO 41
<211> LENGTH: 121
<212> TYPE: PRT
<213> ORGANISM: Artificial Sequence
<220> FEATURE:
<223> OTHER INFORMATION: durvalumab (MEDI4736) variable heavy chain

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 42
<211> LENGTH: 108
<212> TYPE: PRT
<213> ORGANISM: Artificial Sequence
<220> FEATURE:
<223> OTHER INFORMATION: durvalumab (MEDI4736) variable light chain

<400> SEQUENCE: 42

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 43
<211> LENGTH: 5
<212> TYPE: PRT
<213> ORGANISM: Artificial Sequence
<220> FEATURE:
<223> OTHER INFORMATION: durvalumab (MEDI4736) heavy chain CDR1

<400> SEQUENCE: 43

Arg Tyr Trp Met Ser

```
<210> SEQ ID NO 44
<211> LENGTH: 17
<212> TYPE: PRT
<213> ORGANISM: Artificial Sequence
<220> FEATURE:
<223> OTHER INFORMATION: durvalumab (MEDI4736) heavy chain CDR2

<400> SEQUENCE: 44

Asn Ile Lys Gln Asp Gly Ser Glu Lys Tyr Tyr Val Asp Ser Val Lys
1               5                   10                  15
Gly

<210> SEQ ID NO 45
<211> LENGTH: 12
<212> TYPE: PRT
<213> ORGANISM: Artificial Sequence
<220> FEATURE:
<223> OTHER INFORMATION: durvalumab (MEDI4736) heavy chain CDR3

<400> SEQUENCE: 45

Glu Gly Gly Trp Phe Gly Glu Leu Ala Phe Asp Tyr
1               5                   10

<210> SEQ ID NO 46
<211> LENGTH: 12
<212> TYPE: PRT
<213> ORGANISM: Artificial Sequence
<220> FEATURE:
<223> OTHER INFORMATION: durvalumab (MEDI4736) light chain CDR1

<400> SEQUENCE: 46

Arg Ala Ser Gln Arg Val Ser Ser Ser Tyr Leu Ala
1               5                   10

<210> SEQ ID NO 47
<211> LENGTH: 7
<212> TYPE: PRT
<213> ORGANISM: Artificial Sequence
<220> FEATURE:
<223> OTHER INFORMATION: durvalumab (MEDI4736) light chain CDR2

<400> SEQUENCE: 47

Asp Ala Ser Ser Arg Ala Thr
1               5

<210> SEQ ID NO 48
<211> LENGTH: 9
<212> TYPE: PRT
<213> ORGANISM: Artificial Sequence
<220> FEATURE:
<223> OTHER INFORMATION: durvalumab (MEDI4736) light chain CDR3

<400> SEQUENCE: 48

Gln Gln Tyr Gly Ser Leu Pro Trp Thr
1               5

<210> SEQ ID NO 49
<211> LENGTH: 5
<212> TYPE: PRT
<213> ORGANISM: Artificial Sequence
<220> FEATURE:
<223> OTHER INFORMATION: durvalumab alternative heavy chain CDR1

<400> SEQUENCE: 49
```

Thr Tyr Ser Met Asn
1               5

<210> SEQ ID NO 50
<211> LENGTH: 17
<212> TYPE: PRT
<213> ORGANISM: Artificial Sequence
<220> FEATURE:
<223> OTHER INFORMATION: durvalumab alternative heavy chain CDR2

<400> SEQUENCE: 50

Ser Ile Ser Ser Ser Gly Asp Tyr Ile Tyr Tyr Ala Asp Ser Val Lys
1               5                   10                  15

Gly

<210> SEQ ID NO 51
<211> LENGTH: 11
<212> TYPE: PRT
<213> ORGANISM: Artificial Sequence
<220> FEATURE:
<223> OTHER INFORMATION: durvalumab alternative heavy chain CDR3

<400> SEQUENCE: 51

Asp Leu Val Thr Ser Met Val Ala Phe Asp Tyr
1               5                   10

<210> SEQ ID NO 52
<211> LENGTH: 11
<212> TYPE: PRT
<213> ORGANISM: Artificial Sequence
<220> FEATURE:
<223> OTHER INFORMATION: durvalumab alternative light chain CDR1

<400> SEQUENCE: 52

Ser Gly Asp Ala Leu Pro Gln Lys Tyr Val Phe
1               5                   10

<210> SEQ ID NO 53
<211> LENGTH: 7
<212> TYPE: PRT
<213> ORGANISM: Artificial Sequence
<220> FEATURE:
<223> OTHER INFORMATION: durvalumab alternative light chain CDR2

<400> SEQUENCE: 53

Glu Asp Ser Lys Arg Pro Ser
1               5

<210> SEQ ID NO 54
<211> LENGTH: 11
<212> TYPE: PRT
<213> ORGANISM: Artificial Sequence
<220> FEATURE:
<223> OTHER INFORMATION: durvalumab alternative light chain CDR3

<400> SEQUENCE: 54

Tyr Ser Thr Asp Arg Ser Gly Asn His Arg Val
1               5                   10

<210> SEQ ID NO 55
<211> LENGTH: 5
<212> TYPE: PRT
<213> ORGANISM: Artificial Sequence
<220> FEATURE:
<223> OTHER INFORMATION: durvalumab alternative heavy chain CDR1

<400> SEQUENCE: 55

```
Ser Tyr Trp Met Ser
1               5

<210> SEQ ID NO 56
<211> LENGTH: 17
<212> TYPE: PRT
<213> ORGANISM: Artificial Sequence
<220> FEATURE:
<223> OTHER INFORMATION: durvalumab alternative heavy chain CDR2

<400> SEQUENCE: 56

Asn Ile Lys Gln Asp Gly Gly Glu Gln Tyr Tyr Val Asp Ser Val Lys
1               5                   10                  15

Gly

<210> SEQ ID NO 57
<211> LENGTH: 11
<212> TYPE: PRT
<213> ORGANISM: Artificial Sequence
<220> FEATURE:
<223> OTHER INFORMATION: durvalumab alternative heavy chain CDR3

<400> SEQUENCE: 57

Asp Trp Asn Tyr Gly Tyr Tyr Asp Met Asp Val
1               5                   10

<210> SEQ ID NO 58
<211> LENGTH: 12
<212> TYPE: PRT
<213> ORGANISM: Artificial Sequence
<220> FEATURE:
<223> OTHER INFORMATION: durvalumab alternative light chain CDR1

<400> SEQUENCE: 58

Arg Ala Ser Gln Ser Val Ser Ser Asn Tyr Leu Ala
1               5                   10

<210> SEQ ID NO 59
<211> LENGTH: 7
<212> TYPE: PRT
<213> ORGANISM: Artificial Sequence
<220> FEATURE:
<223> OTHER INFORMATION: durvalumab alternative light chain CDR2

<400> SEQUENCE: 59

Gly Thr Ser Ser Arg Ala Thr
1               5

<210> SEQ ID NO 60
<211> LENGTH: 9
<212> TYPE: PRT
<213> ORGANISM: Artificial Sequence
<220> FEATURE:
<223> OTHER INFORMATION: durvalumab alternative light chain CDR3

<400> SEQUENCE: 60

Gln Gln Tyr Gly Ser Ser Ile Phe Thr
1               5

<210> SEQ ID NO 61
<211> LENGTH: 5
<212> TYPE: PRT
<213> ORGANISM: Artificial Sequence
<220> FEATURE:
<223> OTHER INFORMATION: durvalumab alternative heavy chain CDR1
```

```
<400> SEQUENCE: 61

Thr Tyr Ser Met Asn
1               5

<210> SEQ ID NO 62
<211> LENGTH: 17
<212> TYPE: PRT
<213> ORGANISM: Artificial Sequence
<220> FEATURE:
<223> OTHER INFORMATION: durvalumab alternative heavy chain CDR2

<400> SEQUENCE: 62

Ser Ile Ser Ser Ser Gly Asp Tyr Ile Tyr Tyr Ala Asp Ser Val Lys
1               5                   10                  15

Gly

<210> SEQ ID NO 63
<211> LENGTH: 11
<212> TYPE: PRT
<213> ORGANISM: Artificial Sequence
<220> FEATURE:
<223> OTHER INFORMATION: durvalumab alternative heavy chain CDR3

<400> SEQUENCE: 63

Asp Leu Val Thr Ser Met Val Ala Phe Asp Tyr
1               5                   10

<210> SEQ ID NO 64
<211> LENGTH: 11
<212> TYPE: PRT
<213> ORGANISM: Artificial Sequence
<220> FEATURE:
<223> OTHER INFORMATION: durvalumab alternative light chain CDR1

<400> SEQUENCE: 64

Ser Gly Asp Ala Leu Pro Gln Lys Tyr Val Phe
1               5                   10

<210> SEQ ID NO 65
<211> LENGTH: 7
<212> TYPE: PRT
<213> ORGANISM: Artificial Sequence
<220> FEATURE:
<223> OTHER INFORMATION: durvalumab alternative light chain CDR2

<400> SEQUENCE: 65

Glu Asp Ser Lys Arg Pro Ser
1               5

<210> SEQ ID NO 66
<211> LENGTH: 11
<212> TYPE: PRT
<213> ORGANISM: Artificial Sequence
<220> FEATURE:
<223> OTHER INFORMATION: durvalumab alternative light chain CDR3

<400> SEQUENCE: 66

Tyr Ser Thr Asp Arg Ser Gly Asn His Arg Val
1               5                   10

<210> SEQ ID NO 67
<211> LENGTH: 5
<212> TYPE: PRT
<213> ORGANISM: Artificial Sequence
<220> FEATURE:
<223> OTHER INFORMATION: durvalumab alternative heavy chain CDR1
```

```
<400> SEQUENCE: 67

Arg Tyr Trp Met Ser
1               5

<210> SEQ ID NO 68
<211> LENGTH: 17
<212> TYPE: PRT
<213> ORGANISM: Artificial Sequence
<220> FEATURE:
<223> OTHER INFORMATION: durvalumab alternative heavy chain CDR2

<400> SEQUENCE: 68

Asn Ile Lys Gln Asp Gly Ser Glu Lys Tyr Tyr Val Asp Ser Val Lys
1               5                   10                  15

Gly

<210> SEQ ID NO 69
<211> LENGTH: 12
<212> TYPE: PRT
<213> ORGANISM: Artificial Sequence
<220> FEATURE:
<223> OTHER INFORMATION: durvalumab alternative heavy chain CDR3

<400> SEQUENCE: 69

Glu Gly Gly Trp Phe Gly Glu Leu Ala Phe Asp Tyr
1               5                   10

<210> SEQ ID NO 70
<211> LENGTH: 12
<212> TYPE: PRT
<213> ORGANISM: Artificial Sequence
<220> FEATURE:
<223> OTHER INFORMATION: durvalumab alternative light chain CDR1

<400> SEQUENCE: 70

Arg Ala Ser Gln Arg Val Ser Ser Ser Tyr Leu Ala
1               5                   10

<210> SEQ ID NO 71
<211> LENGTH: 7
<212> TYPE: PRT
<213> ORGANISM: Artificial Sequence
<220> FEATURE:
<223> OTHER INFORMATION: durvalumab alternative light chain CDR2

<400> SEQUENCE: 71

Asp Ala Ser Ser Arg Ala Thr
1               5

<210> SEQ ID NO 72
<211> LENGTH: 9
<212> TYPE: PRT
<213> ORGANISM: Artificial Sequence
<220> FEATURE:
<223> OTHER INFORMATION: durvalumab alternative light chain CDR3

<400> SEQUENCE: 72

Gln Gln Tyr Gly Ser Leu Pro Trp Thr
1               5

<210> SEQ ID NO 73
<211> LENGTH: 448
<212> TYPE: PRT
<213> ORGANISM: Artificial Sequence
<220> FEATURE:
```

<223> OTHER INFORMATION: atezolizumab (MPDL3280A) heavy chain

<400> SEQUENCE: 73

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Ser
            20                  25                  30
Trp Ile His Trp Val Arg Gln Ala Pro Gly Lys Gly Leu Glu Trp Val
        35                  40                  45
Ala Trp Ile Ser Pro Tyr Gly Gly Ser Thr Tyr Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Arg His Trp Pro Gly Gly Phe Asp Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Ala Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 74
<211> LENGTH: 214
<212> TYPE: PRT
<213> ORGANISM: Artificial Sequence
<220> FEATURE:
<223> OTHER INFORMATION: atezolizumab (MPDL3280A) light chain

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 75
<211> LENGTH: 118
<212> TYPE: PRT
<213> ORGANISM: Artificial Sequence
<220> FEATURE:
<223> OTHER INFORMATION: atezolizumab (MPDL3280A) variable heavy chain

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45
```

```
Ala Trp Ile Ser Pro Tyr Gly Gly Ser Thr Tyr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
                100                 105                 110

Leu Val Thr Val Ser Ala
            115

<210> SEQ ID NO 76
<211> LENGTH: 108
<212> TYPE: PRT
<213> ORGANISM: Artificial Sequence
<220> FEATURE:
<223> OTHER INFORMATION: atezolizumab (MPDL3280A) variable light chain

<400> SEQUENCE: 76

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Tyr His Pro Ala
                 85                  90                  95

Thr Phe Gly Gln Gly Thr Lys Val Glu Ile Lys Arg
            100                 105

<210> SEQ ID NO 77
<211> LENGTH: 10
<212> TYPE: PRT
<213> ORGANISM: Artificial Sequence
<220> FEATURE:
<223> OTHER INFORMATION: atezolizumab (MPDL3280A) heavy chain HVR-H1
<220> FEATURE:
<221> NAME/KEY: misc_feature
<222> LOCATION: (6)..(6)
<223> OTHER INFORMATION: Xaa can be any naturally occurring amino acid

<400> SEQUENCE: 77

Gly Phe Thr Phe Ser Xaa Ser Trp Ile His
 1               5                  10

<210> SEQ ID NO 78
<211> LENGTH: 18
<212> TYPE: PRT
<213> ORGANISM: Artificial Sequence
<220> FEATURE:
<223> OTHER INFORMATION: atezolizumab (MPDL3280A) heavy chain HVR-H2
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
```

```
<400> SEQUENCE: 78

Ala Trp Ile Xaa Pro Tyr Gly Gly Ser Xaa Tyr Tyr Ala Asp Ser Val
1               5                   10                  15

Lys Gly

<210> SEQ ID NO 79
<211> LENGTH: 9
<212> TYPE: PRT
<213> ORGANISM: Artificial Sequence
<220> FEATURE:
<223> OTHER INFORMATION: atezolizumab (MPDL3280A) heavy chain HVR-H3

<400> SEQUENCE: 79

Arg His Trp Pro Gly Gly Phe Asp Tyr
1               5

<210> SEQ ID NO 80
<211> LENGTH: 11
<212> TYPE: PRT
<213> ORGANISM: Artificial Sequence
<220> FEATURE:
<223> OTHER INFORMATION: atezolizumab (MPDL3280A) heavy chain HVR-L1
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 80

Arg Ala Ser Gln Xaa Xaa Xaa Thr Xaa Xaa Ala
1               5                   10

<210> SEQ ID NO 81
<211> LENGTH: 7
<212> TYPE: PRT
<213> ORGANISM: Artificial Sequence
<220> FEATURE:
<223> OTHER INFORMATION: atezolizumab (MPDL3280A) heavy chain HVR-L2
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 81

Ser Ala Ser Xaa Leu Xaa Ser
1               5

<210> SEQ ID NO 82
<211> LENGTH: 9
<212> TYPE: PRT
<213> ORGANISM: Artificial Sequence
<220> FEATURE:
<223> OTHER INFORMATION: atezolizumab (MPDL3280A) heavy chain HVR-L3
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
```

```
<400> SEQUENCE: 82

Gln Gln Xaa Xaa Xaa Xaa Pro Xaa Thr
1               5

<210> SEQ ID NO 83
<211> LENGTH: 450
<212> TYPE: PRT
<213> ORGANISM: Artificial Sequence
<220> FEATURE:
<223> OTHER INFORMATION: avelumab (MSB0010718C) heavy chain

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
```

```
                    340                 345                 350
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 84
<211> LENGTH: 216
<212> TYPE: PRT
<213> ORGANISM: Artificial Sequence
<220> FEATURE:
<223> OTHER INFORMATION: avelumab (MSB0010718C) light chain

<400> SEQUENCE: 84

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 85
<211> LENGTH: 120
<212> TYPE: PRT
```

<213> ORGANISM: Artificial Sequence
<220> FEATURE:
<223> OTHER INFORMATION: avelumab (MSB0010718C) variable heavy chain

<400> SEQUENCE: 85

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Ile | Met | Met | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Ser | Ile | Tyr | Pro | Ser | Gly | Gly | Ile | Thr | Phe | Tyr | Ala | Asp | Thr | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Ile | Lys | Leu | Gly | Thr | Val | Thr | Thr | Val | Asp | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ser | Ser |
|---|---|---|---|---|---|---|---|
| | | 115 | | | | | 120 |

<210> SEQ ID NO 86
<211> LENGTH: 110
<212> TYPE: PRT
<213> ORGANISM: Artificial Sequence
<220> FEATURE:
<223> OTHER INFORMATION: avelumab (MSB0010718C) variable light chain

<400> SEQUENCE: 86

| Gln | Ser | Ala | Leu | Thr | Gln | Pro | Ala | Ser | Val | Ser | Gly | Ser | Pro | Gly | Gln |
|---|---|---|---|---|---|---|---|---|---|---|---|---|---|---|---|
| 1 | | | | 5 | | | | | 10 | | | | | 15 | |

| Ser | Ile | Thr | Ile | Ser | Cys | Thr | Gly | Thr | Ser | Ser | Asp | Val | Gly | Gly | Tyr |
|---|---|---|---|---|---|---|---|---|---|---|---|---|---|---|---|
| | | | 20 | | | | | 25 | | | | | 30 | | |

| Asn | Tyr | Val | Ser | Trp | Tyr | Gln | Gln | His | Pro | Gly | Lys | Ala | Pro | Lys | Leu |
|---|---|---|---|---|---|---|---|---|---|---|---|---|---|---|---|
| | | 35 | | | | | 40 | | | | | 45 | | | |

| Met | Ile | Tyr | Asp | Val | Ser | Asn | Arg | Pro | Ser | Gly | Val | Ser | Asn | Arg | Phe |
|---|---|---|---|---|---|---|---|---|---|---|---|---|---|---|---|
| 50 | | | | | 55 | | | | | 60 | | | | | |

| Ser | Gly | Ser | Lys | Ser | Gly | Asn | Thr | Ala | Ser | Leu | Thr | Ile | Ser | Gly | Leu |
|---|---|---|---|---|---|---|---|---|---|---|---|---|---|---|---|
| 65 | | | | | 70 | | | | | 75 | | | | | 80 |

| Gln | Ala | Glu | Asp | Glu | Ala | Asp | Tyr | Tyr | Cys | Ser | Ser | Tyr | Thr | Ser | Ser |
|---|---|---|---|---|---|---|---|---|---|---|---|---|---|---|---|
| | | | | 85 | | | | | 90 | | | | | 95 | |

| Ser | Thr | Arg | Val | Phe | Gly | Thr | Gly | Thr | Lys | Val | Thr | Val | Leu |
|---|---|---|---|---|---|---|---|---|---|---|---|---|---|
| | | | 100 | | | | | 105 | | | | | 110 |

<210> SEQ ID NO 87
<211> LENGTH: 5
<212> TYPE: PRT
<213> ORGANISM: Artificial Sequence
<220> FEATURE:
<223> OTHER INFORMATION: avelumab (MSB0010718C) heavy chain HVR-H1

<400> SEQUENCE: 87

| Ser | Tyr | Ile | Met | Met |
|---|---|---|---|---|
| 1 | | | | 5 |

<210> SEQ ID NO 88
<211> LENGTH: 17
<212> TYPE: PRT
<213> ORGANISM: Artificial Sequence

```
<220> FEATURE:
<223> OTHER INFORMATION: avelumab (MSB0010718C) heavy chain HVR-H2

<400> SEQUENCE: 88

Ser Ile Tyr Pro Ser Gly Gly Ile Thr Phe Tyr Ala Asp Thr Val Lys
1               5                   10                  15

Gly

<210> SEQ ID NO 89
<211> LENGTH: 11
<212> TYPE: PRT
<213> ORGANISM: Artificial Sequence
<220> FEATURE:
<223> OTHER INFORMATION: avelumab (MSB0010718C) heavy chain HVR-H3

<400> SEQUENCE: 89

Ile Lys Leu Gly Thr Val Thr Thr Val Asp Tyr
1               5                   10

<210> SEQ ID NO 90
<211> LENGTH: 14
<212> TYPE: PRT
<213> ORGANISM: Artificial Sequence
<220> FEATURE:
<223> OTHER INFORMATION: avelumab (MSB0010718C) heavy chain HVR-L1

<400> SEQUENCE: 90

Thr Gly Thr Ser Ser Asp Val Gly Gly Tyr Asn Tyr Val Ser
1               5                   10

<210> SEQ ID NO 91
<211> LENGTH: 7
<212> TYPE: PRT
<213> ORGANISM: Artificial Sequence
<220> FEATURE:
<223> OTHER INFORMATION: avelumab (MSB0010718C) heavy chain HVR-L2

<400> SEQUENCE: 91

Asp Val Ser Asn Arg Pro Ser
1               5

<210> SEQ ID NO 92
<211> LENGTH: 10
<212> TYPE: PRT
<213> ORGANISM: Artificial Sequence
<220> FEATURE:
<223> OTHER INFORMATION: avelumab (MSB0010718C) heavy chain HVR-L3

<400> SEQUENCE: 92

Ser Ser Tyr Thr Ser Ser Ser Thr Arg Val
1               5                   10

<210> SEQ ID NO 93
<211> LENGTH: 165
<212> TYPE: PRT
<213> ORGANISM: Artificial Sequence
<220> FEATURE:
<223> OTHER INFORMATION: rIFN-alpha 2b

<400> SEQUENCE: 93

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
```

```
            35                  40                  45
Lys Ala Glu Thr Ile Pro Val Leu His Glu Met Ile Gln Gln Ile Phe
 50                  55                  60
Asn Leu Phe Ser Thr Lys Asp Ser Ser Ala Ala Trp Asp Glu Thr Leu
 65                  70                  75                  80
Leu Asp Lys Phe Tyr Thr Glu Leu Tyr Gln Gln Leu Asn Asp Leu Glu
                 85                  90                  95
Ala Cys Val Ile Gln Gly Val Gly Val Thr Glu Thr Pro Leu Met Asn
             100                 105                 110
Glu Asp Ser Ile Leu Ala Val Arg Lys Tyr Phe Gln Arg Ile Thr Leu
             115                 120                 125
Tyr Leu Lys Glu Lys Lys Tyr Ser Pro Cys Ala Trp Glu Val Val Arg
130                 135                 140
Ala Glu Ile Met Arg Ser Phe Ser Leu Ser Thr Asn Leu Gln Glu Ser
145                 150                 155                 160
Leu Arg Ser Lys Glu
                165

<210> SEQ ID NO 94
<211> LENGTH: 165
<212> TYPE: PRT
<213> ORGANISM: Artificial Sequence
<220> FEATURE:
<223> OTHER INFORMATION: rIFN-alpha 2a

<400> SEQUENCE: 94

Cys Asp Leu Pro Gln Thr His Ser Leu Gly Ser Arg Arg Thr Leu Met
  1               5                  10                  15
Leu Leu Ala Gln Met Arg Lys Ile Ser Leu Phe Ser Cys Leu Lys Asp
                 20                  25                  30
Arg His Asp Phe Gly Phe Pro Gln Glu Glu Phe Gly Asn Gln Phe Gln
             35                  40                  45
Lys Ala Glu Thr Ile Pro Val Leu His Glu Met Ile Gln Gln Ile Phe
 50                  55                  60
Asn Leu Phe Ser Thr Lys Asp Ser Ser Ala Ala Trp Asp Glu Thr Leu
 65                  70                  75                  80
Leu Asp Lys Phe Tyr Thr Glu Leu Tyr Gln Gln Leu Asn Asp Leu Glu
                 85                  90                  95
Ala Cys Val Ile Gln Gly Val Gly Val Thr Glu Thr Pro Leu Met Lys
             100                 105                 110
Glu Asp Ser Ile Leu Ala Val Arg Lys Tyr Phe Gln Arg Ile Thr Leu
             115                 120                 125
Tyr Leu Lys Glu Lys Lys Tyr Ser Pro Cys Ala Trp Glu Val Val Arg
130                 135                 140
Ala Glu Ile Met Arg Ser Phe Ser Leu Ser Thr Asn Leu Gln Glu Ser
145                 150                 155                 160
Leu Arg Ser Lys Glu
                165

<210> SEQ ID NO 95
<211> LENGTH: 166
<212> TYPE: PRT
<213> ORGANISM: Artificial Sequence
<220> FEATURE:
<223> OTHER INFORMATION: Interferon alpha

<400> SEQUENCE: 95
```

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
            35                  40                  45

Gln Lys Ala Pro Ala Ile Ser Val Leu His Glu Leu Ile Gln Gln Ile
        50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
                100                 105                 110

Asn Ala Asp Ser Ile Leu Ala Val Lys Lys Tyr Phe Arg Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 96
<211> LENGTH: 165
<212> TYPE: PRT
<213> ORGANISM: Artificial Sequence
<220> FEATURE:
<223> OTHER INFORMATION: IFN-alpha2

<400> SEQUENCE: 96

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
        130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 97
<211> LENGTH: 166

```
<212> TYPE: PRT
<213> ORGANISM: Artificial Sequence
<220> FEATURE:
<223> OTHER INFORMATION: IFN-alpha8

<400> SEQUENCE: 97

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Ser Cys Val Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Phe Ser Leu Ser Ile Asn Leu Gln Lys
145                 150                 155                 160

Arg Leu Lys Ser Lys Glu
                165

<210> SEQ ID NO 98
<211> LENGTH: 166
<212> TYPE: PRT
<213> ORGANISM: Artificial Sequence
<220> FEATURE:
<223> OTHER INFORMATION: IFN-alpha10

<400> SEQUENCE: 98

Cys Asp Leu Pro Gln Thr His Ser Leu Gly Asn Arg Arg Ala Leu Ile
1               5                   10                  15

Leu Leu Gly Gln Met Gly Arg Ile Ser Pro Phe Ser Cys Leu Lys Asp
            20                  25                  30

Arg His Asp Phe Arg Ile Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Ile Glu Arg Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160
```

Arg Leu Arg Arg Lys Asp
                165

<210> SEQ ID NO 99
<211> LENGTH: 166
<212> TYPE: PRT
<213> ORGANISM: Artificial Sequence
<220> FEATURE:
<223> OTHER INFORMATION: IFN-alpha14

<400> SEQUENCE: 99

Cys Asn Leu Ser Gln Thr His Ser Leu Asn Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Glu Phe Pro Gln Glu Glu Phe Asp Gly Asn Gln Phe
        35                  40                  45

Gln Lys Ala Gln Ala Ile Ser Val Leu His Glu Met Met Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Lys Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 100
<211> LENGTH: 165
<212> TYPE: PRT
<213> ORGANISM: Artificial Sequence
<220> FEATURE:
<223> OTHER INFORMATION: IFN-alpha21

<400> SEQUENCE: 100

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Glu Gln Ser
65                  70                  75                  80

Leu Leu Glu Lys Phe Ser Thr Glu Leu Asn Gln Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Lys Lys Tyr Phe Gln Arg Ile Thr

```
                115                 120                 125
Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Lys Ile Phe Gln Glu
145                 150                 155                 160

Arg Leu Arg Arg Lys
                165

<210> SEQ ID NO 101
<211> LENGTH: 167
<212> TYPE: PRT
<213> ORGANISM: Artificial Sequence
<220> FEATURE:
<223> OTHER INFORMATION: interferon alfacon-1

<400> SEQUENCE: 101

Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
                20                  25                  30

Asp Arg His Asp Phe Gly Phe Pro Gln Glu Glu Phe Asp Gly Asn Gln
            35                  40                  45

Phe Gln Lys Ala Gln Ala Ile Ser Val Leu His Glu Met Ile Gln Gln
    50                  55                  60

Thr Phe Asn Leu Phe Ser Thr Lys Asp Ser Ser Ala Ala Trp Asp Glu
65                  70                  75                  80

Ser Leu Leu Glu Lys Phe Tyr Thr Glu Leu Tyr Gln Gln Leu Asn Asp
                85                  90                  95

Leu Glu Ala Cys Val Ile Gln Glu Val Gly Val Glu Glu Thr Pro Leu
            100                 105                 110

Met Asn Val Asp Ser Ile Leu Ala Val Lys Lys Tyr Phe Gln Arg Ile
    115                 120                 125

Thr Leu Tyr Leu Thr Glu Lys Lys Tyr Ser Pro Cys Ala Trp Glu Val
130                 135                 140

Val Arg Ala Glu Ile Met Arg Ser Phe Ser Leu Ser Thr Asn Leu Gln
145                 150                 155                 160

Glu Arg Leu Arg Arg Lys Glu
                165

<210> SEQ ID NO 102
<211> LENGTH: 165
<212> TYPE: PRT
<213> ORGANISM: Artificial Sequence
<220> FEATURE:
<223> OTHER INFORMATION: Interferon alfa-n1

<400> SEQUENCE: 102

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80
```

```
Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 103
<211> LENGTH: 165
<212> TYPE: PRT
<213> ORGANISM: Artificial Sequence
<220> FEATURE:
<223> OTHER INFORMATION: Interferon alfa-n3

<400> SEQUENCE: 103

```
Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 104
<211> LENGTH: 165
<212> TYPE: PRT
<213> ORGANISM: Artificial Sequence
<220> FEATURE:
<223> OTHER INFORMATION: Interferon alfa-n3

<400> SEQUENCE: 104

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45
```

```
Lys Ala Glu Thr Ile Pro Val Leu His Glu Met Ile Gln Gln Ile Phe
 50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Asn
                100                 105                 110

Glu Asp Ser Ile Leu Ala Val Arg Lys Tyr Phe Gln Arg Ile Thr Leu
                115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 105
<211> LENGTH: 165
<212> TYPE: PRT
<213> ORGANISM: Artificial Sequence
<220> FEATURE:
<223> OTHER INFORMATION: Interferon alfa-n3

<400> SEQUENCE: 105

Cys Asp Leu Pro Gln Thr His Ser Leu Gly Ser Arg Arg Thr Leu Met
  1               5                  10                  15

Leu Leu Ala Gln Met Arg Arg Ile Ser Leu Phe Ser Cys Leu Lys Asp
                 20                  25                  30

Arg Arg Asp Phe Gly Phe Pro Gln Glu Glu Phe Gly Asn Gln Phe Gln
                 35                  40                  45

Lys Ala Glu Thr Ile Pro Val Leu His Glu Met Ile Gln Gln Ile Phe
 50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Asn
                100                 105                 110

Glu Asp Ser Ile Leu Ala Val Arg Lys Tyr Phe Gln Arg Ile Thr Leu
                115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 106
<211> LENGTH: 166
<212> TYPE: PRT
<213> ORGANISM: Artificial Sequence
<220> FEATURE:
<223> OTHER INFORMATION: Interferon alfa-n3

<400> SEQUENCE: 106

Met Ser Tyr Asn Leu Leu Gly Phe Leu Gln Arg Ser Ser Asn Phe Gln
```

```
1               5                   10                  15
Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```